(12) United States Patent
Kawaue et al.

(10) Patent No.: US 11,474,432 B2
(45) Date of Patent: Oct. 18, 2022

(54) CHEMICALLY AMPLIFIED PHOTOSENSITIVE COMPOSITION, PHOTOSENSITIVE DRY FILM, METHOD OF MANUFACTURING PATTERNED RESIST FILM, METHOD OF MANUFACTURING SUBSTRATE WITH TEMPLATE, METHOD OF MANUFACTURING PLATED ARTICLE, AND COMPOUND

(71) Applicant: TOKYO OHKA KOGYO CO., LTD., Kawasaki (JP)

(72) Inventors: Akiya Kawaue, Kawasaki (JP); Yasushi Kuroiwa, Kawasaki (JP)

(73) Assignee: Tokyo Ohka Kogyo Co., Ltd., Kawasaki (JP)

( * ) Notice: Subject to any disclaimer, the term of this patent is extended or adjusted under 35 U.S.C. 154(b) by 41 days.

(21) Appl. No.: 16/715,685

(22) Filed: Dec. 16, 2019

(65) Prior Publication Data

US 2020/0209739 A1  Jul. 2, 2020

(30) Foreign Application Priority Data

Dec. 27, 2018 (JP) .............................. JP2018-246206

(51) Int. Cl.
| | | |
|---|---|---|
| *G03F 7/039* | (2006.01) | |
| *G03F 7/004* | (2006.01) | |
| *G03F 7/30* | (2006.01) | |
| *G03F 7/38* | (2006.01) | |
| *G03F 7/09* | (2006.01) | |
| *C07C 229/60* | (2006.01) | |
| *C08L 33/08* | (2006.01) | |
| *C08L 61/06* | (2006.01) | |
| *C08L 25/06* | (2006.01) | |

(52) U.S. Cl.
CPC .......... *G03F 7/0392* (2013.01); *C07C 229/60* (2013.01); *G03F 7/0042* (2013.01); *G03F 7/0045* (2013.01); *G03F 7/0397* (2013.01); *G03F 7/09* (2013.01); *G03F 7/30* (2013.01); *C08L 25/06* (2013.01); *C08L 33/08* (2013.01); *C08L 61/06* (2013.01); *G03F 7/38* (2013.01)

(58) Field of Classification Search
CPC ........ G03F 7/0392; G03F 7/0397; G03F 7/30; G03F 7/38; C07C 229/60
See application file for complete search history.

(56) References Cited

U.S. PATENT DOCUMENTS

| | | | |
|---|---|---|---|
| 2005/0208419 A1* | 9/2005 | Inabe | .................... G03F 7/0392 |
| | | | 430/270.1 |
| 2009/0068342 A1* | 3/2009 | Senzaki | ............ C08F 220/1807 |
| | | | 430/326 |
| 2010/0190104 A1* | 7/2010 | Nakamura | ............ G03F 7/0397 |
| | | | 430/326 |
| 2013/0089819 A1* | 4/2013 | Kawaue | ................ C07C 309/09 |
| | | | 430/285.1 |
| 2013/0310596 A1* | 11/2013 | Bezwada | ............. C08G 63/916 |
| | | | 560/45 |
| 2015/0044613 A1 | 2/2015 | Irie et al. | |
| 2017/0184923 A1* | 6/2017 | Omura | ................ C08G 73/1042 |

FOREIGN PATENT DOCUMENTS

| | | |
|---|---|---|
| JP | H09-176112 A | 7/1997 |
| JP | H11-052562 A | 2/1999 |
| JP | 2011-059277 A | 3/2011 |
| JP | 2015-034926 A | 2/2015 |
| JP | 2018-169543 A | 11/2018 |

* cited by examiner

*Primary Examiner* — John S Chu

(74) *Attorney, Agent, or Firm* — Knobbe Martens Olson & Bear LLP

(57) ABSTRACT

A chemically amplified photosensitive composition which forms a resist pattern whose cross-sectional shape is rectangular, and which has a wide depth of focus margin; a photosensitive dry film having a photosensitive layer made from the composition; a method of manufacturing a patterned-resist film using the composition; a method of manufacturing a substrate with a template using the composition; a method of manufacturing a plated article using the substrate with a template; and a novel compound. An acid diffusion suppressing agent having a specific structure is blended into the composition including an acid generator which generates acid upon exposure to an irradiated active ray or radiation.

13 Claims, No Drawings

CHEMICALLY AMPLIFIED PHOTOSENSITIVE COMPOSITION, PHOTOSENSITIVE DRY FILM, METHOD OF MANUFACTURING PATTERNED RESIST FILM, METHOD OF MANUFACTURING SUBSTRATE WITH TEMPLATE, METHOD OF MANUFACTURING PLATED ARTICLE, AND COMPOUND

RELATED APPLICATIONS

This application claims priority to Japanese Patent Application No. 2018-246206, filed Dec. 27, 2018, the entire content of which is incorporated herein by reference.

BACKGROUND OF THE INVENTION

Field of the Invention

The present invention relates to a chemically amplified photosensitive composition, a photosensitive dry film having a photosensitive layer formed from the chemically amplified photosensitive composition, a method of manufacturing a patterned resist film using the chemically amplified photosensitive composition, a method of manufacturing a substrate with a template using the chemically amplified photosensitive composition, a method of manufacturing a plated article using the substrate with a template, and a new compound.

Related Art

Photofabrication is now the mainstream of a microfabrication technique. Photofabrication is a generic term describing the technology used for manufacturing a wide variety of precision components such as semiconductor packages. The manufacturing is carried out by applying a photoresist composition to the surface of a processing target to form a photoresist layer, patterning this photoresist layer using photolithographic techniques, and then conducting chemical etching, electrolytic etching, or electroforming based mainly on electroplating, using the patterned photoresist layer (photoresist pattern) as a mask.

In recent years, high density packaging technologies have progressed in semiconductor packages along with downsizing electronics devices, and the increase in package density has been developed on the basis of mounting multi-pin thin film in packages, miniaturizing of package size, two-dimensional packaging technologies in flip-tip systems or three-dimensional packaging technologies. In these types of high density packaging techniques, connection terminals, for example, protruding electrodes (mounting terminals) known as bumps that protrude above the package or metal posts that extend from peripheral terminals on the wafer and connect rewiring with the mounting terminals, are disposed on the surface of the substrate with high precision.

In the photofabrication as described above, a photoresist composition is used, and chemically amplified photosensitive compositions containing an acid generator have been known as such a photoresist composition (see Patent Documents 1, 2 and the like). According to the chemically amplified photosensitive composition, an acid is generated from the acid generator upon irradiation with radiation (exposure) and diffusion of the acid is promoted through heat treatment, to cause an acid catalytic reaction with a base resin and the like in the composition resulting in a change to the alkali-solubility of the same.

Such chemically amplified positive-type photosensitive compositions are used, for example, in formation of plated articles such as bumps, metal posts, and Cu-rewiring by a plating step, in addition to patterned insulating film or formation of etching mask. Specifically, a photoresist layer having a desired film thickness is formed on a support such as a metal substrate using a chemically amplified photosensitive composition, and the photoresist layer is exposed through a predetermined mask pattern and is developed. Thereby, a photoresist pattern used as a template in which portions for forming plated articles have been selectively removed (stripped) is formed. Then, bumps or metal posts, and Cu rewiring can be formed by embedding a conductor such as copper into the removed portions (nonresist portions) using plating, and then removing the surrounding photoresist pattern.

Patent Document 1: Japanese Unexamined Patent Application, Publication No. H09-176112
Patent Document 2: Japanese Unexamined Patent Application, Publication No. H11-52562

SUMMARY OF THE INVENTION

In general, when a resist pattern is formed, its cross-sectional shape is desirably rectangular in many cases. In particular, formation of connection terminals such as bumps and metal posts, or formation of Cu rewiring, by the plating as mentioned above, the cross-sectional shape of a nonresist section of the resist pattern as a template is strongly desired to be rectangular. In the formation process of a plated article, when the cross-sectional shape of a nonresist section of the resist pattern as a template is rectangular, a contact area between the connection terminals such as bumps, metal posts, and the like, or the bottom surface of the Cu rewiring and a support can be sufficiently secured. Thus, connection terminals or Cu rewiring whose adhesion to the support is favorable can easily be obtained.

However, when a resist pattern is formed using conventionally known chemically amplified resist compositions as disclosed in Patent Documents 1 and 2, etc., resist pattern whose cross-sectional shape is rectangular is not easily formed so often. In this way, when conventionally known chemically amplified resist compositions as disclosed in Patent Documents 1 and 2, etc., are used, it is difficult to form a resist pattern having a desired cross-sectional shape.

Furthermore, a template pattern for plating may be formed on a substrate having warp or step difference derived from base material such as a polyimide film laminated on the substrate. Therefore, chemically amplified photoresist composition to be used for forming the template pattern for plating is desired to have such a wide depth of focus (DOF) margin as to form a pattern having a desired dimension and shape regardless of the degree of flatness of the substrate surface. The depth of focus (DOF) margin is a range of the depth of focus enabling a resist pattern to be formed with a dimension in which a deviation with respect to a target dimension is within a predetermined range when exposure is performed with a focus shifted up or down at the same exposure amount. A wider depth of focus (DOF) margin is preferable.

The present invention has been made in view of the above-mentioned problem. An object of the present invention is to provide a chemically amplified photosensitive composition with which the resist pattern whose cross-sectional shape is rectangular is easily formed and which has a wide depth of focus (DOF) margin; a photosensitive dry film having a photosensitive layer made of the chemically amplified photosensitive composition; a method of manufacturing a patterned-resist film using the chemically amplified photosensitive composition; a method of manufacturing a substrate with a template using the chemically amplified photosensitive composition; a method of manufacturing a plated article using the substrate with a template; and a new compound.

After conducting extensive studies in order to achieve the above-mentioned objects, the present inventors have found that the above-mentioned problem can be solved by blending an acid diffusion suppressing agent (C) having a specific structure into a chemically amplified photosensitive composition including an acid generator (A) which generates acid upon exposure to an irradiated active ray or radiation, and the present inventors have completed the present invention. Specifically, the present invention provides the followings.

A first aspect of the present invention is a chemically amplified photosensitive composition including an acid generator (A) which generates acid upon exposure to an irradiated active ray or radiation, and an acid diffusion suppressing agent (C), wherein the acid diffusion suppressing agent (C) includes a compound represented by the following formula (C1).

[Chem. 1]

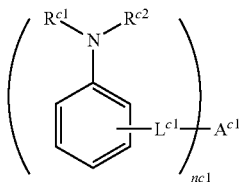

(C1)

(In the formula (C1),
a plurality of $R^{c1}$ each independently is an alkyl group having 1 or more and 6 or less carbon atoms optionally having a substituent, or a hydrogen atom;
a plurality of $R^{c2}$ each independently is an alkyl group having 1 or more and 6 or less carbon atoms optionally having a substituent, or a hydrogen atom;
the $R^{c1}$ and $R^{c2}$ may be linked to each other to form a ring;
$A^{c1}$ is an nc1-valence organic group including a cyclic group optionally having a substituent;
a plurality of $L^{c1}$ each independently is a single bond or a divalent linking group;
the $L^{c1}$ is bonded to the cyclic group in the $A^{c1}$; and
nc1 is an integer of 2 or more.)

A second aspect of the present invention is a photosensitive dry film comprising a substrate film, and a photosensitive layer formed on a surface of the substrate film, wherein the photosensitive layer includes the chemically amplified photosensitive composition according to the first aspect.

A third aspect of the present invention is a method of manufacturing a patterned resist film, the method including: laminating a photosensitive layer on a substrate, the layer including the chemically amplified photosensitive composition according to the first aspect;
exposing the photosensitive layer through irradiation with an active ray or radiation in a position-selective manner; and developing the exposed photosensitive layer.

A fourth aspect of the present invention is a method of manufacturing a substrate with a template, the method comprising: laminating a photosensitive layer on a substrate having a metal surface, the layer including the chemically amplified photosensitive composition of the first aspect; exposing the photosensitive layer through irradiation with an active ray or radiation in a position-selective manner; and developing the exposed photosensitive layer to form a template for plated article.

A fifth aspect of the present invention is a method of manufacturing a plated article, the method comprising plating the substrate with a template to form a plated article in the template, the substrate being manufactured by the method of manufacturing substrate with a template according to the fourth aspect.

A sixth aspect of the present invention is a compound represented by the following formula (C2).

[Chem. 2]

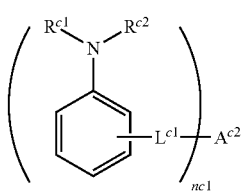

(C2)

(In the formula (C2),
a plurality of $R^{c1}$ each independently is an alkyl group having 1 or more and 6 or less carbon atoms optionally having a substituent, or a hydrogen atom;
a plurality of $R^{c2}$ each independently is an alkyl group having 1 or more and 6 or less carbon atoms optionally having a substituent, or a hydrogen atom;
the $R^{c1}$ and $R^{c2}$ are linked to each other to form a ring;
$A^{c2}$ is an nc1-valence organic group including two or more aromatic groups optionally having a substituent;
a plurality of $L^{c1}$ each independently is a single bond or a divalent linking group;
the $L^{c1}$ is bonded to the aromatic group in the $A^{c2}$; and nc1 is an integer of 2 or more.)

The present invention can provide a chemically amplified photosensitive composition with which the resist pattern whose cross-sectional shape is rectangular is easily formed and which has a wide depth of focus (DOF) margin; a photosensitive dry film having a photosensitive layer made of the chemically amplified photosensitive composition; a method of manufacturing a patterned-resist film using the chemically amplified photosensitive composition; a method of manufacturing a substrate with a template using the chemically amplified photosensitive composition; a method of manufacturing a plated article using the substrate with a template; and a new compound.

DETAILED DESCRIPTION OF THE INVENTION

«Chemically Amplified Photosensitive Composition»

The chemically amplified photosensitive composition (hereinafter, also referred to as the "photosensitive composition") includes an acid generator (A) which generates acid upon exposure to an irradiated active ray or radiation (hereinafter also referred to as the "acid generator (A)"), and an acid diffusion suppressing agent (C). The acid diffusion suppressing agent (C) has a specific structure as mentioned below.

The chemically amplified photosensitive composition is the same as a conventionally known chemically amplified photosensitive composition including an acid generator (A) and an acid diffusion suppressing agent (C) having a specific structure are included. The chemically amplified photosensitive composition may be a positive-type photosensitive composition whose solubility in a developing solution increases under the action of acid generated upon exposure to light, and may be a negative-type photosensitive composition whose solubility in a developing solution decreases under the action of acid under generated upon exposure to light.

Examples of the positive-type chemically amplified photosensitive composition include a photosensitive composition including a resin (B) whose solubility in alkali increases under an action of acid, including an alkali soluble group protected by a group to be deprotected by the action of acid such as a tert-butyl group, a tert-butoxy carbonyl group, a tetrahydropyranyl group, an acetal group, and a trimethylsilyl group in addition to the acid generator (A) and an acid diffusion suppressing agent (C). Examples of the negative-type chemically amplified photosensitive composition include a photosensitive composition including the acid generator (A) and the acid diffusion suppressing agent (C) as well as a condensing agent such as methylol melamine, and a resin which can be crosslinked by a condensing agent such as novolac resin. When such a photosensitive composition is exposed to light, the photosensitive composition is cured by a crosslinking reaction caused by an acid generated by the exposure. Furthermore, as the negative-type chemically amplified photosensitive composition, a photosensitive composition including an epoxy compound together with the acid generator (A) and the acid diffusion suppressing agent (C) is preferable. When such a photosensitive composition is exposed to light, cationic polymerization of the epoxy compound proceeds by an acid generated by exposure to light, and as a result, the photosensitive composition is cured.

Among these chemically amplified photosensitive compositions, the chemically amplified positive-type photosensitive composition including an acid generator (A), a resin (B) whose solubility in alkali increases under an action of acid, and an acid diffusion suppressing agent (C) is preferable, because desired high sensitivity can be achieved particularly easily, and because the patterned resist film is easily provided with desired characteristics by adjusting the types of constituent units or the ratio of the constituent units of a resin (B) whose solubility in alkali increases under an action of acid.

Hereinafter, as a representative example of the photosensitive composition, as to a chemically amplified positive-type photosensitive composition (hereinafter, also referred to as "photosensitive composition") including an acid generator (A), a resin (B) whose solubility in alkali increases under an action of acid (hereinafter, also referred to as "resin (B)), and an acid diffusion suppressing agent (C), essential or optional components, and the manufacturing method will be described. Note here that the below-mentioned acid generator (A) and acid diffusion suppressing agent (C) are applicable to photosensitive compositions other than the positive-type photosensitive composition mentioned below.

<Acid Generator (A)>

The acid generator (A) is a compound capable of producing an acid when irradiated with an active ray or radiation, and is not particularly limited as long as it is a compound which directly or indirectly produces an acid under the action of light. The acid generator (A) is preferably any one of the acid generators of the first to fifth aspects that will be described below. Hereinafter, among the suitably used acid generators (A) in the positive-type photosensitive composition, suitable acid generators (A) will be described as the first to fifth aspects.

The first aspect of the acid generator (A) may be a compound represented by the following formula (a1).

[Chem. 3]

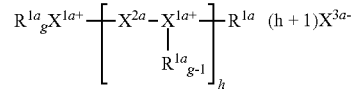
(a1)

In the formula (a1), $X^{1a}$ represents a sulfur atom or iodine atom respectively having a valence of g; g represents 1 or 2. h represents the number of repeating units in the structure within parentheses. $R^{1a}$ represents an organic group that is bonded to $X^{1a}$, and represents an aryl group having 6 or more and 30 or less carbon atoms, a heterocyclic group having 4 or more and 30 or less carbon atoms, an alkyl group having 1 or more and 30 or less carbon atoms, an alkenyl group having 2 or more and 30 or less carbon atoms, or an alkynyl group having 2 or more and 30 or less carbon atoms, and $R^{1a}$ may be substituted with at least one selected from the group consisting of an alkyl group, a hydroxyl group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic group, an aryloxy group, an alkylsulfinyl group, an arylsulfinyl group, an alkylsulfonyl group, an arylsulfonyl group, an alkyleneoxy group, an amino group, a cyano group, a nitro group, and halogen atoms. The number of $R^{1a}$s is $g+h(g-1)+1$, and the $R^{1a}$s may be respectively identical to or different from each other. Furthermore, two or more $R^{1a}$s may be bonded to each other directly or via —O—, —S—, —SO—, —SO$_2$—, —NH—, —NR$^{2a}$—, —CO—, —COO—, —CONH—, an alkylene group having 1 or more and 3 or less carbon atoms, or a phenylene group, and may form a ring structure including $X^{1a}$. $R^{2a}$ represents an alkyl group having 1 or more and 5 or less carbon atoms, or an aryl group having 6 or more and 10 or less carbon atoms.

$X^{2a}$ represents a structure represented by the following formula (a2).

[Chem. 4]

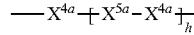
(a2)

In the above formula (a2), $X^{4a}$ represents an alkylene group having 1 or more and 8 or less carbon atoms, an arylene group having 6 or more and 20 or less carbon atoms, or a divalent group of a heterocyclic compound having 8 or more and 20 or less carbon atoms, and $X^{4a}$ may be substituted with at least one selected from the group consisting of an alkyl group having 1 or more and 8 or less carbon atoms, an alkoxy group having 1 or more and 8 or less carbon atoms, an aryl group having 6 or more and 10 or less carbon atoms, a hydroxyl group, a cyano group, a nitro group, and halogen atoms. $X^{5a}$ represents —O—, —S—, —SO—, —SO$_2$—, —NH—, —NR$^{2a}$—, —CO—, —COO—, —CONH—, an alkylene group having 1 or more and 3 or less carbon atoms, or a phenylene group. h represents the number of repeating units of the structure in parentheses. $X^{4a}$s in the number of h+1 and $X^{5a}$s in the number of h may be identical to or different from each other. $R^{2a}$ has the same definition as described above.

$X^{3a}$ represents a counterion of an onium, and examples thereof include a fluorinated alkylfluorophosphoric acid anion represented by the following formula (a17) or a borate anion represented by the following formula (a18).

[Chem. 5]

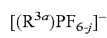
(a17)

In the formula (a17), $R^{3a}$ represents an alkyl group having 80% or more of the hydrogen atoms substituted with fluorine atoms. j represents the number of $R^{3a}$s and is an integer of 1 or more and 5 or less. $R^{3a}$s in the number of j may be respectively identical to or different from each other.

[Chem. 6]

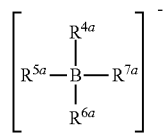
(a18)

In the formula (a18), $R^{4a}$ to $R^{7a}$ each independently represents a fluorine atom or a phenyl group, and a part or all of the hydrogen atoms of the phenyl group may be substituted with at least one selected from the group consisting of a fluorine atom and a trifluoromethyl group.

Examples of the onium ion in the compound represented by the above formula (a1) include triphenylsulfonium, tri-p-tolylsulfonium, 4-(phenylthio)phenyldiphenylsulfonium, bis[4-(diphenylsulfonio)phenyl] sulfide, bis[4-{bis[4-(2-hydroxyethoxy)phenyl]sulfonio}phenyl] sulfide, bis{4-[bis(4-fluorophenyl)sulfonio]phenyl} sulfide, 4-(4-benzoyl-2-chlorophenylthio)phenylbis(4-fluorophenyl)sulfonium, 7-isopropyl-9-oxo-10-thia-9,10-dihydroanthracen-2-yldi-p-tolylsulfonium, 7-isopropyl-9-oxo-10-thia-9,10-dihydroanthracen-2-yldiphenylsulfonium, 2-[(diphenyl)sulfonio]thioxanthone, 4-[4-(4-tert-butylbenzoyl)phenylthio]phenyldi-p-tolylsulfonium, 4-(4-benzoylphenylthio)phenyldiphenylsulfonium, diphenylphenacylsulfonium, 4-hydroxyphenylmethylbenzylsulfo-nium, 2-naphthylmethyl(1-ethoxycarbonyl)ethylsulfonium, 4-hydroxyphenylmethylphenacylsulfonium, phenyl[4-(4-biphenylthio)phenyl]-4-biphenylsulfonium, phenyl[4-(4-biphenylthio)phenyl]-3-biphenylsulfonium, [4-(4-acetophenylthio)phenyl]diphenylsulfonium, octadecylmethylphenacylsulfonium, diphenyliodonium, di-p-tolyliodonium, bis(4-dodecylphenyl)iodonium, bis(4-methoxyphenyl)iodonium, (4-octyloxyphenyl)phenyliodonium, bis(4-decyloxy)phenyliodonium, 4-(2-hydroxytetradecyloxy)phenylphenyliodonium, 4-isopropylphenyl(p-tolyl)iodonium, 4-isobutylphenyl(p-tolyl)iodonium, or the like.

Among the onium ions in the compound represented by the above formula (a1), a preferred onium ion may be a sulfonium ion represented by the following formula (a19).

[Chem. 7]

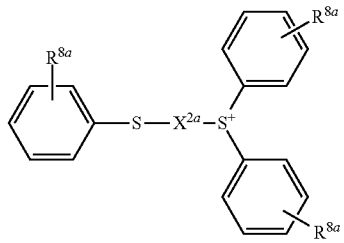
(a19)

In the above formula (a19), $R^{8a}$s each independently represents a hydrogen atom or a group selected from the group consisting of alkyl, hydroxyl, alkoxy, alkylcarbonyl, alkylcarbonyloxy, alkyloxycarbonyl, a halogen atom, an aryl, which may be substituted, and arylcarbonyl. $X^{2a}$ has the same definition as $X^{2a}$ in the above formula (a1).

Specific examples of the sulfonium ion represented by the above formula (a19) include 4-(phenylthio)phenyldiphenylsulfonium, 4-(4-benzoyl-2-chlorophenylthio)phenylbis(4-fluorophenyl)sulfonium, 4-(4-benzoylphenylthio)phenyldiphenylsulfonium, phenyl[4-(4-biphenylthio)phenyl]-4-biphenylsulfonium, phenyl[4-(4-biphenylthio)phenyl]-3-biphenylsulfonium, [4-(4-acetophenylthio)phenyl]diphenylsulfonium, and diphenyl[4-(p-terphenylthio)phenyl]diphenylsulfonium.

In regard to the fluorinated alkylfluorophosphoric acid anion represented by the above formula (a17), $R^{3a}$ represents an alkyl group substituted with a fluorine atom, and a preferred number of carbon atoms is 1 or more and 8 or less, while a more preferred number of carbon atoms is 1 or more and 4 or less. Specific examples of the alkyl group include linear alkyl groups such as methyl, ethyl, propyl, butyl, pentyl and octyl; branched alkyl groups such as isopropyl, isobutyl, sec-butyl and tert-butyl; and cycloalkyl groups such as cyclopropyl, cyclobutyl, cyclopentyl, and cyclohexyl. The proportion of hydrogen atoms substituted with fluorine atoms in the alkyl groups is usually 80% or more, preferably 90% or more, and even more preferably 100%. If the substitution ratio of fluorine atoms is less than 80%, the acid strength of the onium fluorinated alkylfluorophosphate represented by the above formula (a1) decreases.

A particularly preferred example of $R^{3a}$ is a linear or branched perfluoroalkyl group having 1 or more and 4 or less carbon atoms and a substitution ratio of fluorine atoms of 100%. Specific examples thereof include $CF_3$, $CF_3CF_2$, $(CF_3)_2CF$, $CF_3CF_2CF_2$, $CF_3CF_2CF_2CF_2$, $(CF_3)_2CFCF_2$, $CF_3CF_2(CF_3)CF$, and $(CF_3)_3C$. j which is the number of $R^{3a}$s represents an integer of 1 or more and 5 or less, and is preferably 2 or more and 4 or less, and particularly preferably 2 or 3.

Preferred specific examples of the fluorinated alkylfluorophosphoric acid anion include $[(CF_3CF_2)_2PF_4]^-$, $[(CF_3CF_2)_3PF_3]^-$, $[((CF_3)_2CF)_2PF_4]^-$, $[((CF_3)_2CF)_3PF_3]^-$, $[(CF_3CF_2CF_2)_2PF_4]^-$, $[(CF_3CF_2CF_2)_3PF_3]^-$, $[((CF_3)_2CFCF_2)_2PF_4]^-$, $[((CF_3)_2CFCF_2)_3PF_3]^-$, $[(CF_3CF_2CF_2CF_2)_2PF_4]^-$, or $[(CF_3CF_2CF_2)_3PF_3]^-$. Among these, $[(CF_3CF_2)_3PF_3]^-$, $[(CF_3CF_2CF_2)_3PF_3]^-$, $[((CF_3)_2CF)_3PF_3]^-$, $[((CF_3)_2CF)_2PF_4]^-$, $[((CF_3)_2CFCF_2)_3PF_3]^-$, or $[((CF_3)_2CFCF_2)_2PF_4]$ are particularly preferred.

Preferred specific examples of the borate anion represented by the above formula (a18) include tetrakis(pentafluorophenyl)borate $([B(C_6F_5)_4]^-)$, tetrakis[(trifluoromethyl)phenyl]borate $([B(C_6H_4CF_3)_4]^-)$, difluorobis (pentafluorophenyl)borate ($[(C_6F_5)_2BF_2]^-$), trifluoro(pentafluorophenyl)borate ($[(C_6F_5)BF_3]^-$), and tetrakis (difluorophenyl)borate ($[B(C_6H_3F_2)_4]^-$). Among these, tetrakis (pentafluorophenyl)borate ($[B(C_6F_5)_4]^-$) is particularly preferred.

The second aspect of the acid generator (A) include halogen-containing triazine compounds such as 2,4-bis(trichloromethyl)-6-piperonyl-1,3,5-triazine, 2,4-bis(trichloromethyl)-6-[2-(2-furyl)ethenyl]-s-triazine, 2,4-bis(trichloromethyl)-6-[2-(5-methyl-2-furyl)ethenyl]-s-triazine, 2,4-bis(trichloromethyl)-6-[2-(5-ethyl-2-furyl)ethenyl]-s-triazine, 2,4-bis(trichloromethyl)-6-[2-(5-propyl-2-furyl)ethenyl]-s-triazine, 2,4-bis(trichloromethyl)-6-[2-(3,5-dimethoxyphenyl)ethenyl]-s-triazine, 2,4-bis(trichloromethyl)-6-[2-(3,5-diethoxyphenyl)ethenyl]-s-triazine, 2,4-bis(trichloromethyl)-6-[2-(3,5-dipropoxyphenyl)ethenyl]-s-triazine, 2,4-bis(trichloromethyl)-6-[2-(3-methoxy-5-ethoxyphenyl)ethenyl]-s-triazine, 2,4-bis(trichloromethyl)-6-[2-(3-methoxy-5-propoxyphenyl)ethenyl]-s-triazine, 2,4-bis(trichloromethyl)-6-[2-(3,4-methylenedioxyphenyl)ethenyl]-s-triazine, 2,4-bis(trichloromethyl)-6-(3,4-methylenedioxyphenyl)-s-triazine, 2,4-bis-trichloromethyl-6-(3-bromo-4-methoxy)phenyl-s-triazine, 2,4-bis-trichloromethyl-6-(2-bromo-4-methoxy)phenyl-s-triazine, 2,4-bis-trichloromethyl-6-(2-bromo-4-methoxy)styrylphenyl-s-triazine, 2,4-bis-trichloromethyl-6-(3-bromo-4-methoxy)styrylphenyl-s-triazine, 2-(4-methoxyphenyl)-4,6-bis(trichloromethyl)-1,3,5-triazine, 2-(4-methoxynaphthyl)-4,6-bis(trichloromethyl)-1,3,5-triazine, 2-[2-(2-furyl)ethenyl]-4,6-bis(trichloromethyl)-1,3,5-triazine, 2-[2-(5-methyl-2-furyl)ethenyl]-4,6-bis(trichloromethyl)-1,3,5-triazine, 2-[2-(3,5-dimethoxyphenyl)ethenyl]-4,6-bis(trichloromethyl)-1,3,5-triazine, 2-[2-(3,4-dimethoxyphenyl)ethenyl]-4,6-bis(trichloromethyl)-1,3,5-triazine, 2-(3,4-methylenedioxyphenyl)-4,6-bis(trichloromethyl)-1,3,5-triazine, tris(1,3-dibromopropyl)-1,3,5-triazine and tris(2,3-dibromopropyl)-1,3,5-triazine, and halogen-containing triazine compounds represented by the following formula (a3) such as tris(2,3-dibromopropyl)isocyanurate.

[Chem. 8]

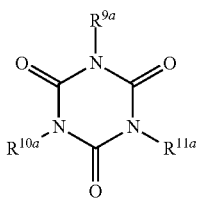

(a3)

In the above formula (a3), $R^{9a}$, $R^{10a}$, and $R^{11a}$ each independently represent a halogenated alkyl group.

Further, the third aspect of the acid generator (A) include α-(p-toluenesulfonyloxyimino)-phenylacetonitrile, α-(benzenesulfonyloxyimino)-2,4-dichlorophenylacetonitrile, α-(benzenesulfonyloxyimino)-2,6-dichlorophenylacetonitrile, α-(2-chlorobenzenesulfonyloxyimino)-4-methoxyphenylacetonitrile and α-(ethylsulfonyloxyimino)-1-cyclopentenylacetonitrile, and compounds represented by the following formula (a4) having an oximesulfonate group.

[Chem. 9]

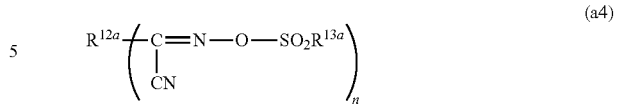

(a4)

In the above formula (a4), $R^{12a}$ represents a monovalent, bivalent or trivalent organic group, $R^{13a}$ represents a substituted or unsubstituted saturated hydrocarbon group, an unsaturated hydrocarbon group, or an aromatic group, and n represents the number of repeating units of the structure in the parentheses.

In the formula (a4), examples of the aromatic group include aryl groups such as a phenyl group and a naphthyl group, and heteroaryl groups such as a furyl group and a thienyl group. These may have one or more appropriate substituents such as halogen atoms, alkyl groups, alkoxy groups and nitro groups on the rings. It is particularly preferable that $R^{13a}$ is an alkyl group having 1 or more and 6 or less carbon atoms such as a methyl group, an ethyl group, a propyl group, and a butyl group. In particular, compounds in which $R^{12a}$ represents an aromatic group, and $R^{13a}$ represents an alkyl group having 1 or more and 4 or less carbon atoms are preferred.

Examples of the acid generator represented by the above formula (a4) include compounds in which $R^{12a}$ is any one of a phenyl group, a methylphenyl group and a methoxyphenyl group, and $R^{13a}$ is a methyl group, provided that n is 1, and specific examples thereof include α-(methylsulfonyloxyimino)-1-phenylacetonitrile, α-(methylsulfonyloxyimino)-1-(p-methylphenyl)acetonitrile, α-(methylsulfonyloxyimino)-1-(p-methoxyphenyl)acetonitrile, [2-(propylsulfonyloxyimino)-2,3-dihydroxythiophene-3-ylidene](o-tolyl)acetonitrile and the like. Provided that n is 2, the acid generator represented by the above formula (a4) is specifically an acid generator represented by the following formulae.

[Chem. 10]

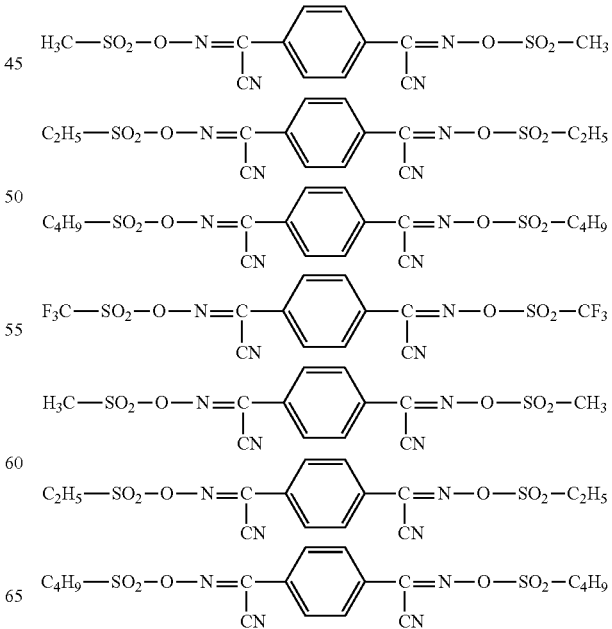

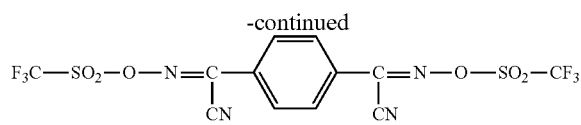

In addition, the fourth aspect of the acid generator (A) include onium salts that have a naphthalene ring at their cation moiety. The expression "have a naphthalene ring" indicates having a structure derived from naphthalene and also indicates at least two ring structures and their aromatic properties are maintained. The naphthalene ring may have a substituent such as a linear or branched alkyl group having 1 or more and 6 or less carbon atoms, a hydroxyl group, a linear or branched alkoxy group having 1 or more and 6 or less carbon atoms or the like. The structure derived from the naphthalene ring, which may be of a monovalent group (one free valance) or of a bivalent group (two free valences), is desirably of a monovalent group (in this regard, the number of free valance is counted except for the portions connecting with the substituents described above). The number of naphthalene rings is preferably 1 or more and 3 or less.

Preferably, the cation moiety of the onium salt having a naphthalene ring at the cation moiety is of the structure represented by the following formula (a5).

[Chem. 11]

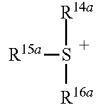

(a5)

In the above formula (a5), at least one of $R^{14a}$, $R^{15a}$ and $R^{16a}$ represents a group represented by the following formula (a6), and the remaining represents a linear or branched alkyl group having 1 or more and 6 or less carbon atoms, a phenyl group optionally having a substituent, a hydroxyl group, or a linear or branched alkoxy group having 1 or more and 6 or less carbon atoms. Alternatively, one of $R^{14a}$, $R^{15a}$ and $R^{16a}$ is a group represented by the following formula (a6), and the remaining two are each independently a linear or branched alkylene group having 1 or more and 6 or less carbon atoms, and these terminals may bond to form a ring structure.

[Chem. 12]

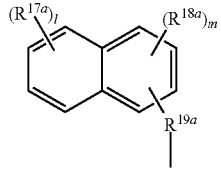

(a6)

In the formula (a6), $R^{17a}$ and $R^{18a}$ each independently represent a hydroxyl group, a linear or branched alkoxy group having 1 or more and 6 or less carbon atoms, or a linear or branched alkyl group having 1 or more and 6 or less carbon atoms, and $R^{19a}$ represents a single bond or a linear or branched alkylene group having 1 or more and 6 or less carbon atoms that may have a substituent. l and m each independently represent an integer of 0 or more and 2 or less, and l+m is 3 or less. Herein, when there exists a plurality of $R^{17a}$, they may be identical to or different from each other. Furthermore, when there exists a plurality of $R^{18a}$, they may be identical to or different from each other.

Preferably, among $R^{14a}$, $R^{15a}$ and $R^{16a}$ as above, the number of groups represented by the above formula (a6) is one in view of the stability of the compound, and the remaining are linear or branched alkylene groups having 1 or more and 6 or less carbon atoms of which the terminals may bond to form a ring. In this case, the two alkylene groups described above form a 3 to 9 membered ring including sulfur atom(s). Preferably, the number of atoms to form the ring (including sulfur atom(s)) is 5 or more and 6 or less.

Examples of the substituent, which the alkylene group may have, include an oxygen atom (in this case, a carbonyl group is formed together with a carbon atom that constitutes the alkylene group), a hydroxyl group or the like.

Furthermore, examples of the substituent, which the phenyl group may have, include a hydroxyl group, a linear or branched alkoxy group having 1 or more and 6 or less carbon atoms, a linear or branched alkyl group having 1 or more and 6 or less carbon atoms, or the like.

Examples of suitable cations for the suitable cation moiety include cations represented by the following formulae (a7) and (a8), and the structure represented by the following formula (a8) is particularly preferable.

[Chem. 13]

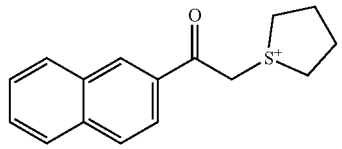

(a7)

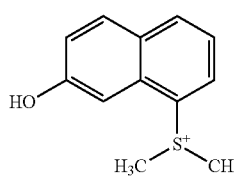

(a8)

The cation moieties, which may be of an iodonium salt or a sulfonium salt, are desirably of a sulfonium salt in view of acid-producing efficiency.

It is, therefore, desirable that the suitable anions for the anion moiety of the onium salt having a naphthalene ring at the cation moiety is an anion capable of forming a sulfonium salt.

The anion moiety of the acid generator is exemplified by fluoroalkylsulfonic acid ions or aryl sulfonic acid ions, of which hydrogen atom(s) being partially or entirely fluorinated.

The alkyl group of the fluoroalkylsulfonic acid ions may be linear, branched or cyclic and have 1 or more and 20 or less carbon atoms. Preferably, the carbon number is 1 or more and 10 or less in view of bulkiness and diffusion distance of the produced acid. In particular, branched or cyclic alkyl groups are preferable due to shorter diffusion length. Also, methyl, ethyl, propyl, butyl, octyl groups and the like are preferable due to being inexpensively synthesizable.

The aryl group of the aryl sulfonic acid ions may be an aryl group having 6 or more and 20 or less carbon atoms, and is exemplified by a phenol group or a naphthyl group that may be unsubstituted or substituted with an alkyl group or a halogen atom. In particular, aryl groups having 6 or more and 10 or less carbon atoms are preferable due to being inexpensively synthesizable. Specific examples of preferable aryl group include phenyl, toluenesulfonyl, ethylphenyl, naphthyl, methylnaphthyl groups and the like.

When hydrogen atoms in the above fluoroalkylsulfonic acid ion or the aryl sulfonic acid ion are partially or entirely substituted with a fluorine atom, the fluorination rate is preferably 10% or more and 100% or less, and more preferably 50% or more and 100% or less; it is particularly preferable that all hydrogen atoms are each substituted with a fluorine atom in view of higher acid strength. Specific examples thereof include trifluoromethane sulfonate, perfluorobutane sulfonate, perfluorooctane sulfonate, perfluorobenzene sulfonate, and the like.

Among these, the preferable anion moiety is exemplified by those represented by the following formula (a9).

[Chem. 14]

(a9)

In the above formula (a9), $R^{20a}$ represents groups represented by the following formulae (a10), (a11), and (a12).

[Chem. 15]

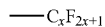

(a10)

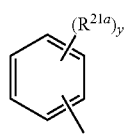

(a11)

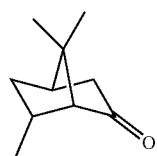

(a12)

In the above formula (a10), x represents an integer of 1 or more and 4 or less. Also, in the above formula (a11), $R^{21a}$ represents a hydrogen atom, a hydroxyl group, a linear or branched alkyl group having 1 or more and 6 or less carbon atoms, or a linear or branched alkoxy group having 1 or more and 6 or less carbon atoms, and y represents an integer of 1 or more and 3 or less. Of these, trifluoromethane sulfonate, and perfluorobutane sulfonate are preferable in view of safety.

In addition, a nitrogen-containing moiety represented by the following formulae (a13) and (a14) may also be used for the anion moiety.

[Chem. 16]

(a13)

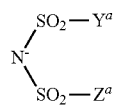

(a14)

In the formulae (a13) and (a14), $X^a$ represents a linear or branched alkylene group in which at least one hydrogen atom is substituted with a fluorine atom, the carbon number of the alkylene group is 2 or more and 6 or less, preferably 3 or more and 5 or less, and most preferably the carbon number is 3. In addition, $Y^a$ and $Z^a$ each independently represent a linear or branched alkyl group of which at least one hydrogen atom is substituted with a fluorine atom, the number of carbon atoms of the alkyl group is 1 or more and 10 or less, preferably 1 or more and 7 or less, and more preferably 1 or more and 3 or less.

The smaller number of carbon atoms in the alkylene group of $X^a$, or in the alkyl group of $Y^a$ or $Z^a$ is preferred since the solubility into organic solvent is favorable.

In addition, a larger number of hydrogen atoms each substituted with a fluorine atom in the alkylene group of $X^a$, or in the alkyl group of $Y^a$ or $Z^a$ is preferred since the acid strength becomes greater. The percentage of fluorine atoms in the alkylene group or alkyl group, i.e., the fluorination rate is preferably 70% or more and 100% or less and more preferably 90% or more and 100% or less, and most preferable are perfluoroalkylene or perfluoroalkyl groups in which all of the hydrogen atoms are each substituted with a fluorine atom.

Examples of preferable compounds for onium salts having a naphthalene ring at their cation moieties include compounds represented by the following formulae (a15) and (a16).

[Chem. 17]

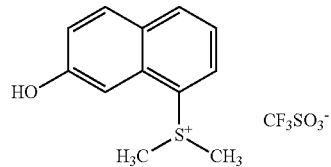

(a15)

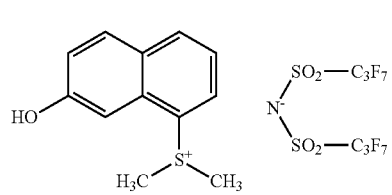

(a16)

Also, the fifth aspect of the acid generator (A) include bissulfonyldiazomethanes such as bis(p-toluenesulfonyl)diazomethane, bis(1,1-dimethyl ethylsulfonyl)diazomethane, bis(cyclohexylsulfonyl)diazomethane and bis(2,4-dimethylphenylsulfonyl)diazomethane; nitrobenzyl derivatives such as 2-nitrobenzyl p-toluenesulfonate, 2,6-dinitrobenzyl p-toluenesulfonate, nitrobenzyl tosylate, dinitrobenzyl tosylate, nitrobenzyl sulfonate, nitrobenzyl carbonate and dinitrobenzyl carbonate; sulfonates such as pyrogalloltrimesylate, pyrogalloltritosylate, benzyltosylate, benzylsulfonate, N-methylsulfonyloxysuccinimide, N-trichloromethylsulfonyloxysuccinimide, N-phenylsulfonyloxymaleimide and N-methylsulfonyloxyphthalimide; trifluoromethane sulfonates such as N-(trifluoromethylsulfonyloxy)phthalimide, N-(trifluoromethylsulfonyloxy)-1,8-naphthalimide and N-(trifluoromethylsulfonyloxy)-4-butyl-1,8-naphthalimide; onium salts such as diphenyliodonium hexafluorophosphate, (4-methoxyphenyl)phenyliodonium trifluoromethanesulfonate, bis(p-tert-butylphenyl)iodonium trifluoromethanesulfonate, triphenylsulfonium hexafluorophosphate, (4-methoxyphenyl)diphenylsulfonium trifluoromethanesulfonate and (p-tert-butylphenyl)diphenylsulfonium trifluoromethanesulfonate; benzointosylates such as benzointosylate and α-methylbenzointosylate; other diphenyliodonium salts, triphenylsulfonium salts, phenyldiazonium salts, benzylcarbonates and the like.

This acid generator (A) may be used alone, or two or more types may be used in combination. Furthermore, the content of the acid generator (A) is adjusted to preferably 0.1% by mass or more and 10% by mass or less, more preferably 0.2% by mass or more and 6% by mass or less, and particularly preferably 0.5% by mass or more and 3% by mass or less, relative to the total mass of the solid component of the positive-type photosensitive composition. When the amount of the acid generator (A) used is adjusted to the range mentioned above, it is easy to prepare a positive-type photosensitive composition which is a uniform solution having satisfactory sensitivity and excellent storage stability.

<Resin (B)>

A resin (B) whose solubility in alkali increases under the action of acid is not particularly limited any resins whose solubility in alkali increases under the action of acid can be used. Among them, it is preferable to contain at least one resin selected from the group consisting of a novolac resin (B1), a polyhydroxystyrene resin (B2), and an acrylic resin (B3).

[Novolac Resin (B1)]

As the novolak resin (B1), a resin including the constituent unit represented by the following formula (b1) may be used.

[Chem. 18]

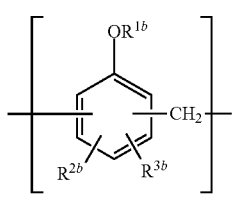
(b1)

In the formula (b1), $R^{1b}$ represents an acid-dissociable dissolution-inhibiting group, and $R^{2b}$ and $R^{3b}$ each independently represent a hydrogen atom or an alkyl group having 1 or more and 6 or less carbon atoms.

The acid-dissociable dissolution-inhibiting group represented by the above $R^{1b}$ is preferably a group represented by the following formula (b2) or (b3), a linear, branched or cyclic alkyl group having 1 or more and 6 or less carbon atoms, a vinyloxyethyl group, a tetrahydropyranyl group, a tetrahydrofuranyl group, or a trialkylsilyl group.

[Chem. 19]

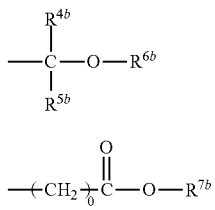
(b2)

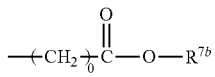
(b3)

In the above formulae (b2) and (b3), $R^{4b}$ and $R^{5b}$ each independently represent a hydrogen atom, or a linear or branched alkyl group having 1 or more and 6 or less carbon atoms, $R^{6b}$ represents a linear, branched or cyclic alkyl group having 1 or more and 10 or less carbon atoms, $R^{7b}$ represents a linear, branched or cyclic alkyl group having 1 or more and 6 or less carbon atoms, and o represents 0 or 1.

Examples of the above linear or branched alkyl group include a methyl group, an ethyl group, a propyl group, an isopropyl group, an n-butyl group, an isobutyl group, a tert-butyl group, a pentyl group, an isopentyl group, a neopentyl group, and the like. Also, examples of the above cyclic alkyl group include a cyclopentyl group, a cyclohexyl group, and the like.

Specific examples of the acid-dissociable dissolution-inhibiting group represented by the above formula (b2) include a methoxyethyl group, ethoxyethyl group, n-propoxyethyl group, isopropoxyethyl group, n-butoxyethyl group, isobutoxyethyl group, tert-butoxyethyl group, cyclohexyloxyethyl group, methoxypropyl group, ethoxypropyl group, 1-methoxy-1-methyl-ethyl group, 1-ethoxy-1-methylethyl group, and the like. Furthermore, specific examples of the acid-dissociable dissolution-inhibiting group represented by the above formula (b3) include a tert-butoxycarbonyl group, a tert-butoxycarbonylmethyl group, and the like. Examples of the above trialkylsilyl group include a trimethylsilyl group and tri-tert-butyldimethylsilyl group in which each alkyl group has 1 or more and 6 or less carbon atoms.

[Polyhydroxystyrene Resin (B2)]

As the polyhydroxystyrene resin (B2), a resin including a constituent unit represented by the following formula (b4) may be used.

[Chem. 20]

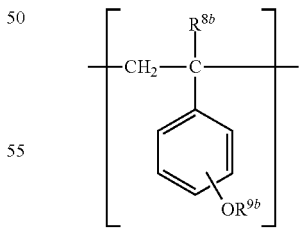
(b4)

In the above formula (b4), $R^{8b}$ represents a hydrogen atom or an alkyl group having 1 or more and 6 or less carbon atoms, and $R^{9b}$ represents an acid-dissociable dissolution-inhibiting group.

The above alkyl group having 1 or more and 6 or less carbon atoms may include, for example, linear, branched or cyclic alkyl groups having 1 or more and 6 or less carbon atoms. Examples of the linear or branched alkyl group include a methyl group, ethyl group, propyl group, isopropyl group, n-butyl group, isobutyl group, tert-butyl group, pentyl group, isopentyl group, neopentyl group, and the like. Examples of the cyclic alkyl group include a cyclopentyl group and cyclohexyl group.

The acid-dissociable dissolution-inhibiting group represented by the above $R^{9b}$ may be similar to those exemplified in terms of the above formulae (b2) and (b3).

Furthermore, the polyhydroxystyrene resin (B2) may include another polymerizable compound as a constituent unit in order to moderately control physical or chemical properties. The polymerizable compound is exemplified by conventional radical polymerizable compounds and anion polymerizable compounds. Examples of the polymerizable compound include monocarboxylic acids such as acrylic acid, methacrylic acid and crotonic acid; dicarboxylic acids such as maleic acid, fumaric acid and itaconic acid; methacrylic acid derivatives having a carboxyl group and an ester bond such as 2-methacryloyloxyethyl succinic acid, 2-methacryloyloxyethyl maleic acid, 2-methacryloyloxyethyl phthalic acid and 2-methacryloyloxyethyl hexahydrophthalic acid; (meth)acrylic acid alkyl esters such as methyl (meth)acrylate, ethyl (meth)acrylate and butyl (meth)acrylate; (meth)acrylic acid hydroxyalkyl esters such as 2-hydroxyethyl (meth)acrylate and 2-hydroxypropyl (meth)acrylate; (meth)acrylic acid aryl esters such as phenyl (meth)acrylate and benzyl (meth)acrylate; dicarboxylic acid diesters such as diethyl maleate and dibutyl fumarate; vinyl group-containing aromatic compounds such as styrene, α-methylstyrene, chlorostyrene, chloromethylstyrene, vinyltoluene, hydroxystyrene, α-methylhydroxystyrene and α-ethylhydroxystyrene; vinyl group-containing aliphatic compounds such as vinyl acetate; conjugated diolefins such as butadiene and isoprene; nitrile group-containing polymerizable compounds such as acrylonitrile and methacrylonitrile; chlorine-containing polymerizable compounds such as vinyl chloride and vinylidene chloride; and amide bond-containing polymerizable compounds such as acrylamide and methacrylamide.

[Acrylic Resin (B3)]

An acrylic resin (B3) is not particularly limited as long as it is an acrylic resin the solubility of which in alkali increases under the action of acid, and has conventionally blended in various photosensitive compositions. Preferably, the acrylic resin (B3) contains a constituent unit (b-3) derived from, for example, an acrylic ester including an —$SO_2$-containing cyclic group or a lactone-containing cyclic group. In such a case, when a resist pattern is formed, a resist pattern having a preferable cross-sectional shape can be easily formed.

(—$SO_2$-Containing Cyclic Group)

Herein, the "—$SO_2$-containing cyclic group" refers to a cyclic group having a cyclic group containing a ring including —$SO_2$— in the ring skeleton thereof, specifically a cyclic group in which the sulfur atom (S) in —$SO_2$— forms a part of the ring skeleton of the cyclic group. Considering a ring including —$SO_2$— in the ring skeleton thereof as the first ring, a group having that ring alone is called a monocyclic group, and a group further having another ring structure is called a polycyclic group regardless of its structure. The —$SO_2$-containing cyclic group may be monocyclic or polycyclic.

In particular, the —$SO_2$-containing cyclic group is preferably a cyclic group containing —O—$SO_2$— in the ring skeleton thereof, i.e., a cyclic group containing a sultone ring in which —O—S— in —O—$SO_2$— forms a part of the ring skeleton.

The number of carbon atoms in an —$SO_2$-containing cyclic group is preferably 3 or more and 30 or less, more preferably 4 or more and 20 or less, even more preferably 4 or more and 15 or less, and in particular preferably 4 or more and 12 or less. The above number of carbon atoms is the number of carbon atoms constituting a ring skeleton, and shall not include the number of carbon atoms in a substituent.

The —$SO_2$-containing cyclic group may be an —$SO_2$-containing aliphatic cyclic group or an —$SO_2$-containing aromatic cyclic group. It is preferably an —$SO_2$-containing aliphatic cyclic group.

—$SO_2$— containing aliphatic cyclic groups include a group in which at least one hydrogen atom is removed from an aliphatic hydrocarbon ring where a part of the carbon atoms constituting the ring skeleton thereof is(are) substituted with —$SO_2$— or —O—$SO_2$—. More specifically, they include a group in which at least one hydrogen atom is removed from an aliphatic hydrocarbon ring where —$CH_2$— constituting the ring skeleton thereof is substituted with —$SO_2$— and a group in which at least one hydrogen atom is removed from an aliphatic hydrocarbon ring where —$CH_2$—$CH_2$— constituting the ring thereof is substituted with —O—$SO_2$—.

The number of carbon atoms in the above alicyclic hydrocarbon ring is preferably 3 or more and 20 or less, more preferably 3 or more and 12 or less. The above alicyclic hydrocarbon ring may be polycyclic, or may be monocyclic. As the monocyclic alicyclic hydrocarbon group, preferred is a group in which two hydrogen atoms are removed from monocycloalkane having 3 or more and 6 or less carbon atoms. Examples of the above monocycloalkane can include cyclopentane, cyclohexane and the like. As the polycyclic alicyclic hydrocarbon ring, preferred is a group in which two hydrogen atoms are removed from polycycloalkane having 7 or more and 12 or less carbon atoms, and specific examples of the above polycycloalkane include adamantane, norbornane, isobornane, tricyclodecane, tetracyclododecane and the like.

The —$SO_2$-containing cyclic group may have a substituent. Examples of the above substituent include, for example, an alkyl group, an alkoxy group, a halogen atom, a halogenated alkyl group, a hydroxyl group, an oxygen atom (=O), —COOR'', OC(=O)R'', a hydroxyalkyl group, a cyano group and the like.

For an alkyl group as the above substituent, preferred is an alkyl group having 1 or more and 6 or less carbon atoms. The above alkyl group is preferably linear or branched. Specific examples include a methyl group, an ethyl group, an n-propyl group, an isopropyl group, an n-butyl group, an isobutyl group, a tert-butyl group, an n-pentyl group, an isopentyl group, a neopentyl group, an n-hexyl group and the like. Among these, a methyl group or an ethyl group is preferred, and a methyl group is particularly preferred.

For an alkoxy group as the above substituent, preferred is an alkoxy group having 1 or more and 6 or less carbon atoms. The above alkoxy group is preferably linear or branched. Specific examples include a group in which an alkyl groups recited as an alkyl group for the above substituent is attached to the oxygen atom (—O—).

Halogen atoms as the above substituent include a fluorine atom, a chlorine atom, a bromine atom, an iodine atom and the like, and a fluorine atom is preferred.

Halogenated alkyl groups for the above substituent include a group in which a part or all of the hydrogen atoms in the above alkyl group is(are) substituted with the above halogen atom(s).

Halogenated alkyl groups as the above substituent include a group in which a part or all of the hydrogen atoms in the alkyl groups recited as an alkyl group for the above substituent is(are) substituted with the above halogen atom(s). As the above halogenated alkyl group, a fluorinated alkyl group is preferred, and a perfluoroalkyl group is particularly preferred.

R"s in the aforementioned —COOR" and —OC(=O)R" are either a hydrogen atom or a linear, branched or cyclic alkyl group having 1 or more and 15 or less carbon atoms.

In a case where R" is a linear or branched alkyl group, the number of carbon atoms in the above chain alkyl group is preferably 1 or more and 10 or less, more preferably 1 or more and 5 or less, and in particular preferably 1 or 2.

In a case where R" is a cyclic alkyl group, the number of carbon atoms in the above cyclic alkyl group is preferably 3 or more and 15 or less, more preferably 4 or more and 12 or less, and in particular preferably 5 or more and 10 or less. Specific examples can include a group in which one or more hydrogen atoms are removed from monocycloalkane; and polycycloalkane such as bicycloalkane, tricycloalkane, tetracycloalkane and the like optionally substituted with a fluorine atom or a fluorinated alkyl group. More specific examples include a group in which one or more hydrogen atoms are removed from monocycloalkane such as cyclopentane and cyclohexane; and polycycloalkane such as adamantane, norbornane, isobornane, tricyclodecane and tetracyclododecane.

For a hydroxyalkyl group as the above substituent, preferred is a hydroxyalkyl group having 1 or more and 6 or less carbon atoms. Specific examples include a group in which at least one of the hydrogen atoms in the alkyl groups recited as an alkyl group for the above substituent is substituted with a hydroxyl group.

More specific examples of the —SO$_2$-containing cyclic group include the groups represented by the following formulae (3-1) to (3-4).

[Chem. 21]

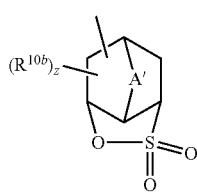

(3-1)

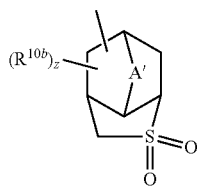

(3-2)

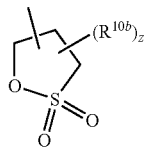

(3-3)

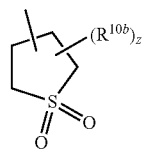

(3-4)

(In the formulae, A' represents an alkylene group having 1 or more and 5 or less carbon atoms optionally including an oxygen atom or a sulfur atom, an oxygen atom or a sulfur atom; z represents an integer of 0 or more and 2 or less; $R^{10b}$ represents an alkyl group, an alkoxy group, a halogenated alkyl group, a hydroxyl group, —COOR", —OC(=O)R", a hydroxyalkyl group, or a cyano group; and R" represents a hydrogen atom or an alkyl group.)

In the above formulae (3-1) to (3-4), A' represents an alkylene group having 1 or more and 5 or less carbon atoms optionally including an oxygen atom (—O—) or a sulfur atom (—S—), an oxygen atom or a sulfur atom. As an alkylene group having 1 or more and 5 or less carbon atoms in A', a linear or branched alkylene group is preferred, and examples thereof include a methylene group, an ethylene group, an n-propylene group, an isopropylene group and the like.

In a case where the above alkylene group includes an oxygen atom or a sulfur atom, specific examples thereof include a group in which —O— or —S— is present at a terminal or between carbon atoms of the above alkylene group, for example, —O—CH$_2$—, —CH$_2$—O—CH$_2$—, —S—CH$_2$—, —CH$_2$—S—CH$_2$—, and the like. As A', an alkylene group having 1 or more and 5 or less carbon atoms or —O— is preferred, and an alkylene group having 1 or more and 5 or less carbon atoms is more preferred, and a methylene group is most preferred.

z may be any of 0, 1, and 2, and is most preferably 0. In a case where z is 2, a plurality of $R^{10b}$ may be the same, or may differ from each other.

An alkyl group, an alkoxy group, an halogenated alkyl group, —COOR", —OC(=O)R" and a hydroxyalkyl group in $R^{10b}$ include those similar to the groups described above for the alkyl group, the alkoxy group, the halogenated alkyl group, —COOR", —OC(=O)R" and the hydroxyalkyl group, respectively, which are recited as those optionally contained in the —SO$_2$-containing cyclic group.

Below, specific cyclic groups represented by the above formulae (3-1) to (3-4) will be illustrated. Note here that "Ac" in the formulae represents an acetyl group.

[Chem. 22]

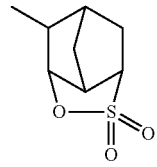

(3-1-1)

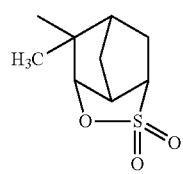

(3-1-2)

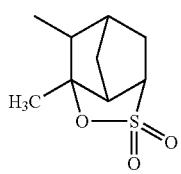 (3-1-3)
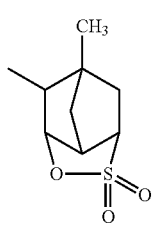 (3-1-4)
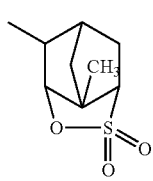 (3-1-5)
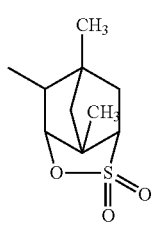 (3-1-6)
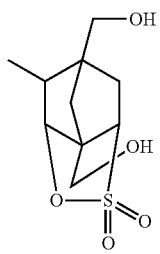 (3-1-7)
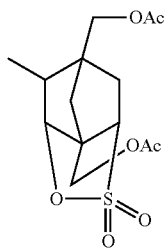 (3-1-8)
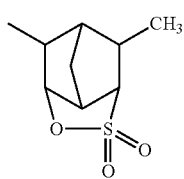 (3-1-9)
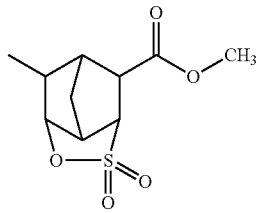 (3-1-10)
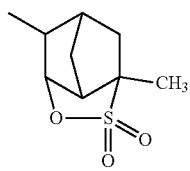 (3-1-11)
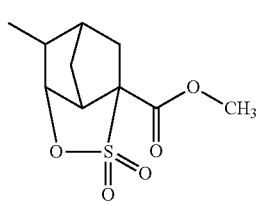 (3-1-12)
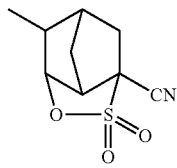 (3-1-13)
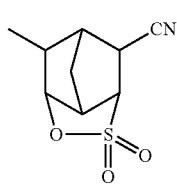 (3-1-14)
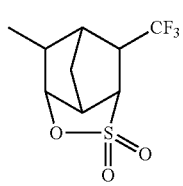 (3-1-15)
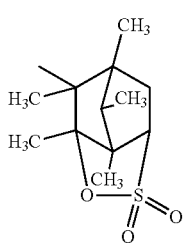 (3-1-16)
(3-1-17)

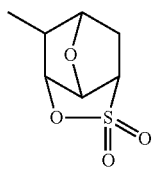
(3-1-18)
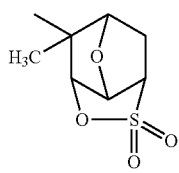
(3-1-19)
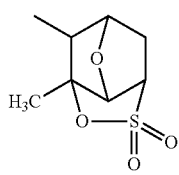
(3-1-20)
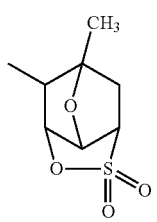
(3-1-21)
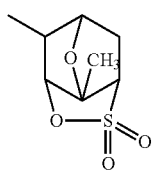
(3-1-22)
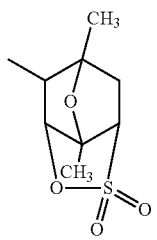
(3-1-23)
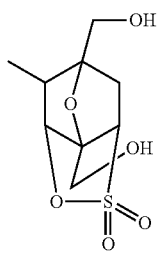
(3-1-24)
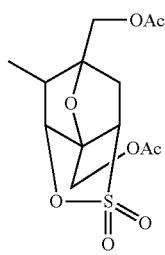
(3-1-25)
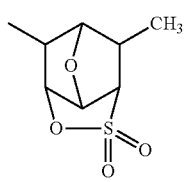
(3-1-26)
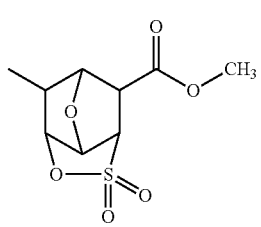
(3-1-27)
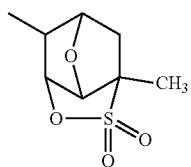
(3-1-28)
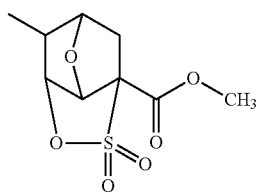
(3-1-29)
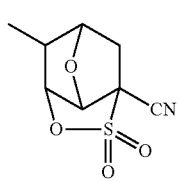
(3-1-30)
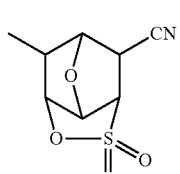
(3-1-31)
(3-1-32)

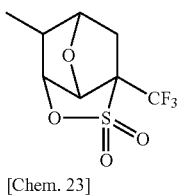
(3-1-33)

[Chem. 23]

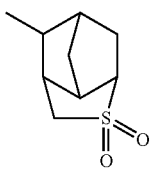
(3-2-1)

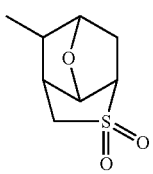
(3-2-2)

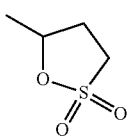
(3-3-1)

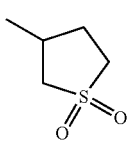
(3-4-1)

As the —SO$_2$-containing cyclic group, among those shown above, a group represented by the above formula (3-1) is preferred, and at least one selected from the group consisting of the groups represented by any of the aforementioned formulae (3-1-1), (3-1-18), (3-3-1) and (3-4-1) is more preferred, and a group represented by the aforementioned formula (3-1-1) is most preferred.

(Lactone-Containing Cyclic Group)

The "lactone-containing cyclic group" refers to a cyclic group containing a ring (lactone ring) including —O—C(=O)— in the ring skeleton thereof. Considering the lactone ring as the first ring, a group having that lactone ring alone is called a monocyclic group, and a group further having another ring structure is called a polycyclic group regardless of its structure. The lactone-containing cyclic group may be a monocyclic group, or may be a polycyclic group.

There is no particular limitation on the lactone cyclic group in the constituent unit (b-3), and any cyclic group can be used. Specifically, examples of the lactone-containing monocyclic groups include a group in which one hydrogen atom is removed from 4 to 6 membered ring lactone, for example, a group in which one hydrogen atom is removed from β-propiono lactone, a group in which one hydrogen atom is removed from γ-butyrolactone, a group in which one hydrogen atom is removed from δ-valerolactone and the like. Further, lactone-containing polycyclic groups include a group in which one hydrogen atom is removed from bicycloalkane, tricycloalkane and tetracycloalkane having a lactone ring.

As to the constituent unit (b-3), as long as the constituent unit (b-3) has an —SO2-containing cyclic group or a lactone-containing cyclic group, the structures of other parts are not particularly limited. A preferred constituent unit (b-3) is at least one constituent unit selected from the group consisting of a constituent unit (b-3-S) derived from an acrylic acid ester including an —SO$_2$-containing cyclic group in which a hydrogen atom attached to the carbon atom in the α position may be substituted with a substituent; and a constituent unit (b-3-L) derived from an acrylic acid ester including a lactone-containing cyclic group in which the hydrogen atom attached to the carbon atom in the α position may be substituted with a substituent.

[Constituent Unit (b-3-S)]

More specifically, examples of the constituent unit (b-3-S) include one represented by the following formula (b-S1).

[Chem. 24]

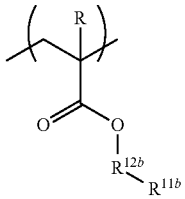
(b-S1)

(In the formula, R represents a hydrogen atom, an alkyl group having 1 or more 5 or less carbon atoms or a halogenated alkyl group having 1 or more 5 or less carbon atoms; and $R^{11b}$ represents an —SO$_2$-containing cyclic group; and $R^{12b}$ represents a single-bond or divalent linking group.)

In the formula (b-S1), R is similarly defined as above. $R^{11b}$ is similarly defined as in the —SO$_2$-containing cyclic group described above. $R^{12b}$ may be either a single-bond linking group or a divalent linking group.

There is no particular limitation on the divalent linking group in $R^{12b}$, and suitable groups include an optionally substituted divalent hydrocarbon group, a divalent linking group including a heteroatom, and the like.

—Optionally Substituted Divalent Hydrocarbon Group

The hydrocarbon group as a divalent linking group may be an aliphatic hydrocarbon group, or may be an aromatic hydrocarbon group. The aliphatic hydrocarbon group means a hydrocarbon group without aromaticity. The above aliphatic hydrocarbon group may be saturated or may be unsaturated. Usually, a saturated hydrocarbon group is preferred. More specifically, examples of the above aliphatic hydrocarbon group include a linear or branched aliphatic hydrocarbon group, an aliphatic hydrocarbon group including a ring in the structure thereof and the like.

The number of carbon atoms in the linear or branched aliphatic hydrocarbon group is preferably 1 or more and 10 or less, more preferably 1 or more and 8 or less, and even more preferably 1 or more and 5 or less.

As the linear aliphatic hydrocarbon group, a linear alkylene group is preferred. Specific examples include a methylene group [—CH$_2$—], an ethylene group [—(CH$_2$)$_2$—], a trimethylene group [—(CH$_2$)$_3$—], a tetramethylene group [—(CH$_2$)$_4$—], a pentamethylene group [—(CH$_2$)$_5$-] and the like.

As the branched aliphatic hydrocarbon group, a branched alkylene group is preferred. Specific examples include alkyl alkylene groups such as alkyl methylene groups such as —CH(CH₃)—, —CH(CH₂CH₃)—, —C(CH₃)₂—, —C(CH₃) (CH₂CH₃)—, —C(CH₃) (CH₂CH₂CH₃)— and —C(CH₂CH₃)₂—; alkyl ethylene groups such as —CH(CH₃)CH₂—, —CH(CH₃)CH(CH₃)—, —C(CH₃)₂CH₂—, —CH(CH₂CH₃)CH₂— and —C(CH₂CH₃)₂—CH₂—; alkyl trimethylene groups such as —CH(CH₃)CH₂CH₂— and —CH₂CH(CH₃)CH₂—; alkyl tetramethylene groups such as —CH(CH₃)CH₂CH₂CH₂— and —CH₂CH(CH₃)CH₂CH₂—; and the like. As an alkyl group in the alkyl alkylene group, a linear alkyl group having 1 or more and 5 or less carbon atoms is preferred.

The above linear or branched aliphatic hydrocarbon group may or may not have a substituent (a group or atom other than a hydrogen atom) which substitutes a hydrogen atom. Examples of the substituent include a fluorine atom, a fluorinated alkyl group having 1 or more and 5 or less carbon atoms substituted with a fluorine atom, an oxo group (=O) and the like.

Examples of the above aliphatic hydrocarbon group including a ring in the structure thereof include a cyclic aliphatic hydrocarbon group optionally including a hetero atom in the ring structure (a group in which two hydrogen atoms are removed from an aliphatic hydrocarbon ring); a group in which the above cyclic aliphatic hydrocarbon group is attached to an end of a linear or branched aliphatic hydrocarbon group; a group in which the above cyclic aliphatic hydrocarbon group is present in a linear or branched aliphatic hydrocarbon group along the chain; and the like. Examples of the above linear or branched aliphatic hydrocarbon group include those similar to the above.

The number of carbon atoms in the cyclic aliphatic hydrocarbon group is preferably 3 or more and 20 or less, and more preferably 3 or more and 12 or less.

The cyclic aliphatic hydrocarbon group may be polycyclic, or may be monocyclic. As the monocyclic aliphatic hydrocarbon group, a group in which two hydrogen atoms are removed from monocycloalkane is preferred. The number of carbon atoms in the above monocycloalkane is preferably 3 or more and 6 or less. Specific examples include cyclopentane, cyclohexane and the like. As the polycyclic aliphatic hydrocarbon group, a group in which two hydrogen atoms are removed from polycycloalkane is preferred. The number of carbon atoms in the above polycycloalkane is preferably 7 or more and 12 or less. Specific examples include adamantane, norbornane, isobornane, tricyclodecane, tetracyclododecane and the like.

The cyclic aliphatic hydrocarbon group may or may not have a substituent which substitutes a hydrogen atom (a group or atom other than a hydrogen atom). Examples of the above substituent include an alkyl group, an alkoxy group, a halogen atom, a halogenated alkyl group, a hydroxyl group, an oxo group (=O) and the like.

For an alkyl group as the above substituent, an alkyl group having 1 or more and 5 or less carbon atoms is preferred, and a methyl group, an ethyl group, a propyl group, an n-butyl group and a tert-butyl group are more preferred.

For an alkoxy group as the above substituent, an alkoxy group having 1 or more and 5 or less carbon atoms is preferred, and a methoxy group, an ethoxy group, an n-propoxy group, an iso-propoxy group, an n-butoxy group and a tert-butoxy group are more preferred, and a methoxy group and an ethoxy group are particularly preferred.

Halogen atoms as the above substituent include a fluorine atom, a chlorine atom, a bromine atom, an iodine atom and the like, and a fluorine atom is preferred.

Halogenated alkyl groups as the above substituent include a group in which a part or all of hydrogen atoms in the aforementioned alkyl group is(are) substituted with the above halogen atom(s).

In the cyclic aliphatic hydrocarbon group, a part of carbon atoms constituting the ring structure thereof may be substituted with —O—, or —S—. As the substituent including the above hetero atom, preferred are —O—, —C(=O)—O—, —S—, —S(=O)₂— and —S(=O)₂—O—.

The aromatic hydrocarbon group as the divalent hydrocarbon group is a divalent hydrocarbon group having at least one aromatic ring, and may have a substituent. There is no particular limitation on the aromatic ring as long as it is a cyclic conjugated system having a 4n+2 π electrons, and it may be monocyclic or may be polycyclic. The number of carbon atoms in the aromatic ring is preferably 5 or more and 30 or less, more preferably 5 or more and 20 or less, further more preferably 6 or more and 15 or less, and particularly preferably 6 or more and 12 or less. However, the number of carbon atoms in a substituent shall not be included in the above number of carbon atoms.

Specifically, aromatic rings include aromatic hydrocarbon rings such as benzene, naphthalene, anthracene and phenanthrene; aromatic heterocycles in which a part of the carbon atoms constituting the above aromatic hydrocarbon ring is(are) substituted with hetero atom(s). Hetero atoms in the aromatic heterocycle include an oxygen atom, a sulfur atom, a nitrogen atom and the like. Specifically, aromatic heterocycles include a pyridine ring, a thiophene ring, and the like.

Specific examples of the aromatic hydrocarbon group as a divalent hydrocarbon group include a group in which two hydrogen atoms are removed from the above aromatic hydrocarbon ring or the above aromatic heterocycle (an arylene group or a heteroarylene group); a group in which two hydrogen atoms are removed from an aromatic compound including two or more aromatic rings (for example, biphenyl, fluorene and the like); a group in which one hydrogen atom from a group where one hydrogen atom is removed from the above aromatic hydrocarbon ring or the above aromatic heterocycle (an aryl group or a heteroaryl group) is substituted with an alkylene group (for example, a group in which one hydrogen atom is further removed from an aryl group in an arylalkyl group such as a benzyl group, a phenethyl group, a 1-naphthylmethyl group, a 2-naphthylmethyl group, a 1-naphthylethyl group and a 2-naphthylethyl group); and the like.

The number of carbon atoms in the above alkylene group bonded to an aryl group or a heteroaryl group is preferably 1 or more and 4 or less, more preferably 1 or more and 2 or less, and particularly preferably 1.

In the above aromatic hydrocarbon group, a hydrogen atom of the above aromatic hydrocarbon group may be substituted with a substituent. For example, a hydrogen atom attached to an aromatic ring in the above aromatic hydrocarbon group may be substituted with a substituent. Examples of the substituent include an alkyl group, an alkoxy group, a halogen atom, a halogenated alkyl group, a hydroxyl group, an oxo group (=O) and the like.

For an alkyl group as the above substituent, an alkyl group having 1 or more and 5 or less carbon atoms is preferred, and a methyl group, an ethyl group, an n-propyl group, an n-butyl group and a tert-butyl group are more preferred.

For an alkoxy group as the above substituent, an alkoxy group having 1 or more and 5 or less carbon atoms is preferred, and a methoxy group, an ethoxy group, an n-propoxy group, an iso-propoxy group, an n-butoxy group and a tert-butoxy group are preferred, and a methoxy group and an ethoxy group are more preferred.

Halogen atoms as the above substituent include a fluorine atom, a chlorine atom, a bromine atom, an iodine atom and the like, and a fluorine atom is preferred.

Halogenated alkyl groups as the above substituent include a group in which a part or all of hydrogen atoms in the aforementioned alkyl group is(are) substituted with the above halogen atom(s).

Divalent Linking Group Including Hetero Atom

A hetero atom in the divalent linking group including a hetero atom is an atom other than a carbon atom and a hydrogen atom, and examples thereof include an oxygen atom, a nitrogen atom, a sulfur atom, a halogen atom and the like.

Specific examples of the divalent linking group including a hetero atom include non-hydrocarbon based linking groups such as —O—, —C(=O)—, —C(=O)—O—, —O—C(=O)—O—, —S—, —S(=O)$_2$—, —S(=O)$_2$—O—, —NH—, —NH—C(=O)—, —NH—C(=NH)—, =N—, and combinations of at least one of these non-hydrocarbon based linking groups and a divalent hydrocarbon group and the like. Examples of the above divalent hydrocarbon group include those similar to the aforementioned divalent hydrocarbon groups optionally having a substituent, and linear or branched aliphatic hydrocarbon groups are preferred.

Among those described above, H in —NH— in —C(=O)—NH—, —NH— and —NH—C(=NH)— may be substituted with a substituent such as an alkyl group or an acyl group, respectively. The number of carbon atoms in the above substituent is preferably 1 or more and 10 or less, more preferably 1 or more and 8 or less, and in particular preferably 1 or more and 5 or less.

As a divalent linking group in $R^{12b}$, a linear or branched alkylene group, a cyclic aliphatic hydrocarbon group, or a divalent linking group including a hetero atom is preferred.

In a case where the divalent linking group in $R^{12b}$ is a linear or branched alkylene group, the number of carbon atoms in the above alkylene group is preferably 1 or more and 10 or less, more preferably 1 or more and 6 or less, in particular preferably 1 or more and 4 or less, and most preferably 1 or more and 3 or less. Specific examples include groups similar to the linear alkylene groups or branched alkylene groups recited as a linear and branched aliphatic hydrocarbon group in the description of the "divalent hydrocarbon group optionally having a substituent" as the aforementioned divalent linking group.

In a case where the divalent linking group in $R^{12b}$ is a cyclic aliphatic hydrocarbon group, examples of the above cyclic aliphatic hydrocarbon group include groups similar to those recited as the "aliphatic hydrocarbon group including a ring in the structure" in the description of the "divalent hydrocarbon group optionally having a substituent" as the aforementioned divalent linking group.

As the above cyclic aliphatic hydrocarbon group, particularly preferred is a group in which two or more hydrogen atoms are removed from cyclopentane, cyclohexane, norbornane, isobornane, adamantane, tricyclodecane or tetracyclododecane.

In a case where the divalent linking group in $R^{12b}$ is a divalent linking group including a hetero atom, groups preferred as the above linking groups include —O—, —C(=O)—O—, —C(=O)—, —O—C(=O)—O—, —C(=O)—NH—, —NH— (H may be substituted with a substituent such as an alkyl group or an acyl group), —S—, —S(=O)$_2$—, —S(=O)$_2$—O— and a group represented by the general formula —Y—O—Y$^2$—, —[Y—C(=O)—O]$_{m'}$—Y$^2$— or —Y—O—C(=O)—Y$_2$-[wherein $Y^1$ and $Y^2$ are divalent hydrocarbon groups each independently, optionally having a substituent, and O represents an oxygen atom, and m' is an integer of 0 or more and 3 or less]

In a case where the divalent linking group in $R^{12b}$ is —NH—, the hydrogen atom in —NH— may be substituted with a substituent such as an alkyl group or an acyl group. The number of carbon atoms in the above substituent (an alkyl group, an acyl group and the like) is preferably 1 or more and 10 or less, more preferably 1 or more and 8 or less, and in particular preferably 1 or more and 5 or less.

$Y^1$ and $Y^2$ in the formula Y—O—Y$^2$—, —[Y$^1$—C(=O)—O]$_{m'}$—Y$^2$ or —Y$^1$—O—C(=O)—Y$^2$— are divalent hydrocarbon groups each independently, optionally having a substituent. Examples of the above divalent hydrocarbon group include groups similar to the "divalent hydrocarbon group optionally having a substituent" recited in the description of the above divalent linking group.

As $Y^1$, a linear aliphatic hydrocarbon group is preferred, and a linear alkylene group is more preferred, and a linear alkylene group having 1 or more and 5 or less carbon atoms is more preferred, and a methylene group and an ethylene group are particularly preferred.

As $Y^2$, a linear or branched aliphatic hydrocarbon group is preferred, and a methylene group, an ethylene group and an alkylmethylene group are more preferred. The alkyl group in the above alkylmethylene group is preferably a linear alkyl group having 1 or more and 5 or less carbon atoms, more preferably a linear alkyl group having 1 or more and 3 or less carbon atoms, and particularly preferably a methyl group.

In a group represented by the formula —[Y$^1$—C(=O)—O]$_{m'}$—Y$^2$—, m' is an integer of 0 or more and 3 or less, preferably an integer of 0 or more and 2 or less, more preferably 0 or 1, and particularly preferably 1. In other words, as a group represented by the formula —[Y$^1$—C(=O)—O]$_{m'}$—Y$^2$—, a group represented by the formula —Y$^1$—C(=O)—O—Y$^2$— is particularly preferred. Among these, a group represented by the formula —(CH$_2$)$_{a'}$—C(=O)—O—(CH$_2$)$_{b'}$— is preferred. In the above formula, a' is an integer of 1 or more and 10 or less, preferably an integer of 1 or more and 8 or less, more preferably an integer of 1 or more and 5 or less, even more preferably 1 or 2, and most preferably 1. b' is an integer of 1 or more and 10 or less, preferably an integer of 1 or more and 8 or less, more preferably an integer of 1 or more and 5 or less, even more preferably 1 or 2, and most preferably 1.

With regard to the divalent linking group in $R^{12b}$, an organic group including a combination of at least one non-hydrocarbon group and a divalent hydrocarbon group is preferred as the divalent linking group including a hetero atom. Among these, a linear chain group having an oxygen atom as a hetero atom, for example, a group including an ether bond or an ester bond is preferred, and a group represented by the aforementioned formula —Y$^1$—O—Y$^2$—, —[Y$^1$—C(=O)—O]$_{m'}$—Y$^2$— or —Y$^1$—O—C(=O)—Y$^2$— is more preferred, and a group represented by the aforementioned formula —[Y$^1$—C(=O)—O]$_{m'}$—Y$^2$— or —Y$^1$—O—C(=O)—Y$^2$— is particularly preferred.

As the divalent linking group in $R^{12b}$, a group including an alkylene group or an ester bond (—C(=O)—O—) is preferred.

The above alkylene group is preferably a linear or branched alkylene group. Suitable examples of the above linear aliphatic hydrocarbon group include a methylene group [—CH$_2$—], an ethylene group [—(CH$_2$)$_2$—], a trimethylene group [—(CH$_2$)$_3$—], a tetramethylene group

[—(CH$_2$)$_4$—], a pentamethylene group [—(CH$_2$)$_5$-] and the like. Suitable examples of the above branched alkylene group include alkyl alkylene groups such as alkyl methylene groups such as —CH(CH$_3$)—, —CH(CH$_2$CH$_3$)—, —C(CH$_3$)$_2$—, —C(CH$_3$) (CH$_2$CH$_3$)—, —C(CH$_3$) (CH$_2$CH$_2$CH$_3$)— and —C(CH$_2$CH$_3$)$_2$—; alkyl ethylene groups such as —CH(CH$_3$)CH$_2$—, —CH(CH$_3$)CH(CH$_3$)—, —C(CH$_3$)$_2$CH$_2$—, —CH(CH$_2$CH$_3$) CH$_2$— and —C(CH$_2$CH$_3$)$_2$—CH$_2$—; alkyl trimethylene groups such as —CH(CH$_3$)CH$_2$CH$_2$— and —CH$_2$CH(CH$_3$)CH$_2$—; alkyl tetramethylene groups such as —CH(CH$_3$)CH$_2$CH$_2$CH$_2$— and —CH$_2$CH(CH$_3$) CH$_2$CH$_2$—.

As the divalent linking group including an ester bond, particularly preferred is a group represented by the formula: —R$^{13b}$—C(=O)—O—[wherein R$^{13b}$ represents a divalent linking group.]. In other words, the constituent unit (b-3-S) is preferably a constituent unit represented by the following formula (b-S1-1).

[Chem. 25]

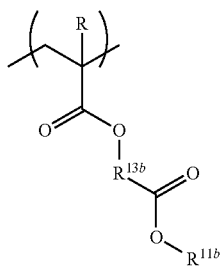

(b-S1-1)

(In the formula, R and R$^{11b}$ are each similar to the above, and R$^{13b}$ represents a divalent linking group.)

There is no particular limitation for R$^{13b}$, examples thereof include groups similar to the aforementioned divalent linking group in R$^{12b}$. As the divalent linking group in R$^{13b}$, a linear or branched alkylene group, an aliphatic hydrocarbon group including a ring in the structure, or a divalent linking group including a hetero atom is preferred, and a linear or branched alkylene group or a divalent linking group including an oxygen atom as a hetero atom is preferred.

As the linear alkylene group, a methylene group or an ethylene group is preferred, and a methylene group is particularly preferred. As the branched alkylene group, an alkylmethylene group or an alkylethylene group is preferred, and —CH(CH$_3$)—, —C(CH$_3$)$_2$— or —C(CH$_3$)$_2$CH$_2$— is particularly preferred.

As the divalent linking group including an oxygen atom, a divalent linking group including an ether bond or an ester bond is preferred, and the aforementioned —Y$^1$—O—Y$^2$—, —[Y$^1$—C(=O)—O]$_{m'}$—Y$^2$— or —Y$^1$—O—C(=O)—Y$^2$— is more preferred. Y$^1$ and Y$^2$ are each independently divalent hydrocarbon groups optionally having a substituent, and m' is an integer of 0 or more and 3 or less. Among these, —Y$^1$—O—C(=O)—Y$^2$— is preferred, and a group represented by —(CH$_2$)$_c$—O—C(=O)—(CH$_2$)$_d$— is particularly preferred. c is an integer of 1 or more and 5 or less, and 1 or 2 is preferred. d is an integer of 1 or more and 5 or less, and 1 or 2 is preferred.

As the constituent unit (b-3-S), in particular, one represented by the following formula (b-S1-11) or (b-S1-12) is preferred, and one represented by the formula (b-S1-12) is more preferred.

[Chem. 26]

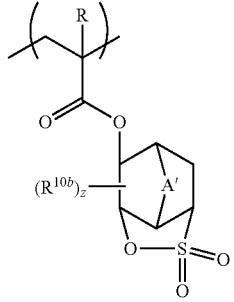

(b-S1-11)

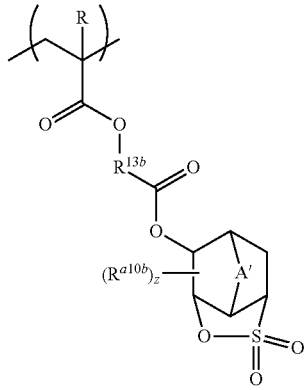

(b-S1-12)

(In the formulae, R, A', R$^{10b}$, z and R$^{13b}$ are each the same as the above.)

In the formula (b-S1-11), A' is preferably a methylene group, an oxygen atom (—O—) or a sulfur atom (—S—).

As R$^{13b}$, preferred is a linear or branched alkylene group or a divalent linking group including an oxygen atom. Examples of the linear or branched alkylene group and the divalent linking group including an oxygen atom in R$^{13b}$ include those similar to the aforementioned linear or branched alkylene group and the aforementioned divalent linking group including an oxygen atom, respectively.

As the constituent unit represented by the formula (b-S1-12), particularly preferred is one represented by the following formula (b-S1-12a) or (b-S1-12b).

[Chem. 27]

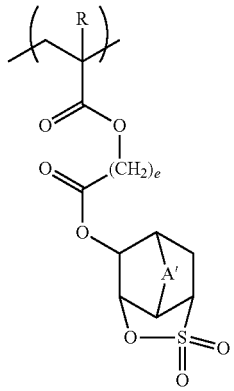

(b-S1-12a)

-continued (b-S1-12b)

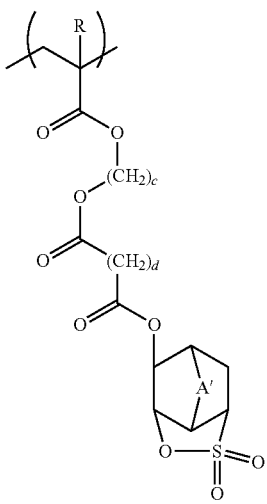

(In the formulae, R and A' are each the same as the above, and c to e are each independently an integer of 1 or more and 3 or less.)

[Constituent Unit (b-3-L)]

Examples of the constituent unit (b-3-L) include, for example, a constituent unit in which $R^{11b}$ in the aforementioned formula (b-S1) is substituted with a lactone-containing cyclic group. More specifically they include those represented by the following formulae (b-L1) to (b-L5).

[Chem. 28]

(b-L1)

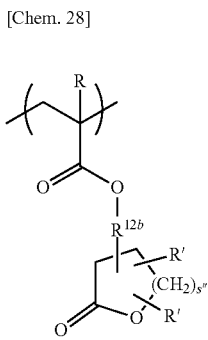

(b-L2)

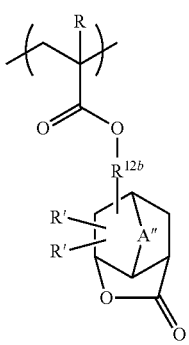

(b-L3)

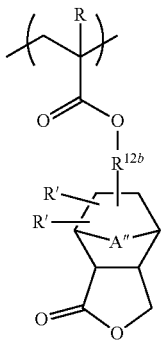

(b-L4)

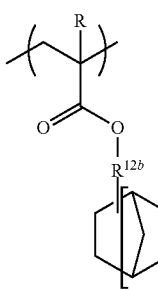

(b-L5)

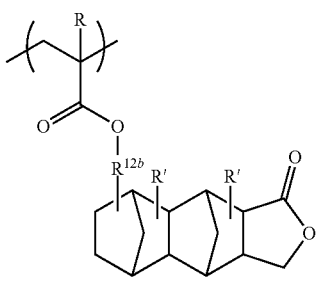

(In the formulae, R represents a hydrogen atom, an alkyl group having 1 or more and 5 or less carbon atoms or a halogenated alkyl group having 1 or more and 5 or less carbon atoms; R' represents each independently a hydrogen atom, an alkyl group, an alkoxy group, a halogenated alkyl group, a hydroxyl group, —COOR", —OC(=O)R", a hydroxyalkyl group or a cyano group, and R" represents a hydrogen atom or an alkyl group; $R^{12b}$ represents a single bond or divalent linking group, and s" is an integer of 0 or more and 2 or less; A" represents an alkylene group having 1 or more and 5 or less carbon atoms optionally including an oxygen atom or a sulfur atom, an oxygen atom or a sulfur atom; and r is 0 or 1.)

R in the formulae (b-L1) to (b-L5) is the same as the above. Examples of the alkyl group, the alkoxy group, the halogenated alkyl group, —COOR", —OC(=O)R" and the hydroxyalkyl group in R' include groups similar to those described for the alkyl group, the alkoxy group, the halogenated alkyl group, —COOR", —OC(=O)R" and the hydroxyalkyl group recited as a substituent which the —SO$_2$-containing cyclic group may have, respectively.

R' is preferably a hydrogen atom in view of easy industrial availability and the like. The alkyl group in R" may be any of a linear, branched or cyclic chain. In a case where R" is a linear or branched alkyl group, the number of carbon atoms is preferably 1 or more and 10 or less, and more preferably 1 or more and 5 or less. In a case where R" is a cyclic alkyl group, the number of carbon atoms is preferably 3 or more and 15 or less, more preferably 4 or more and 12 or less, and most preferably 5 or more and 10 or less. Specific examples include a group in which one or more hydrogen atoms are removed from monocycloalkane and polycycloalkane such as bicycloalkane, tricycloalkane, tetracycloalkane and the like optionally substituted with a fluorine atom or a fluorinated alkyl group. Specific examples include a group in which one or more hydrogen atoms are removed from monocycloalkane such as cyclopentane and cyclohexane; and polycycloalkane such as adamantane, norbornane, isobornane, tricyclodecane and tetracyclododecane; and the like. Examples of A″ include groups similar to A′ in the aforementioned formula (3-1). A″ is preferably an alkylene group having 1 to 5 carbon atoms, an oxygen atom (—O—) or a sulfur atom (—S—), more preferably an alkylene group having 1 or more and 5 or less carbon atoms or —O—. As the alkylene group having 1 or more and 5 or less carbon atoms, a methylene group or a dimethylmethylene group is more preferred, and a methylene group is most preferred.

$R^{12b}$ is similar to $R^{12b}$ in the aforementioned formula (b-S1). In the formula (b-L1), s″ is preferably 1 or 2. Below, specific examples of the constituent units represented by the aforementioned formulae (b-L1) to (b-L3) will be illustrated. In each of the following formulae, $R^\alpha$ represents a hydrogen atom, a methyl group or a trifluoromethyl group.

[Chem. 29]

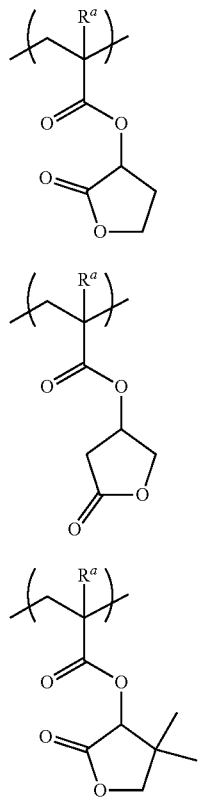
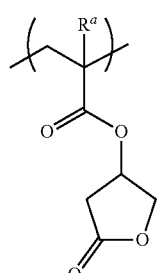
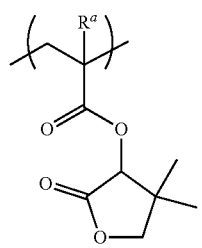

(b-L1-1)

(b-L1-2)

(b-L1-3)

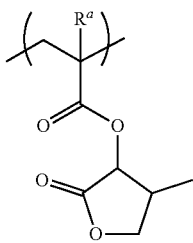

(b-L1-4)

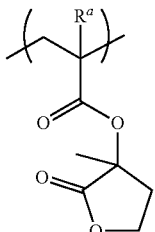

(b-L1-5)

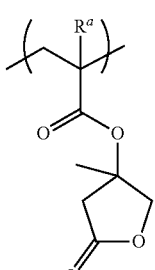

(b-L1-6)

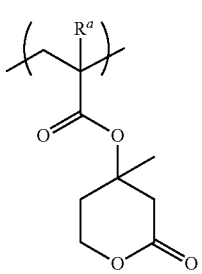

(b-L1-7)

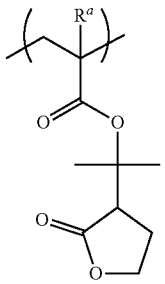

(b-L1-8)

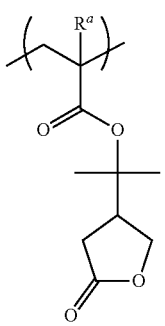

(b-L1-9)

(b-L1-10)
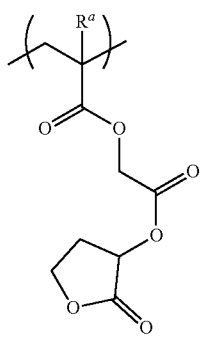
(b-L1-11)
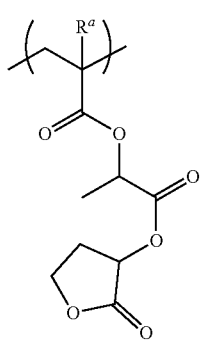
(b-L1-12)
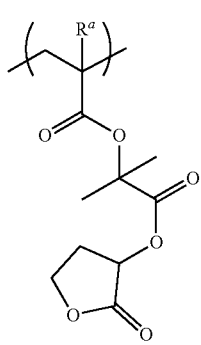
(b-L1-13)
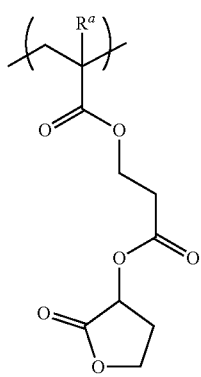
[Chem. 30]
(b-L2-1)
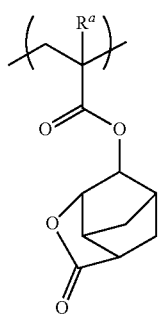
(b-L2-2)
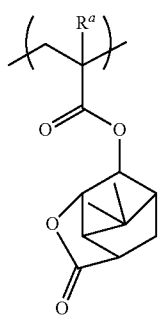
(b-L2-3)
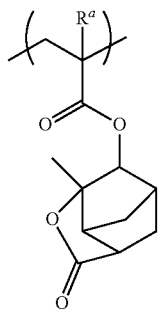
(b-L2-4)
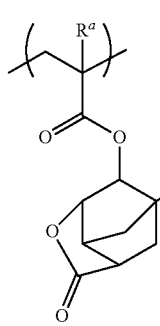
(b-L2-5)
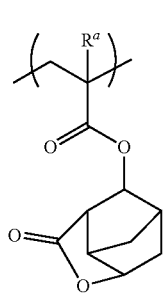

(b-L2-6)
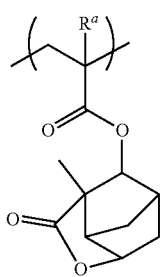
(b-L2-7)
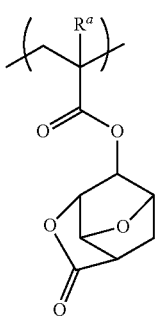
(b-L2-8)
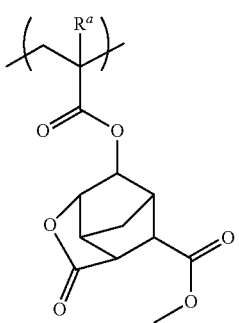
(b-L2-9)
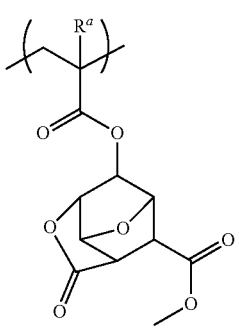
(b-L2-10)
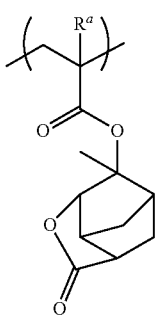
(b-L2-11)
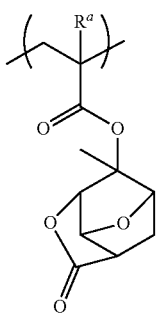
(b-L2-12)
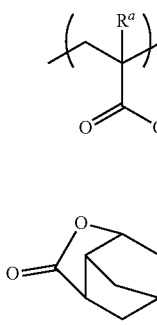
(b-L2-13)
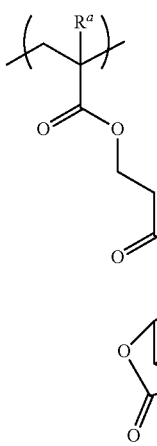
(b-L2-14)
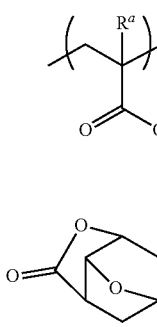

(b-L2-15)
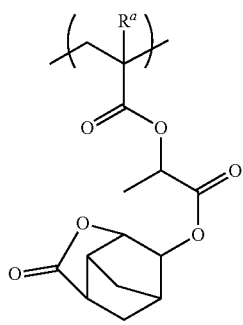

(b-L2-16)
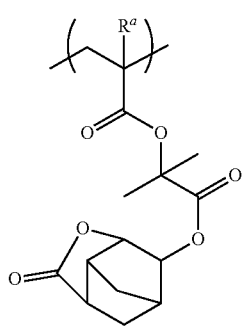

(b-L2-17)
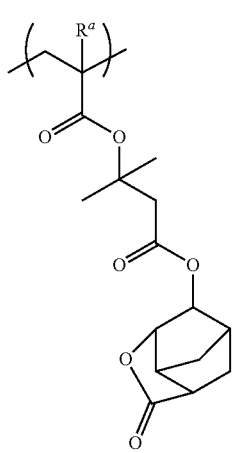

[Chem. 31]

(b-L3-1)
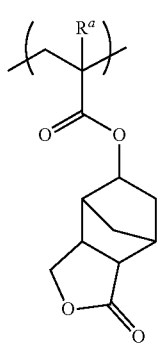

(b-L3-2)
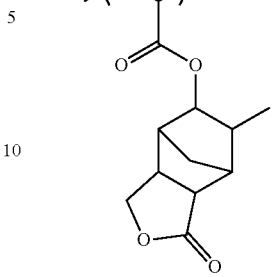

(b-L3-3)
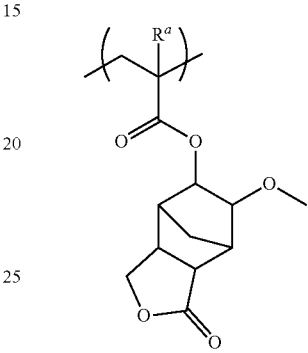

b-L3-4)

(b-L3-5)
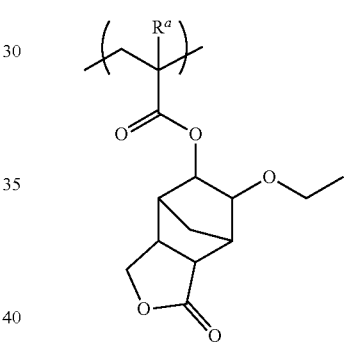

As the constituent unit (b-3a-L), at least one selected from the group consisting of the constituent units represented by the aforementioned formulae (b-L1) to (b-L5) is preferred, and at least one selected from the group consisting of the constituent units represented by the formulae (b-L1) to (b-L3) is more preferred, and at least one selected from the group consisting of the constituent units represented by the aforementioned formula (b-L1) or (b-L3) is particularly preferred. Among these, at least one selected from the group consisting of the constituent units represented by the aforementioned formulae (b-L1-1), (b-L1-2), (b-L2-1), (b-L2-7), (b-L2-12), (b-L2-14), (b-L3-1) and (b-L3-5) is preferred.

Further, as the constituent unit (b-3-L), the constituent units represented by following formulae (b-L6) to (b-L7) are also preferred.

[Chem. 32]

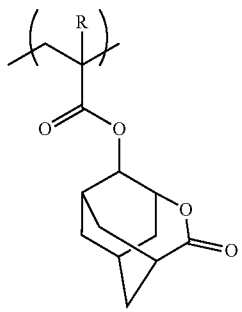

(b-L6)

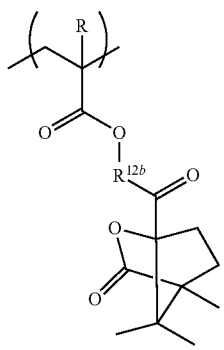

(b-L7)

R and $R^{12b}$ in the formulae (b-L6) and (b-L7) are the same as the above.

Further, the acrylic resin (B3) includes constituent units represented by the following formulae (b5) to (b7), having an acid dissociable group, as constituent units that enhance the solubility of the acrylic resin (B3) in alkali under the action of acid.

[Chem. 33]

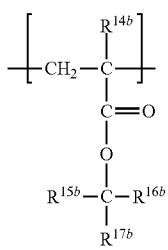

(b5)

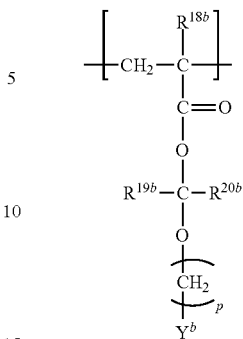

(b6)

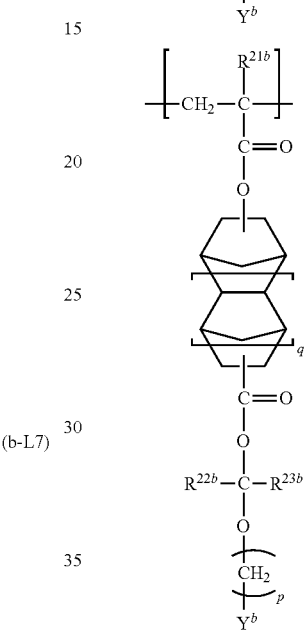

(b7)

In the above formulae (b5) to (b7), $R^{14b}$ and $R^{18b}$ to $R^{23b}$ each independently represent a hydrogen atom, a linear or branched alkyl group having 1 or more and 6 or less carbon atoms, a fluorine atom, or a linear or branched fluorinated alkyl group having 1 or more and 6 or less carbon atoms; $R^{15b}$ to $R^{17b}$ each independently represent a linear or branched alkyl group having 1 or more and 6 or less carbon atoms, a linear or branched fluorinated alkyl group having 1 or more and 6 or less carbon atoms, or an aliphatic cyclic group having 5 or more and 20 or less carbon atoms, and each independently represent a linear or branched alkyl group having 1 or more and 6 or less carbon atoms, or a linear or branched fluorinated alkyl group having 1 or more and 6 or less carbon atoms; and $R^{16b}$ and $R^{17b}$ may be bonded to each other to form a hydrocarbon ring having 5 or more and 20 or less carbon atoms together with the carbon atom to which both the groups are bonded; $Y^b$ represents an optionally substituted aliphatic group or alkyl group; p is an integer of 0 or more and 4 or less; and q is 0 or 1.

Note here that examples of the linear or branched alkyl group include a methyl group, ethyl group, propyl group, isopropyl group, n-butyl group, isobutyl group, tert-butyl group, pentyl group, isopentyl group, neopentyl group, and the like. Furthermore, the fluorinated alkyl group refers to the abovementioned alkyl groups of which the hydrogen atoms are partially or entirely substituted with fluorine atoms. Specific examples of aliphatic cyclic groups include groups obtained by removing one or more hydrogen atoms from monocycloalkanes or polycycloalkanes such as bicycloalkanes, tricycloalkanes, and tetracycloalkanes. Specifically, groups obtained by removing one hydrogen atom from a monocycloalkane such as cyclopentane, cyclohexane, cycloheptane, or cyclooctane, or a polycycloalkane such as adamantane, norbornane, isobornane, tricyclodecane, or tetracyclododecane may be mentioned. In particular, groups obtained by removing one hydrogen atom from cyclohexane or adamantane (which may further be substituted) are preferred.

When $R^{16b}$ and $R^{17b}$ do not combine with each other to form a hydrocarbon ring, the above $R^{15b}$, $R^{16b}$, and $R^{17b}$ represent preferably a linear or branched alkyl group having 1 or more and 4 or less carbon atoms, and more preferably a linear or branched alkyl group having 2 or more and 4 or less carbon atoms, for example, from the viewpoints of a high contrast and favorable resolution and depth of focus. The above $R^{19b}$, $R^{20b}$, $R^{22b}$, and $R^{23b}$ preferably represent a hydrogen atom or a methyl group.

The above $R^{16b}$ and $R^{17b}$ may form an aliphatic cyclic group having 5 or more and 20 or less carbon atoms together with a carbon atom to which the both are attached. Specific examples of such an alicyclic group are the groups of monocycloalkanes and polycycloalkanes such as bicycloalkanes, tricycloalkanes and tetracycloalkanes from which one or more hydrogen atoms are removed. Specific examples thereof are the groups of monocycloalkanes such as cyclopentane, cyclohexane, cycloheptane and cyclooctane and polycycloalkanes such as adamantane, norbornane, isobornane, tricyclodecane and tetracyclododecane from which one or more hydrogen atoms are removed. Particularly preferable are the groups of cyclohexane and adamantane from which one or more hydrogen atoms are removed (that may further have a substituent).

Further, in a case where an aliphatic cyclic group to be formed with the above $R^{16b}$ and $R^{17b}$ has a substituent on the ring skeleton thereof, examples of the substituent include a polar group such as a hydroxyl group, a carboxyl group, a cyano group and an oxygen atom (=O), and a linear or branched alkyl group having 1 or more and 4 or less carbon atoms. As the polar group, an oxygen atom (=O) is particularly preferred.

The above $Y^b$ is an alicyclic group or an alkyl group; and examples thereof are the groups of monocycloalkanes and polycycloalkanes such as bicycloalkanes, tricycloalkanes and tetracycloalkanes from which one or more hydrogen atoms are removed. Specific examples thereof are the groups of monocycloalkanes such as cyclopentane, cyclohexane, cycloheptane and cyclooctane, and polycycloalkanes such as adamantane, norbornane, isobornane, tricyclodecane and tetracyclododecane from which one or more hydrogen atoms are removed. Particularly preferable is the group of adamantane from which one or more hydrogen atoms are removed (that may further have a substituent).

When the alicyclic group of the above $Y^b$ has a substituent on the ring skeleton, the substituent is exemplified by polar groups such as a hydroxyl group, carboxyl group, cyano group and oxygen atom (=O), and linear or branched alkyl groups having 1 or more and 4 or less carbon atoms. The polar group is preferably an oxygen atom (=O) in particular.

When $Y^b$ is an alkyl group, it is preferably a linear or branched alkyl group having 1 or more and 20 or less carbon atoms, and more preferably 6 or more and 15 or less carbon atoms. The alkyl group is an alkoxyalkyl group particularly preferable. Examples of such an alkoxyalkyl group include a 1-methoxyethyl group, 1-ethoxyethyl group, 1-n-propoxyethyl group, 1-isopropoxyethyl group, 1-n-butoxyethyl group, 1-isobutoxyethyl group, 1-tert-butoxyethyl group, 1-methoxypropyl group, 1-ethoxypropyl group, 1-methoxy-1-methylethyl group, 1-ethoxy-1-methylethyl group, and the like.

Preferable specific examples of the constituent unit represented by the above formula (b5) include those represented by the following formulae (b5-1) to (b5-33).

[Chem. 34]

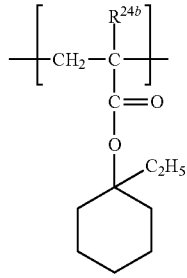
(b5-1)

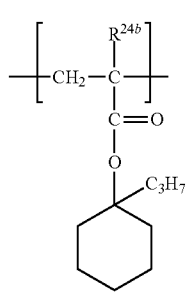
(b5-2)

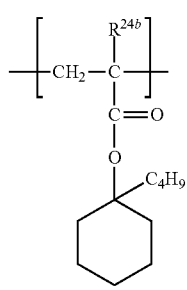
(b5-3)

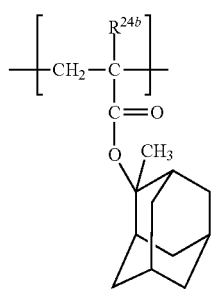
(b5-4)

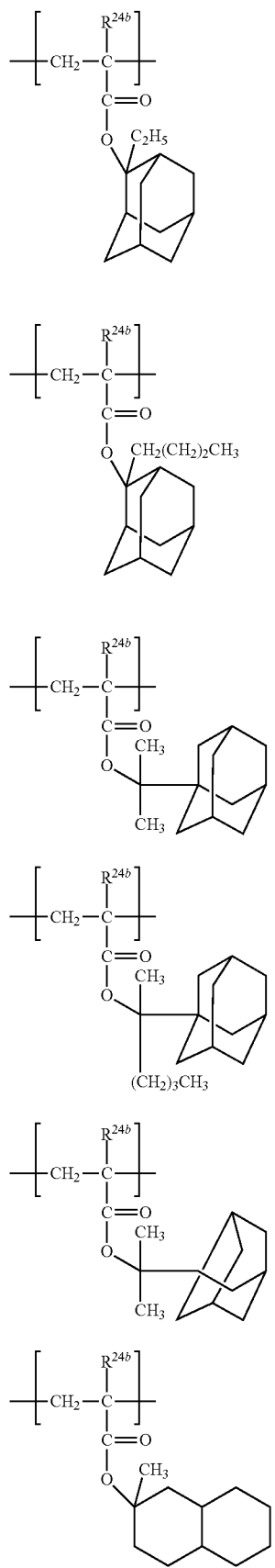
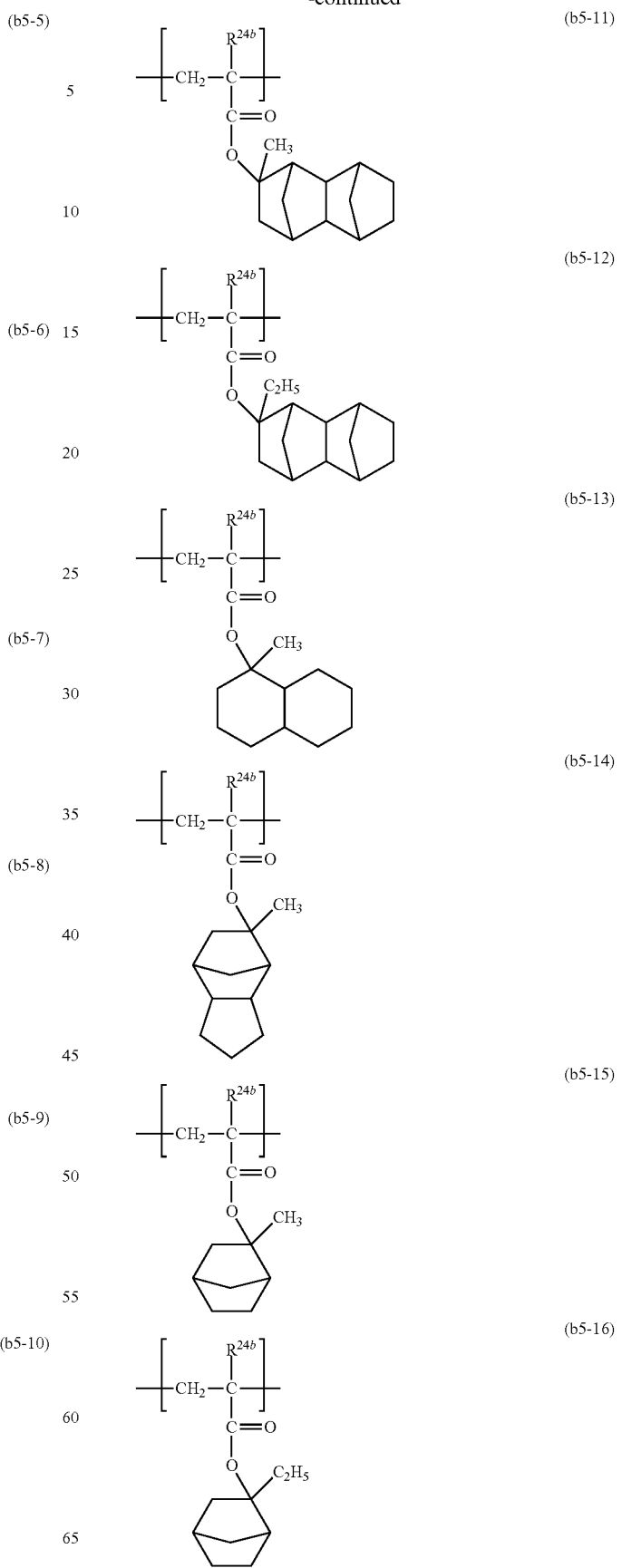

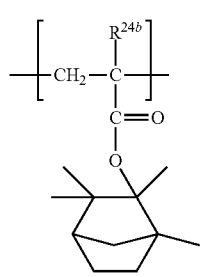
(b5-17)
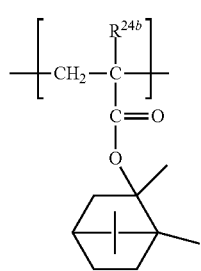
(b5-18)
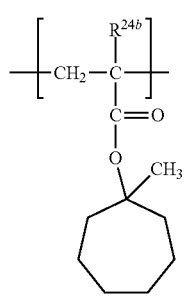
(b5-19)
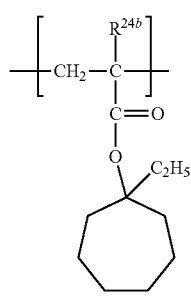
(b5-20)
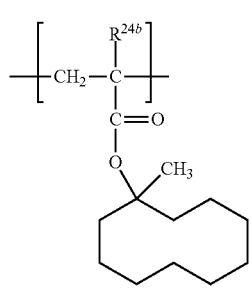
(b5-21)
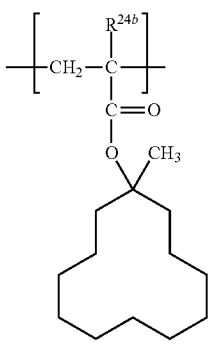
(b5-22)
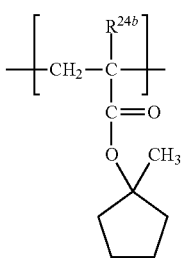
(b5-23)
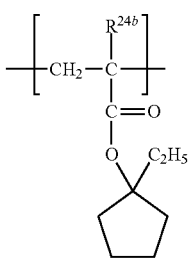
(b5-24)
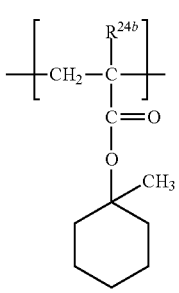
(b5-25)
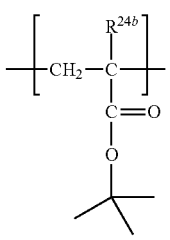
(b5-26)

(b5-27)
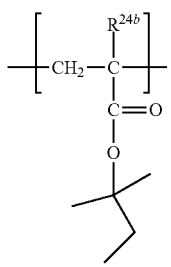
(b5-28)
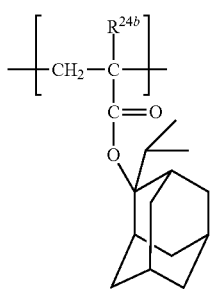
(b5-29)
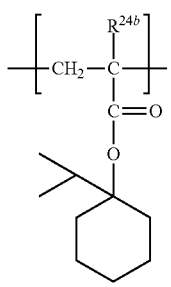
(b5-30)
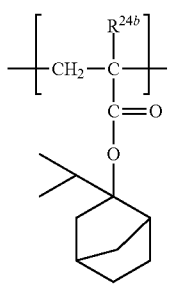
(b5-31)
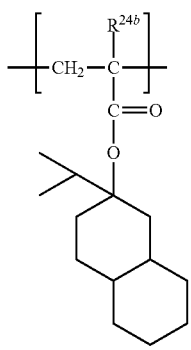
(b5-32)
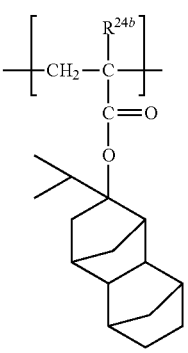
(b5-33)
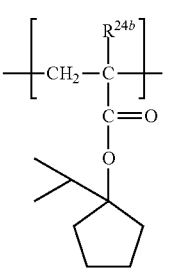
In the above formulae (b5-1) to (b5-33), $R^{24b}$ represents a hydrogen atom or a methyl group.
Preferable specific examples of the constituent unit represented by the above formula (b6) include those represented by the following formulae (b6-1) to (b6-26).
[Chem. 35]
(b6-1)
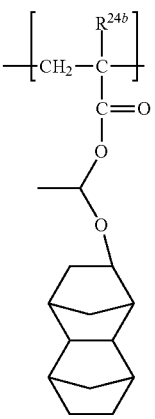
(b6-2)
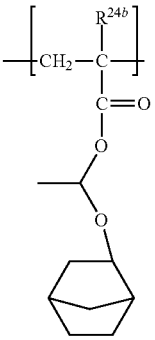

(b6-3) 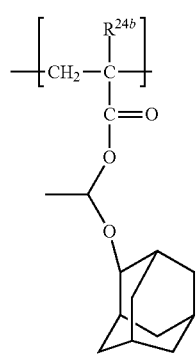
(b6-4) 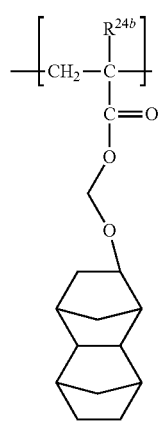
(b6-5) 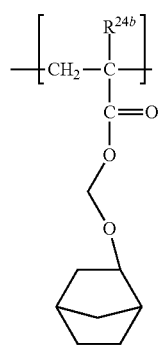
(b6-6) 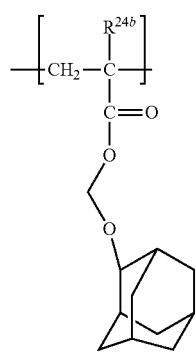
(b6-7) 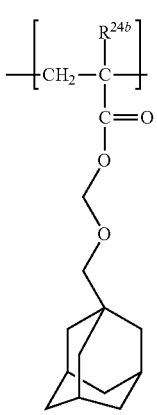
(b6-8) 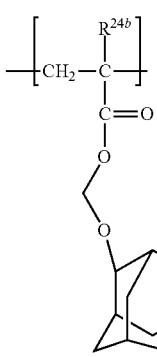
(b6-9) 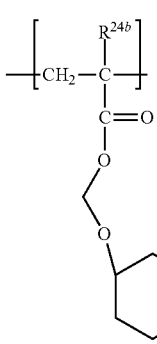
(b6-10) 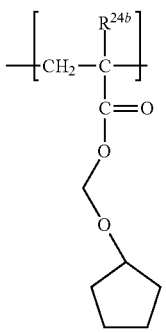

(b6-11) 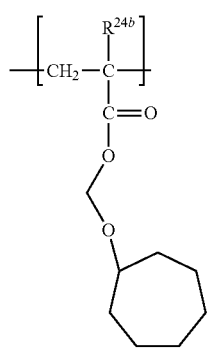
(b6-12) 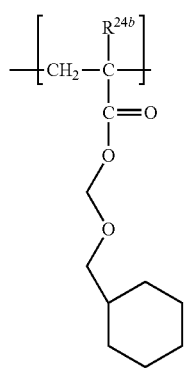
(b6-13) 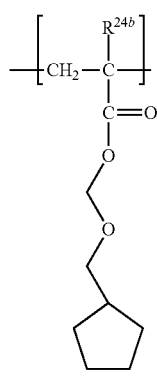
(b6-14) 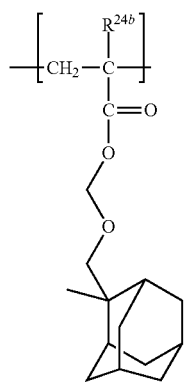
(b6-15) 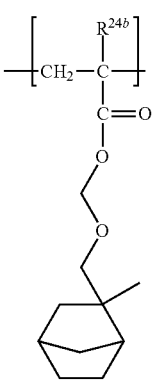
(b6-16) 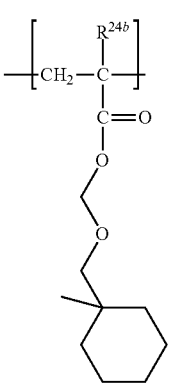
(b6-17) 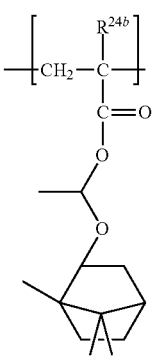
(b6-18) 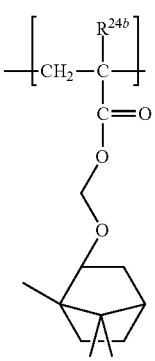

(b6-19) 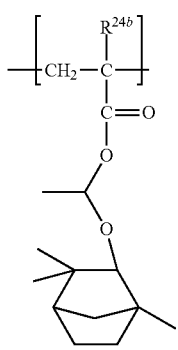
(b6-20) 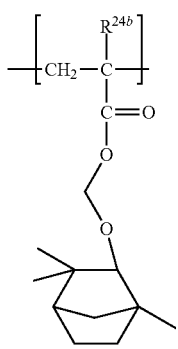
(b6-21) 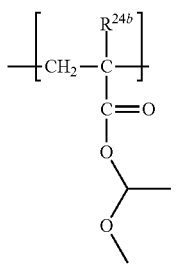
(b6-22) 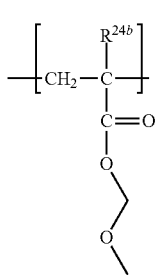
(b6-23) 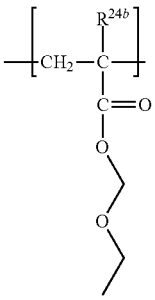
(b6-24) 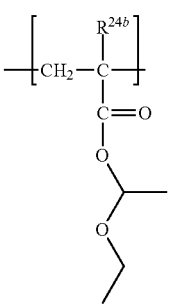
(b6-25) 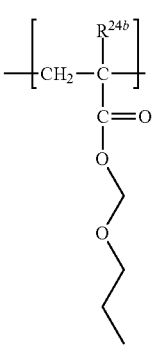
(b6-26) 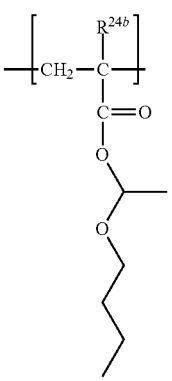
In the above formulae (b6-1) to (b6-26), $R^{24b}$ represents a hydrogen atom or a methyl group.
Preferable specific examples of the constituent unit represented by the above formula (b7) include those represented by the following formulae (b7-1) to (b7-15).

[Chem. 36]
(b7-1) 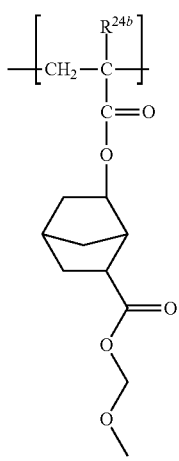
(b7-2) 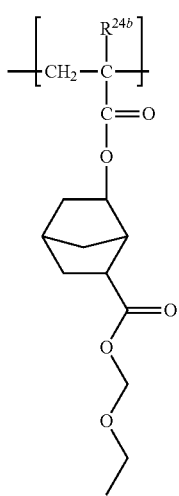
(b7-3) 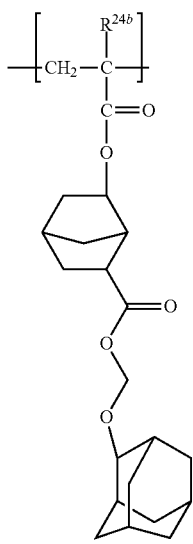
-continued
(b7-4) 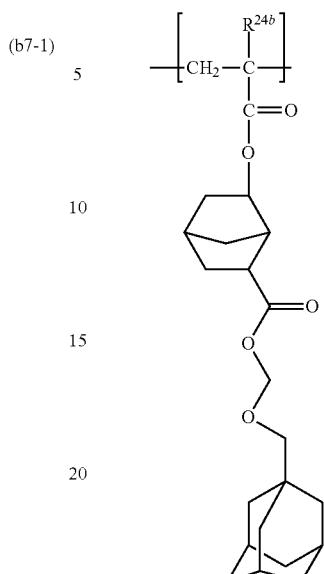
(b7-5) 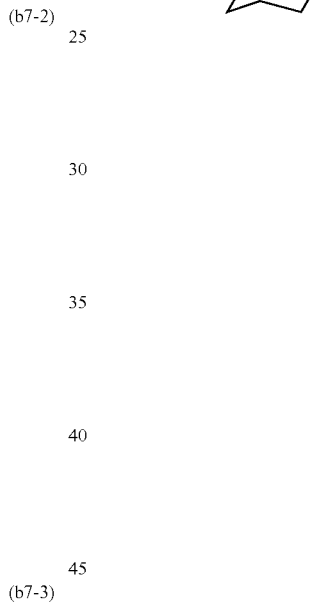

(b7-6)
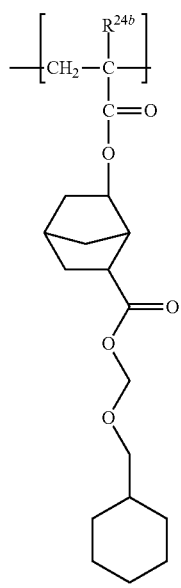
(b7-8)
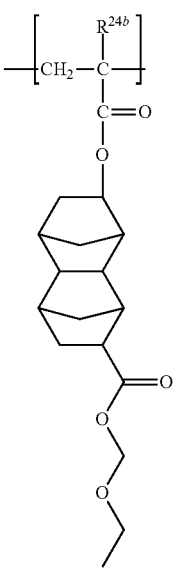
(b7-7)
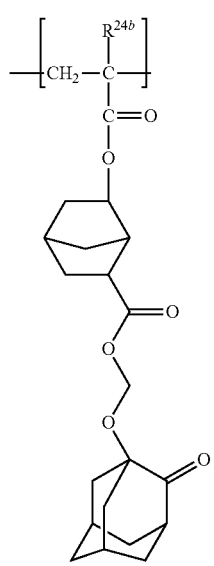
(b7-9)
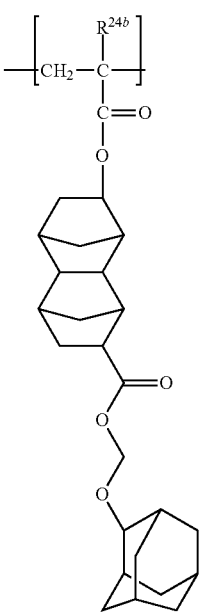

(b7-10)
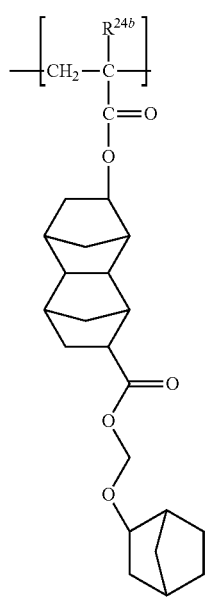
(b7-11)
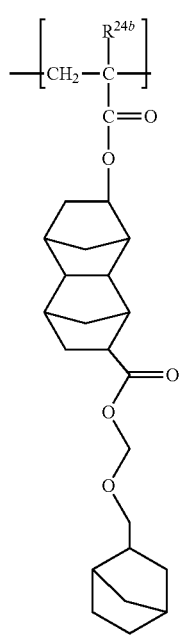
(b7-12)
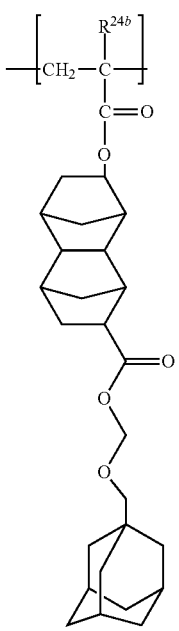
(b7-13)
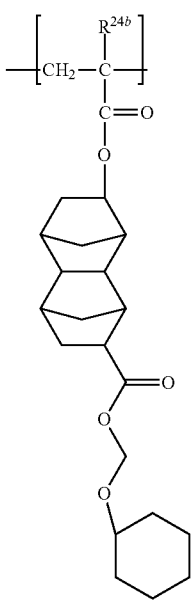

(b7-14)

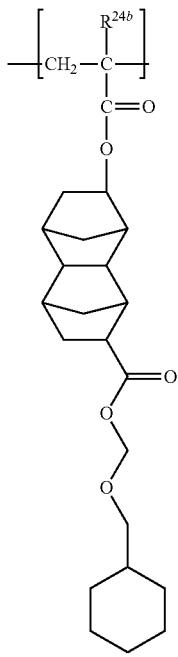

(b7-15)

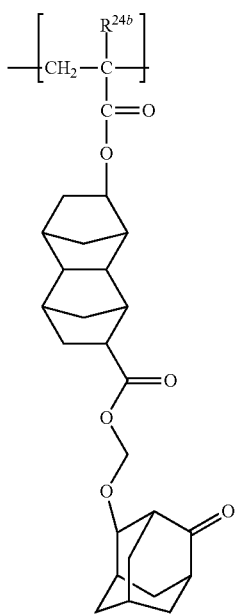

In the above formulae (b7-1) to (b7-15), $R^{24b}$ represents a hydrogen atom or a methyl group.

Among the constituent units represented by the formulae (b5) to (b7) described above, those represented by the formula (b6) are preferred in that they can be easily synthesized and relatively easily sensitized. Further, among the constituent units represented by the formula (b6), those in which $Y^b$ is an alkyl group are preferred, and those in which one or both of $R^{19b}$ and $R^{20b}$ are alkyl groups are preferred.

Further, the acrylic resin (B3) is preferably a resin including a copolymer including a constituent unit derived from a polymerizable compound having an ether bond together with a constituent unit represented by the above formulae (b5) to (b7).

Illustrative examples of the polymerizable compound having an ether bond include radical polymerizable compounds such as (meth)acrylic acid derivatives having an ether bond and an ester bond, and specific examples thereof include 2-methoxyethyl (meth)acrylate, 2-ethoxyethyl (meth)acrylate, methoxytriethylene glycol (meth)acrylate, 3-methoxybutyl (meth)acrylate, ethylcarbitol (meth)acrylate, phenoxypolyethylene glycol (meth)acrylate, methoxypolyethylene glycol (meth)acrylate, methoxypolypropylene glycol (meth)acrylate, tetrahydrofurfuryl (meth)acrylate, and the like. Also, the above polymerizable compound having an ether bond is preferably, 2-methoxyethyl (meth)acrylate, 2-ethoxyethyl (meth)acrylate, or methoxytriethylene glycol (meth)acrylate. These polymerizable compounds may be used alone, or in combinations of two or more thereof.

Furthermore, the acrylic resin (B3) may include another polymerizable compound as a constituent unit in order to moderately control physical or chemical properties. The polymerizable compound is exemplified by conventional radical polymerizable compounds and anion polymerizable compounds.

Examples of the polymerizable compound include monocarboxylic acids such as acrylic acid, methacrylic acid and crotonic acid; dicarboxylic acids such as maleic acid, fumaric acid and itaconic acid; methacrylic acid derivatives having a carboxyl group and an ester bond such as 2-methacryloyloxyethyl succinic acid, 2-methacryloyloxyethyl maleic acid, 2-methacryloyloxyethyl phthalic acid, and 2-methacryloyloxyethyl hexahydrophthalic acid; (meth) acrylic acid alkyl esters such as methyl(meth)acrylate, ethyl (meth)acrylate, butyl(meth)acrylate and cyclohexyl(meth) acrylate; (meth)acrylic acid hydroxyalkyl esters such as 2-hydroxyethyl (meth)acrylate and 2-hydroxypropyl (meth) acrylate; (meth)acrylic acid aryl esters such as phenyl (meth) acrylate and benzyl (meth)acrylate; dicarboxylic acid diesters such as diethyl maleate and dibutyl fumarate; vinyl group-containing aromatic compounds such as styrene, α-methylstyrene, chlorostyrene, chloromethylstyrene, vinyltoluene, hydroxystyrene, α-methylhydroxystyrene and α-ethylhydroxystyrene; vinyl group-containing aliphatic compounds such as vinyl acetate; conjugated diolefins such as butadiene and isoprene; nitrile group-containing polymerizable compounds such as acrylonitrile and methacrylonitrile; chlorine-containing polymerizable compounds such as vinyl chloride and vinylidene chloride; amide bond-containing polymerizable compounds such as acrylamide and methacrylamide; and the like.

As described above, the acrylic resin (B3) may include a constituent unit derived from a polymerizable compound having a carboxy group such as the above monocarboxylic acids and dicarboxylic acids. However, it is preferable that the acrylic resin (B3) does not substantially include a constituent unit derived from a polymerizable compound having a carboxyl group, since a resist pattern including a nonresist portion having a more favorable rectangular sectional shape can easily be formed. Specifically, the proportion of a constituent unit derived from a polymerizable compound having a carboxyl group in the acrylic resin (B3) is preferably 20% by mass or less, more preferably 15% by mass or less, and particularly preferably 10% by mass or less. In acrylic resin (B3), acrylic resin including a relatively large amount of constituent unit derived from a polymerizable compound having a carboxy group is preferably used in combination with an acrylic resin that includes only a small amount of constituent unit derived from a polymerizable compound having a carboxy group or does not include this constituent unit.

Furthermore, examples of the polymerizable compound include (meth)acrylic acid esters having a non-acid-dissociable aliphatic polycyclic group, and vinyl group-containing aromatic compounds and the like. As the non-acid-dissociable aliphatic polycyclic group, particularly, a tricyclodecanyl group, an adamantyl group, a tetracyclododecanyl group, an isobornyl group, a norbornyl group, and the like are preferred in view of easy industrial availability and the like. These aliphatic polycyclic groups may have a linear or branched alkyl group having 1 or more and 5 or less carbon atoms as a substituent.

Specific examples of the (meth)acrylic acid esters having a non-acid-dissociable aliphatic polycyclic group include those having structures represented by the following formulae (b8-1) to (b8-5).

[Chem. 37]

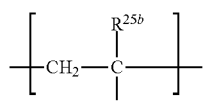
(b8-1)

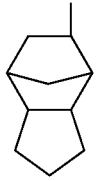

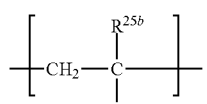
(b8-2)

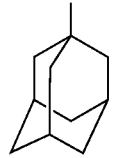

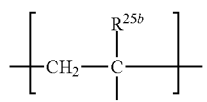
(b8-3)

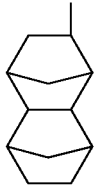

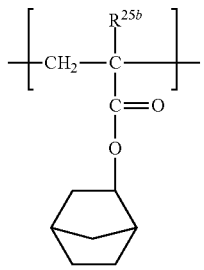
(b8-4)

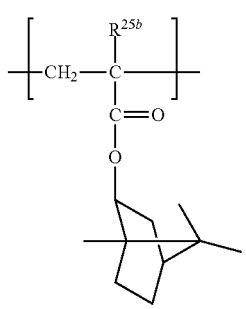
(b8-5)

In the formulae (b8-1) to (b8-5), $R^{25b}$ represents a hydrogen atom or a methyl group.

When the acrylic resin (B3) includes the constituent unit (b-3) including a —$SO_2$-containing cyclic group or a lactone-containing cyclic group, the content of the constituent unit (b-3) in the acrylic resin (B3) is preferably 5% by mass or more, more preferably 10% by mass or more, and particularly preferably 10% by mass or more and 50% by mass or less, and most preferably 10% by mass or more and 30% by mass or less. In a case where the positive-type photosensitive composition includes the constituent unit (b-3) having the above-mentioned range of amount, both good developing property and a good pattern shape can be easily achieved simultaneously.

Further, in the acrylic resin (B3), a constituent unit represented by the aforementioned formulae (b5) to (b7) is preferably included in an amount of 5% by mass or more, more preferably 10% by mass or more, and particularly preferably 10% by mass or more and 50% by mass or less.

The acrylic resin (B3) preferably includes the above constituent unit derived from a polymerizable compound having an ether bond. The content of the constituent unit derived from a polymerizable compound having an ether bond in the acrylic resin (B3) is preferably 0% by mass or more and 50% by mass or less, more preferably 5% by mass or more and 40% by mass or less, and further more preferably 5% by mass or more and 30% by mass or less.

The acrylic resin (B3) preferably includes the above constituent unit derived from (meth)acrylic acid esters having a non-acid-dissociable aliphatic polycyclic group. The content of the constituent unit derived from (meth)acrylic acid esters having a non-acid-dissociable aliphatic polycyclic group in the acrylic resin (B3) is preferably 0% by mass or more and 60% by mass or less, more preferably 5% by mass or more and 50% by mass or less, and further more preferably 5% by mass or more and 30% by mass or less.

As long as the positive-type photosensitive composition contains a predetermined amount of the acrylic resin (B3), an acrylic resin other than the acrylic resin (B3) described above can also be used as the resin (B). There is no particular limitation for such an acrylic resin other than the acrylic resin (B3) as long as it includes a constituent unit represented by the aforementioned formulae (b5) to (b7).

The mass-average molecular weight of the resin (B) described above in terms of polystyrene is preferably 10000 or more and 600000 or less, more preferably 20000 or more and 400000 or less, and even more preferably 30000 or more and 300000 or less. A mass-average molecular weight within these ranges allows a photosensitive layer made of a positive-type photosensitive composition to maintain sufficient strength without reducing detachability from a substrate, and can further prevent a swelled profile and crack generation when plating.

It is also preferred that the resin (B) has a dispersivity of 1.05 or more. Dispersivity herein indicates a value of a mass average molecular weight divided by a number average molecular weight. A dispersivity in the range described above can avoid problems with respect to stress resistance on intended plating or possible swelling of metal layers resulting from the plating process.

The content of the resin (B) is preferably 5% by mass or more and 60% by mass or less with respect to the total mass of the positive-type photosensitive composition. Furthermore, the content of the resin (B) is preferably 5% by mass or more and 98% by mass or less, and more preferably 10% by mass or more and 95% by mass or less with respect to the total solid mass of the positive-type photosensitive composition.

<Acid Diffusion Suppressing Agent (C)>

An acid diffusion suppressing agent (C) included in a positive-type photosensitive composition includes a compound represented by the following formula (C1). When the positive-type photosensitive composition includes a compound represented by the following formula (C1) as the acid diffusion suppressing agent (C), a photosensitive resin composition with which the resist pattern whose cross-sectional shape is rectangular is easily formed and which has a wide depth of focus (DOF) margin is obtained. This is estimated that because the compound represented by the following formula (C1) is a polyfunctional aniline compound having a plurality of aniline structures and the aniline structures are linked via $A^{c1}$ including a cyclic group, the acid deactivation ability by the acid diffusion suppressing agent (C) is improved when the acid diffusion suppressing agent (C) includes the compound represented by formula (C1), and, in the case of the positive type, diffusion of acids to the unexposed area is favorably suppressed.

[Chem. 38]

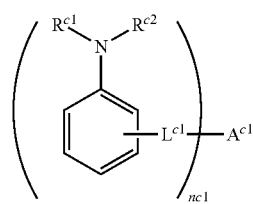

(C1)

(In the formula (C1),
a plurality of $R^{c1}$ each independently is an alkyl group having 1 or more and 6 or less carbon atoms optionally having a substituent, or a hydrogen atom;
a plurality of $R^{c2}$ each independently is an alkyl group having 1 or more and 6 or less carbon atoms optionally having a substituent, or a hydrogen atom;

$R^{c1}$ and $R^{c2}$ are linked to each other to form a ring;
$A^{c1}$ is an nc1-valence organic group including a cyclic group optionally having a substituent;
a plurality of $L^{c1}$ each independently is a single bond or a divalent linking group;
$L^{c1}$ is bonded to the cyclic group in $A^{c1}$; and
nc1 is an integer of 2 or more.)

In the formula (C1), the alkyl group as Rd may be linear or branched. Specific examples of the alkyl group include a methyl group, an ethyl group, an n-propyl group, an isopropyl group, an n-butyl group, an isobutyl group, a sec-butyl group, a tert-butyl group, an n-pentyl group, an n-hexyl group, and the like. Examples of the substituent, which the alkyl group as Rd may have, include a hydroxyl group, a mercapto group, an amino group, a halogen atom, an oxygen atom, a nitro group, a cyano group, and the like. In the formula (C1), an alkyl group as $R^{c2}$, and substituents the alkyl group may have are the same as those of Rd in the formula (C1). $Rc_1$ and $R^{c2}$ may be linked to each other to form a ring. $R^{c1}$ and $R^{c2}$ in this case form a heterocycle together with a nitrogen atom which $R^{c1}$ and $R^{c2}$ bond. Examples of the formed heterocycle include a piperidine ring, a piperazine ring, a morpholine ring, a thiomorpholine ring, and the like. $R^{c1}$ and $R^{c2}$ are preferably an alkyl group in view of preservation stability of the photosensitive composition.

In the formula (C1), an nc1-valence organic group including a cyclic group as $A^{c1}$ may be a group only including one or more cyclic groups or a group combining a cyclic group and an acyclic group. When $A^{c1}$ is a group including a combination of a cyclic group and an acyclic group, the cyclic group and an acyclic group constituting $A^{c1}$ may be one or two or more, respectively.

The cyclic group included in $A^{c1}$ may be a cyclic hydrocarbon group, or may be a heterocyclic group. Suitable examples of the hetero atom constituting the heterocyclic group include a nitrogen atom, an oxygen atom, a sulfur atom, a phosphorus atom, a boron atom, and a silicon atom. Among them, a nitrogen atom, an oxygen atom, and a sulfur atom are preferable. The cyclic group included in $A^{c1}$ may be an aromatic group, or an aliphatic cyclic group. $A^{c1}$ preferably includes an aromatic group. The aromatic group included in $A^{c1}$ may be an aromatic hydrocarbon group or an aromatic heterocyclic group. When the cyclic group included in $A^{c1}$ is an aliphatic cyclic group, the aliphatic cyclic group may be saturated aliphatic cyclic group, or an unsaturated aliphatic cyclic group. When $A^{c1}$ includes an aliphatic cyclic group, the aliphatic cyclic group is preferably a saturated aliphatic cyclic group.

The structure of the cyclic group included in $A^{c1}$ may be monocyclic or polycyclic. In view of suppressing the generation of residues after development, the structure of the cyclic group included in $A^{c1}$ is preferably a monocyclic structure. The total of the number of ring-constituting atoms of one or two or more cyclic groups included in $A^{c1}$ (the number of the ring-constituting atoms that constitute $A^{c1}$) is not particularly limited within a range where the objects of the present invention are not impaired. The total number of the ring-constituting atoms in the rings constituting $A^{c1}$ may be typically 3 or more and 50 or less, 6 or more and 40 or less, and 12 or more and 30 or less. For example, when $A^{c1}$ is biphenyl ether-4,4'-diyl group, the total number of the ring-constituting atoms in one or two or more cyclic groups included in $A^{c1}$ is 12.

When the structure of the cyclic group constituting $A^{c1}$ is a polycyclic structure, the polycyclic structure may be a polycyclic structure in which two or more monocyclic rings are condensed, or a polycyclic structure in which two or more rings are bonded to each other via a single bond or a linking group, or a polycyclic ring structure that a polycyclic system such as bicyclic or tricyclic or more, or a spirocyclic structure.

When the structure of the cyclic group constituting $A^{c1}$ is a polycyclic structure, the polycyclic structure may be formed of two or more aromatic monocyclic rings, or formed of two or more aliphatic monocyclic rings, or formed of one or more aromatic monocyclic rings and one or more aliphatic monocyclic rings. The number of monocyclic rings constituting the polycyclic structure is not particularly limited. The number of monocyclic rings constituting the polycyclic structure is, for example, 5 or less. The number of ring-constituting atoms of monocyclic rings constituting a polycyclic structure is preferably 3 or more and 20 or less, more preferably 4 or more and 16 or less, and particularly preferably 5 or more and 12 or less.

When the structure of the cyclic group constituting $A^{c1}$ is a monocyclic structure, specific examples of the monocyclic structure include aromatic hydrocarbon rings such as a benzene ring; aliphatic hydrocarbon rings such as a cyclopentane ring, a cyclohexane ring, a cycloheptane ring, a cyclooctane ring, a cyclononane ring, a cyclodecane ring, a cycloundecane ring, and a cyclododecane ring; aromatic heterocycles such as a pyrrole ring, a furan ring, a thiophene ring, a pyran ring, a pyridine ring, a pyridazine ring, a pyrimidine ring, a pyrazine ring, a triazine ring, a pyrazole ring, an isoxazole ring, an isothiazole ring, an imidazole ring, an oxazole ring, a thiazole ring, a triazole ring, an oxadiazole ring, and a thiadiazole ring; aliphatic heterocycle such as a pyrrolidine ring, a tetrahydrofuran ring, a tetrahydrothiophene ring, a piperidine ring, a tetrahydropyran ring, a tetrahydrothiopyran ring, a piperazine ring, a morpholine ring, and a dioxane ring, and the like.

When the structure of the cyclic group constituting $A^{c1}$ is a polycyclic structure, specific examples of the polycyclic structure include aromatic hydrocarbon rings such as a naphthalene ring, a biphenyl ring, an anthracene ring, and a phenanthrene ring; aliphatic hydrocarbon rings such as a decalin ring, a hydrindane ring, an adamantane ring, a norbornane ring, a norbornene ring, an isobornane ring, a tricyclodecane ring, and a tetracyclododecane ring; rings each composed of an aliphatic hydrocarbon ring and an aromatic hydrocarbon ring, such as a tetralin ring, an indane ring, a cyclopentylbenzene ring, and a cyclohexylbenzene ring; aromatic heterocycles such as an indole ring, an indazole ring, a benzimidazole ring, a benzoxazole ring, a benzothiazole ring, a quinoline ring, an isoquinoline ring, a cinnoline ring, a phthalazine ring, a quinazoline ring, a quinoxaline ring, a naphthyridine ring, a pteridine ring, a carbazole ring, and an acridine ring; aliphatic heterocycles such as a 7-oxanorbornane ring, a 7-thionorbornane ring, and a 7-azanorbornane ring; rings each composed of aliphatic heterocycle and aromatic hydrocarbon ring, such as an indoline ring, and a chroman ring, and the like.

The cyclic group included in $A^{c1}$ may include arbitrary types and arbitrary numbers of substituents within a range where the objects of the present invention are not impaired. When the cyclic group included in $A^{c1}$ includes a substituent, the number of substituents differs depending on the number of ring-constituting atoms of the cyclic group included in $A^{c1}$, but the number is preferably 1 or more and 6 or less, more preferably 1 or more and 4 or less, and particularly preferably 1 or 2.

Examples of the substituent include a halogen atom, a hydroxyl group, an alkyl group, an aralkyl group, an alkoxy group, a cycloalkyloxy group, an aryloxy group, an aralkyloxy group, an alkylthio group, a cycloalkylthio group, an arylthio group, an aralkylthio group, an acyl group, an acyloxy group, an acylthio group, an alkoxycarbonyl group, a cycloalkyloxycarbonyl group, an aryloxycarbonyl group, an amino group, an N-monosubstituted amino group, an N,N-disubstituted amino group, a carbamoyl group (—CO—NH$_2$), an N-monosubstituted carbamoyl group, an N,N-disubstituted carbamoyl group, a nitro group and a cyano group.

Examples of the halogen atom include a fluorine atom, a chlorine atom, a bromine atom, and an iodine atom.

The number of carbon atoms of the alkyl group is not particularly limited, and the number is preferably 1 or more and 6 or less, and more preferably 1 or more and 3 or less. The alkyl group may be linear or branched. Specific examples of the alkyl group include a methyl group, an ethyl group, an n-propyl group, an isopropyl group, an n-butyl group, an isobutyl group, a sec-butyl group, a tert-butyl group, an n-pentyl group, and an n-hexyl group.

The number of carbon atoms of the aralkyl group is not particularly limited, and is preferably 7 or more and 20 or less, and more preferably 7 or more and 13 or less. Specific examples of the aralkyl include a benzyl group, a phenethyl group, a naphthalene-1-ylmethyl group, and a naphthalene-2-ylmethyl group, and the like.

The number of carbon atoms of the alkoxy group is not particularly limited, and is preferably 1 or more and 6 or less, and more preferably 1 or more and 3 or less. The alkoxy group maybe linear or branched. Specific examples of the alkoxy group include a methoxy group, an ethoxy group, an n-propyloxy group, an isopropyloxy group, an n-butyloxy group, an isobutyloxy group, a sec-butyloxy group, a tert-butyloxy group, an n-pentyloxy group, and an n-hexyloxy group.

The number of carbon atoms of the cycloalkyloxy group is not particularly limited, and is preferably 3 or more and 10 or less, and more preferably 3 or more and 8 or less. Specific examples of the cycloalkyloxy group include a cyclopropyloxy group, a cyclobutyloxy group, a cyclopentyloxy group, a cyclohexyloxy group, a cycloheptyloxy group, a cyclooctyloxy group, a cyclononyloxy group, and a cyclodecyloxy group.

The number of carbon atoms of the aryloxy group is not particularly limited, and is preferably 6 or more and 20 or less, and more preferably 6 or more and 12 or less. Specific examples of the aryloxy group include a phenoxy group, a naphthalene-1-yloxy group, a naphthalene-2-yloxy group, and biphenylyloxy group.

The number of carbon atoms of the aralkyloxy group is not particularly limited, and is preferably 7 or more and 20 or less, and more preferably 7 or more and 13 or less. Specific examples of the aralkyloxy group include a benzyloxy group, a phenethyloxy group, a naphthalene-1-ylmethoxy group, a naphthalene-2-ylmethoxy group, and the like.

The number of carbon atoms of the acyl group is not particularly limited, and is preferably 2 or more and 20 or less, and more preferably 2 or more and 11 or less. The acyl group maybe an aliphatic acyl group, or may be an aromatic acyl group including an aromatic group. Specific examples of the acyl group include an acetyl group, a propionyl group, a butanoyl group, a pentanoyl group, a hexanoyl group, an octanoyl group, a nonanoyl group, a decanoyl group, a benzoyl group, a naphthalene-1-yl carbonyl group, and a naphthalene-2-yl carbonyl group.

The number of carbon atoms of the acyloxy group is not particularly limited, and is preferably 2 or more and 20 or less, and more preferably 2 or more and 11 or less. The acyloxy group may be an aliphatic acyloxy group, and an aromatic acyloxy group including an aromatic group. Specific examples of the acyloxy group include an acetyloxy group, a propionyloxy group, a butanoyloxy group, a pentanoyloxy group, a hexanoyloxy group, an octanoyloxy group, a nonanoyloxy group, a decanoyloxy group, a benzoyloxy group, a naphthalene-1-yl carbonyloxy group, and a naphthalene-2-yl carbonyloxy group.

Suitable examples of an alkylthio group, a cycloalkylthio group, an arylthio group, an aralkylthio group, and an acylthio group include groups in which oxygen atom is changed to a sulfur atom in the suitable groups as the above-mentioned alkoxy group, cycloalkyloxy group, aryloxy group, aralkyloxy group, and acyloxy group.

The number of carbon atoms of the alkoxycarbonyl group is not particularly limited, and is preferably 2 or more and 7 or less, and more preferably 2 or more and 4 or less. The alkoxycarbonyl group may be linear or branched. Specific examples of the alkoxycarbonyl group include a methoxycarbonyl group, an ethoxycarbonyl group, an n-propyloxycarbonyl group, an isopropyloxycarbonyl group, an n-butyloxycarbonyl group, an isobutyloxycarbonyl group, a sec-butyloxycarbonyl group, a tert-butyloxycarbonyl group, an n-pentyloxycarbonyl group, and an n-hexyloxycarbonyl group.

The number of carbon atoms of the cycloalkyloxycarbonyl group is not particularly limited, and is preferably 4 or more and 11 or less, and more preferably 4 or more and 9 or less. Specific examples of the cycloalkyloxycarbonyl group include a cyclopropyloxycarbonyl group, a cyclobutyloxycarbonyl group, a cyclopentyloxycarbonyl group, a cyclohexyloxycarbonyl group, a cyclo heptyloxycarbonyl group, a cyclooctyloxycarbonyl group, a cyclononyloxycarbonyl group, and a cyclodecyloxycarbonyl group.

The number of carbon atoms of the aryloxycarbonyl group is not particularly limited, and is preferably 7 or more and 21 or less, and more preferably 7 or more and 13 or less. Specific examples of the aryloxycarbonyl group include a phenoxycarbonyl group, a naphthalene-1-yloxycarbonyl group, a naphthalene-2-yloxycarbonyl group, and a biphenylyloxycarbonyl group.

In the N-monosubstituted amino group and N,N-disubstituted amino group, the types of substituents bonded to a nitrogen atom are not particularly limited. Suitable examples of the substituents bonded to a nitrogen atom include an alkyl group having 1 or more and 6 or less carbon atoms which may be linear or branched, a cycloalkyl group having 3 or more and 10 or less carbon atoms, an aryl group having 6 or more and 20 or less carbon atoms, an aliphatic acyl group having 2 or more and 7 or less carbon atoms, and an aromatic acyl group having 7 or more and 21 or less carbon atoms. Suitable specific examples of the N-monosubstituted amino group include a methyl amino group, an ethyl amino group, an n-propyl amino group, an isopropyl amino group, an n-butyl amino group, an isobutyl amino group, a sec-butyl amino group, a tert-butyl amino group, an n-pentyl amino group, an n-hexyl amino group, a cyclopropyl amino group, a cyclobutyl amino group, a cyclopentyl amino group, a cyclohexyl amino group, a cycloheptyl amino group, a cyclooctyl amino group, a cyclononyl amino group, a cyclodecyl amino group, a phenyl amino group, a naphthalene-1-yl amino group, a naphthalene-2-yl amino group, a biphenylyl amino group, an acetyl amino group, a propionyl amino group, a butanoyl amino group, a pentanoy amino group, a hexanoyl amino group, an octanoyl amino group, a nonanoyl amino group, a decanoyl amino group, a benzoyl amino group, a naphthalene-1-yl carbonyl amino group, and a naphthalene-2-yl carbonyl amino group. Suitable examples of the N,N-disubstituted amino group include a dimethyl amino group, a diethyl amino group, a di-n-propyl amino group, a diisopropyl amino group, a di-n-butyl amino group, a diisobutyl amino group, a di-sec-butyl amino group, a di-tert-butyl amino group, a di-n-pentyl amino group, a di-n-hexyl amino group, a dicyclopentyl amino group, a dicyclohexyl amino group, a diphenyl amino group, a diacetyl amino group, a dipropionyl amino group, and a dibenzoyl amino group.

In the N-monosubstituted carbamoyl group and N,N-disubstituted carbamoyl group, the types of substituents bonded to a nitrogen atom are not particularly limited. Suitable examples of the substituents bonded to a nitrogen atom are the same as those descried as to the N-monosubstituted amino group and N,N-disubstituted amino group. Suitable specific examples of the N-monosubstituted amino carbamoyl group includes an N-methyl carbamoyl group, an N-ethyl carbamoyl group, an N-n-propylcarbamoyl group, an N-isopropyl carbamoyl group, an N-n-butylcarbamoyl group, an N-isobutylcarbamoyl group, an N-sec-butylcarbamoyl group, an N-tert-butylcarbamoyl group, an N-n-pentyl carbamoyl group, an N-n-hexylcarbamoyl group, an N-cyclopropylcarbamoyl group, an N-cyclobutylcarbamoyl group, an N-cyclopentyl carbamoyl group, an N-cyclohexylcarbamoyl group, an N-cycloheptylcarbamoyl group, an N-cyclooctylcarbamoyl group, an N-cyclononylcarbamoyl group, an N-cyclodecylcarbamoyl group, an N-phenylcarbamoyl group, an N-naphthalene-1-ylcarbamoyl group, an N-naphthalene-2-ylcarbamoyl group, an N-biphenylylcarbamoyl group, an N-acetylcarbamoyl group, an N-propionylcarbamoyl group, an N-butanoylcarbamoyl group, an N-pentanoycarbamoyl group, an N-hexanoylcarbamoyl group, an N-octanoylcarbamoyl group, an N-nonanoylcarbamoyl group, an N-decanoylcarbamoyl group, an N-benzoyl carbamoyl group, an N-naphthalene-1-yl carbonyl carbamoyl group, and an N-naphthalene-2-yl carbonyl carbamoyl group. Suitable examples of the N,N-disubstituted carbamoyl group include an N,N-dimethyl carbamoyl group, an N,N-diethyl carbamoyl group, an N,N-di-n-propylcarbamoyl group, an N,N-di isopropyl carbamoyl group, an N,N-di-n-butylcarbamoyl group, an N,N-diisobutylcarbamoyl group, an N,N-di-sec-butylcarbamoyl group, an N,N-di-tert-butylcarbamoyl group, an N,N-di-n-pentyl carbamoyl group, an N,N-di-n-hexyl carbamoyl group, an N,N-dicyclopentyl carbamoyl group, an N,N-dicyclohexyl carbamoyl group, an N,N-diphenylcarbamoyl group, an N,N-diacetylcarbamoyl group, an N,N-dipropionylcarbamoyl group, and an N,N-dibenzoyl carbamoyl group.

When $A^{c1}$ in the formula (C1) includes an acyclic group, the valency of the acyclic group is not particularly limited. The valency of the acyclic group included in $A^{c1}$ is preferably 2 or more and 4 or less, and more preferably 2 or 3. Preferable examples of the divalent acyclic group include an alkylene group, an alkenylene group, an alkynylene group, —O—, —CO—, —S—, —CS—, —NH—, —N=N—, —SO—, and —SO$_2$—, and groups combining two or more groups selected from these groups. The alkylene group, the alkenylene group, and the alkynylene group may include a substituent. The substituent is the same as the substituent which the cyclic group included in $A^{c1}$ have. Preferable examples of the trivalent acyclic group include groups in which one hydrogen atom is removed from the groups of the preferable examples of the divalent acyclic group. Preferable examples of the tetravalent acyclic group include groups in which two hydrogen atoms are removed from the groups of the preferable examples of the divalent acyclic group.

When the acyclic group included in $A^{c1}$ is an alkylene group, an alkenylene group, or an alkynylene group, the number of carbon atoms of these groups is preferably, for example, 2 or more and 10 or less, more preferably 2 or more and 6 or less, further preferably 2 or more and 4 or less, and particularly preferably 2.

In the formula (C1), examples of the divalent linking group as $L^{c1}$ include —O—, —CO—, —COO—, —OCOO—, —NH—, —CONH—, —NHCONH—, —S—, —SO—, and —SO$_2$—. $L^{c1}$ is bonded to a cyclic group in $A^{c1}$, but the direction of bonding when $L^{c1}$ is —COO— or —CONH— is not limited. Any of a carbon atom, an oxygen atom, and a nitrogen atom of $L^{c1}$ may be bonded to a cyclic group in Aol. In view of easy availability of raw materials and easy synthesis, $L^{c1}$ is preferably —COO— or —CONH—. The bonding position of $L^{c1}$ to the bonding position of —NR$^{c1}$R$^{c2}$ in the benzene ring to which —NR$^{c1}$R$^{c2}$ is bonded may be any of the ortho, meta, and para positions. The meta position or the para position is preferable.

In the formula (C1), nc1 is an integer of 2 or more. As nc1 is larger, a resist pattern whose cross-sectional shape is rectangular tends to be formed easily, and the depth of focus (DOF) margin is wider. The upper limit of nc1 is not particularly limited, but is, for example, 20 or less, more preferably 10 or less, and more preferably 8 or less.

The formula (C1) includes compounds represented by the following formula (C2).

[Chem. 39]

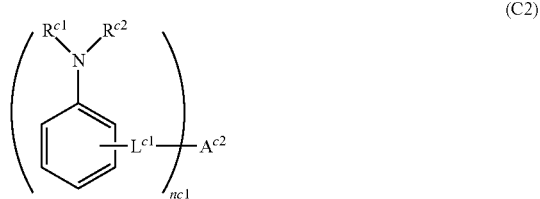

(C2)

(In the formula (C2),
a plurality of $R^{c1}$ each independently is an alkyl group having 1 or more and 6 or less carbon atoms optionally having a substituent, or a hydrogen atom;
a plurality of $R^{c2}$ each independently is an alkyl group having 1 or more and 6 or less carbon atoms optionally having a substituent, or a hydrogen atom;
the $R^{c1}$ and $R^{c2}$ are linked to each other to form a ring;
$A^{c2}$ is an nc1-valence organic group including two or more aromatic groups optionally having a substituent;
a plurality of $L^{c1}$ each independently is a single bond or a divalent linking group;
the $L^{c1}$ is bonded to the aromatic group in the $A^{c2}$; and
nc1 is an integer of 2 or more.)

In the formula (C2), $R^{c1}$, $R^{c2}$, and nc1 are each similar to the $R^{c1}$, $R^{c2}$, and nc1 in the formula (C1). In the formula (C2), $L^{c1}$ is the same as $L^{c1}$ in the formula (C1) except that it is bonded not to $A^{c1}$ but to $A^{c2}$.

In the formula (C2), an nc1-valence organic group as $A^{c2}$ including two or more aromatic groups may be a group only including two or more aromatic groups, or may be a group including a combination of two or more aromatic groups and at least one of an aliphatic cyclic group and an acyclic group. The aromatic group included in $A^{c2}$ is the same as the aromatic group described for $A^{c}1$ in the formula (C1), and may be an aromatic hydrocarbon group, or an aromatic heterocyclic group. The aliphatic cyclic group when $A^{c2}$ includes an aliphatic cyclic group is the same as the aliphatic cyclic group described for $A^{c1}$ in the formula (C1), and may be a saturated aliphatic cyclic group or an unsaturated aliphatic cyclic group, and may include a hetero atom.

When the structure of the aromatic group forming $A^{c2}$ is a monocyclic structure, specific examples of the monocyclic structure include aromatic heterocycles such as a benzene ring, a pyrrole ring, a furan ring, a thiophene ring, a pyran ring, a pyridine ring, a pyridazine ring, a pyrimidine ring, a pyrazine ring, a triazine ring, a pyrazole ring, an isoxazole ring, an isothiazole ring, an imidazole ring, an oxazole ring, a thiazole ring, a triazole ring, an oxadiazole ring, and a thiadiazole ring.

When the structure of the aromatic group forming $A^{c2}$ is a polycyclic structure, specific examples of the polycyclic structure include aromatic hydrocarbon rings such as a naphthalene ring, a biphenyl ring, an anthracene ring, and a phenanthrene ring; rings each composed of aliphatic hydrocarbon ring and aromatic hydrocarbon ring, such as a tetralin ring, an indan ring, a cyclopentylbenzene ring, and a cyclohexylbenzene ring; aromatic heterocycles such as an indole ring, an indazole ring, a benzimidazole ring, a benzoxazole ring, a benzothiazole ring, a quinoline ring, an isoquinoline ring, a cinnoline ring, a phthalazine ring, a quinazoline ring, a quinoxaline ring, a naphthyridine ring, a pteridine ring, a carbazole ring, and an acridine ring; and rings each composed of aliphatic heterocycle and aromatic hydrocarbon ring, such as an indoline ring, and a chroman ring.

When an nc1-valence organic group as $A^{c2}$ including two or more aromatic groups include an aliphatic cyclic group, and when the structure of the aliphatic cyclic group is a monocyclic structure, specific examples of the monocyclic structure include a monocyclic structure including aliphatic hydrocarbon rings such as a cyclopentane ring, a cyclohexane ring, a cycloheptane ring, a cyclooctane ring, a cyclononane ring, a cyclodecane ring, a cycloundecane ring, and a cyclododecane ring, and an aliphatic heterocycles such as a pyrrolidine ring, a tetrahydrofuran ring, a tetrahydrothiophene ring, a piperidine ring, a tetrahydropyran ring, a tetrahydrothiopyran ring, a piperazine ring, a morpholine ring, and a dioxane ring.

When an nc1-valence organic group as $A^{c2}$ including two or more aromatic groups include an aliphatic cyclic group, and when the structure of the aliphatic cyclic group is a polycyclic structure, specific examples of the polycyclic structure include a polycyclic structure including aliphatic hydrocarbon rings such as a decalin ring, a hydrindane ring, an adamantane ring, a norbornane ring, a norbornene ring, an isobornane ring, a tricyclodecane ring, and a tetracyclododecane ring, and an aliphatic heterocycle such as a 7-oxanorbornane ring, a 7-thionorbornane ring, and a 7-azanorbornane ring.

The aromatic group and the aliphatic cyclic group included in $A^{c2}$ may include arbitrary types and arbitrary numbers of substituents within a range where the objects of the present invention are not impaired. When the aromatic group and the aliphatic cyclic group included in $A^{c2}$ include a substituent, the substituent is the same as the substituent when the cyclic group included in $A^{c1}$ in the formula (C1) includes the substituent. When $A^{c2}$ includes an acyclic group, the acyclic group is the same as the acyclic group described for $A^{c1}$ in the formula (C1).

Specific examples of the compound represented by the formula (C1) include the following compounds.

[Chem. 40]

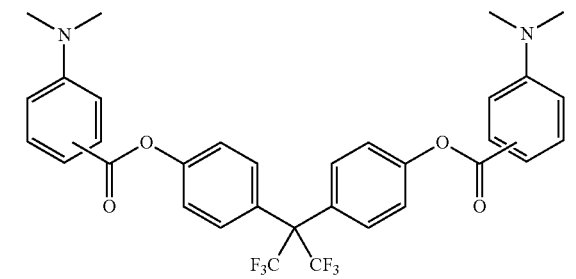

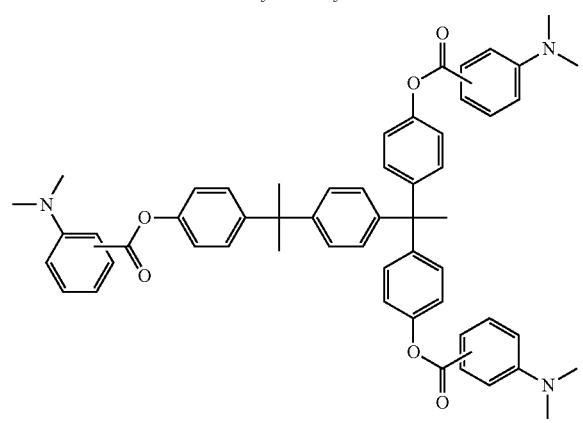

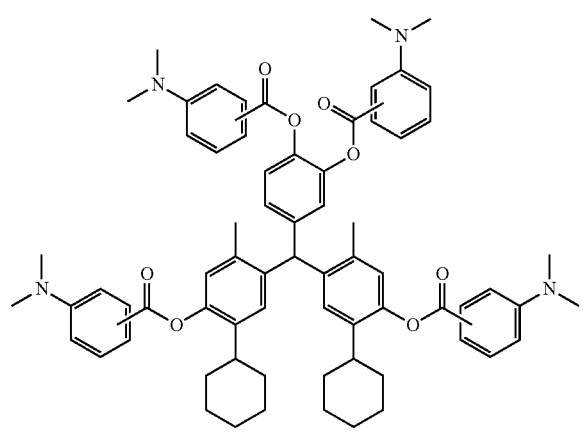

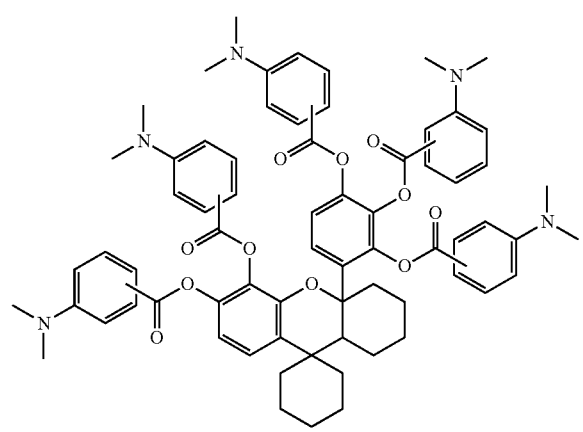

[Chem. 41]

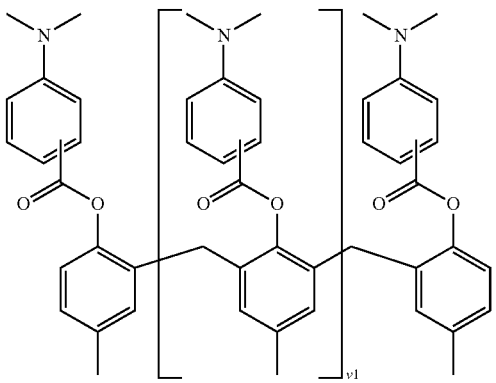

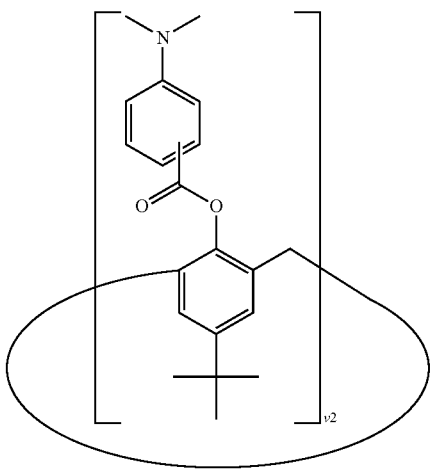

(The number of repetition v1 in the compound represented by the formula on the left represents an integer of 0 or more and 6 or less. The compound represented by the formula on the right is a calixarene, and the number of repetition v2 in the formula represents an integer of 4 or more and 8 or less.)

[Chem. 42]

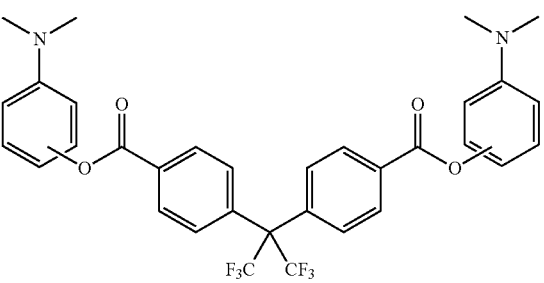

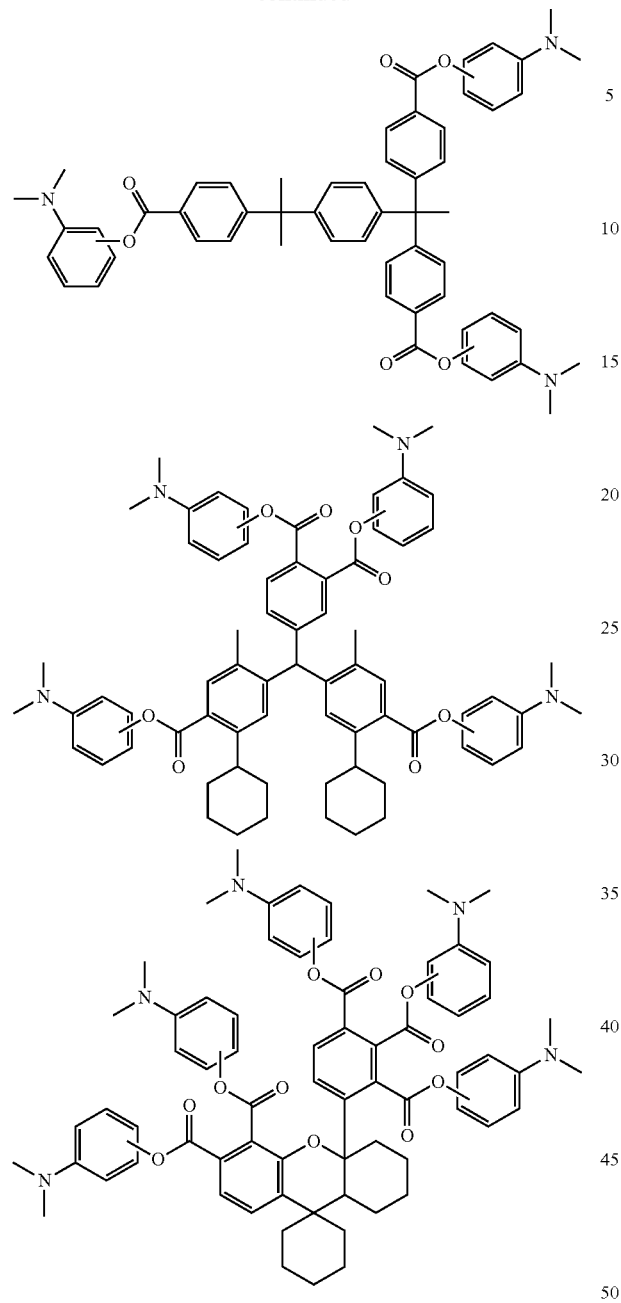
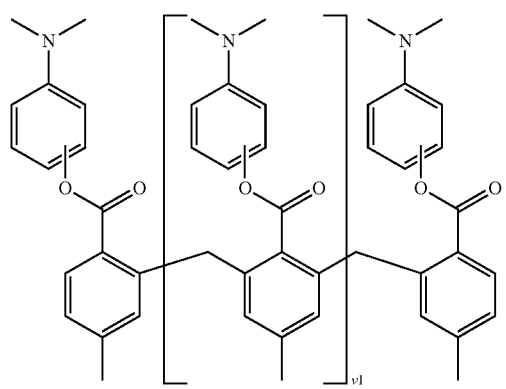
[Chem. 43]
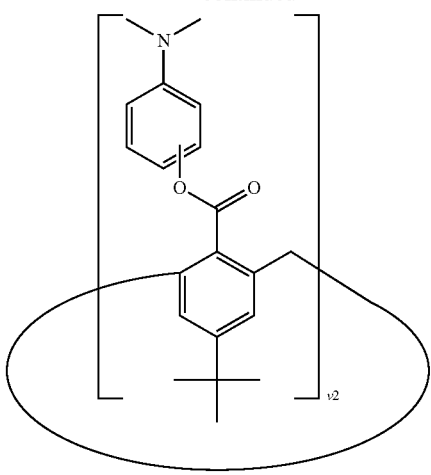
(The number of repetition v1 in the compound represented by the formula on the left represents an integer of 0 or more and 6 or less. The compound represented by the formula on the right is a calixarene, and the number of repetition v2 in the formula represents an integer of 4 or more and 8 or less.)
[Chem. 44]
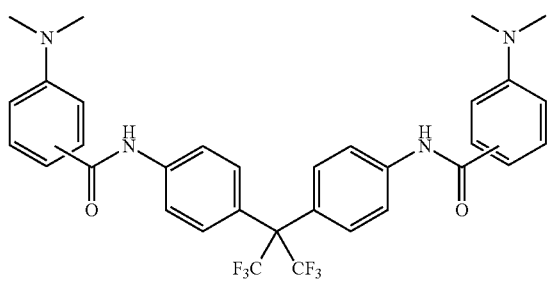
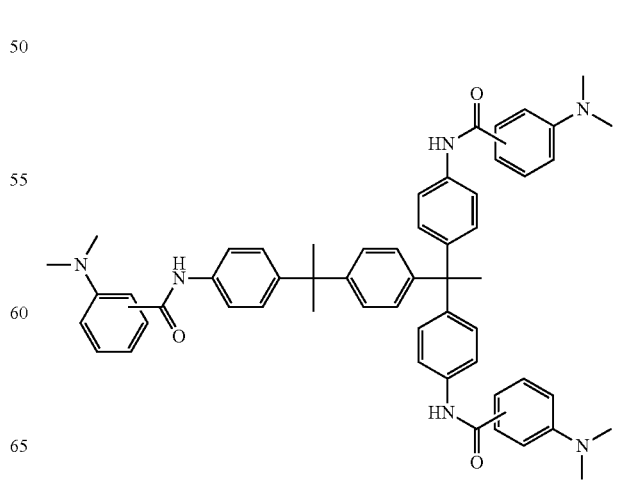

81
-continued
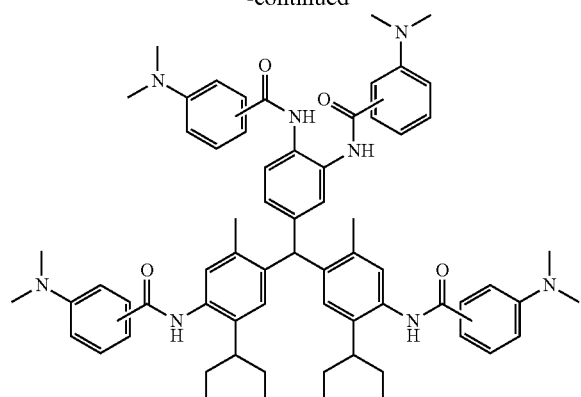
[Chem. 45]
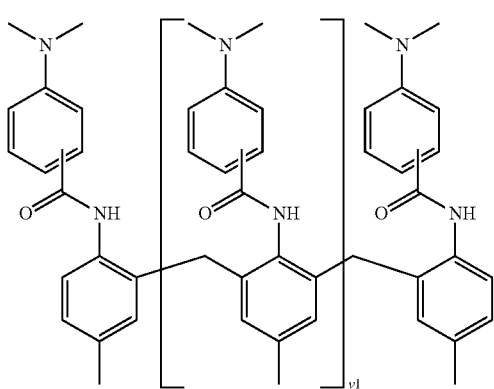
82
-continued
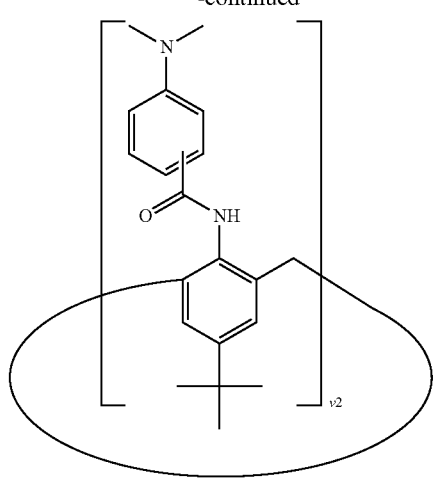
(The number of repetition v1 in the compound represented by the formula on the left represents an integer of 0 or more and 6 or less. The compound represented by the formula on the right is a calixarene, and the number of repetition v2 in the formula represents an integer of 4 or more and 8 or less.)
[Chem. 46]
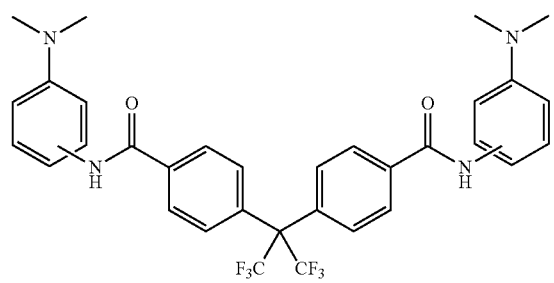
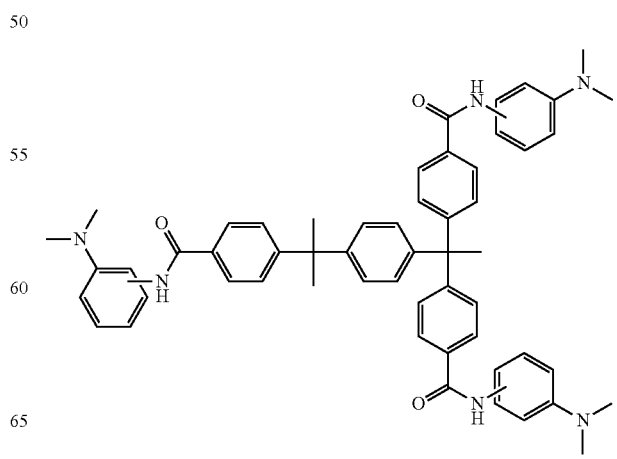

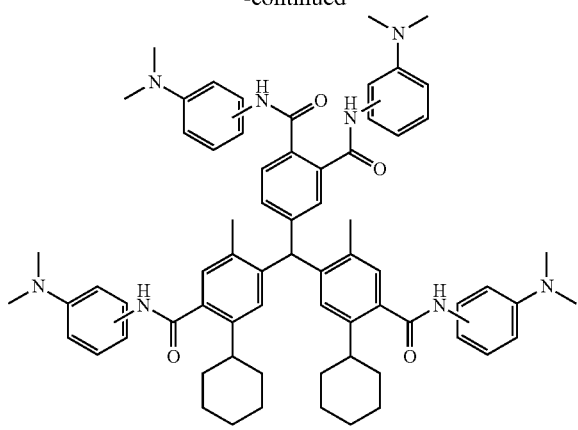

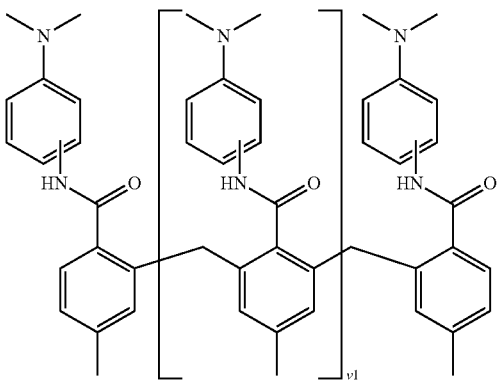

[Chem. 47]

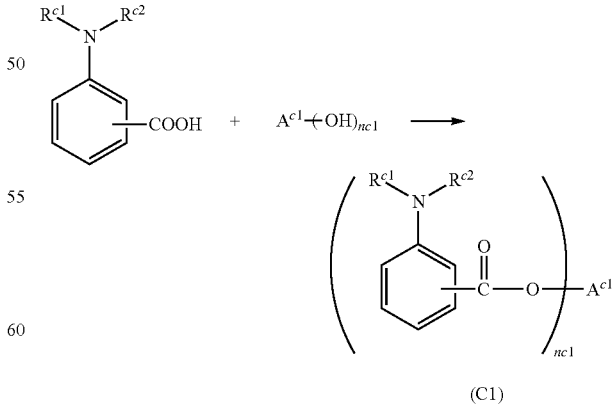

(The number of repetition v1 in the compound represented by the formula on the left represents an integer of 0 or more and 6 or less. The compound represented by the formula on the right is a calixarene, and the number of repetition v2 in the formula represents an integer of 4 or more and 8 or less.)

Furthermore, the specific examples of the above compound show an example in which $L^{c1}$ is —COO— or —CONH—. However, the specific examples of the compound represented by the above formula (C1) also include compounds in which all or a part of —COO—, or —CONH— is changed to a single bond, or —O—, —CO—, —OCOO—, —NH—, —NHCONH—, —S—, —SO—, or —SO$_2$— in the above compound.

The compound represented by the formula (C1) can be synthesized by appropriately combining well-known reactions. Hereinafter, examples of methods of synthesizing the compound represented by the formula (C1) are shown.

A compound represented by the formula (C1) wherein $L^{c1}$ is —COO—, and an oxygen atom of the —COO— is bonded to $A^{c1}$ can be synthesized by an esterification reaction between a carboxylic acid compound represented by the following formula and alcohol.

[Chem. 48]

A compound represented by the formula (C1) wherein $L^{c1}$ is —COO—, and a carbon atom of the —COO— is bonded to $A^{c1}$ can be synthesized by an esterification reaction between a carboxylic acid compound represented by the following formula and alcohol.

[Chem. 49]

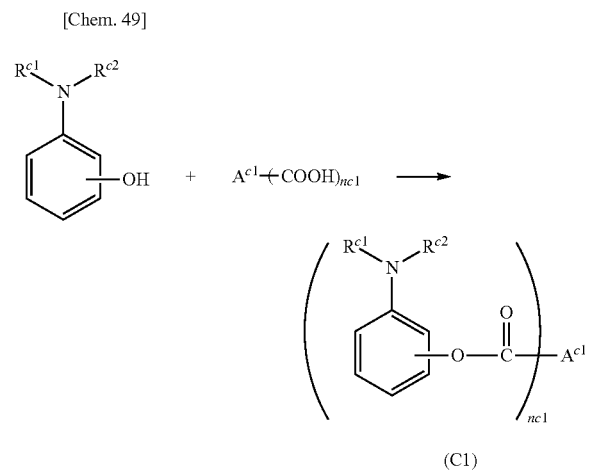

(C1)

The method of esterification is not particularly limited. Suitable examples of the esterification method include a method of reacting a condensing agent such as a carbodiimide compound (WSC) in the presence of catalyst such as N,N-dimethyl-4-amino pyridine, and condensing a carboxylic acid compound and alcohol. Furthermore, after the carboxylic acid compound is reacted with a halogenating agent such as thionyl chloride and phosphorus trichloride to produce carboxylic acid halide, and reacted with alcohol.

A compound represented by the formula (C1) wherein $L^{c1}$ is —CONH—, and a nitrogen atom of the —CONH— is bonded to $A^{c1}$ can be synthesized by an amidation reaction between a carboxylic acid compound represented by the following formula and amine.

[Chem. 50]

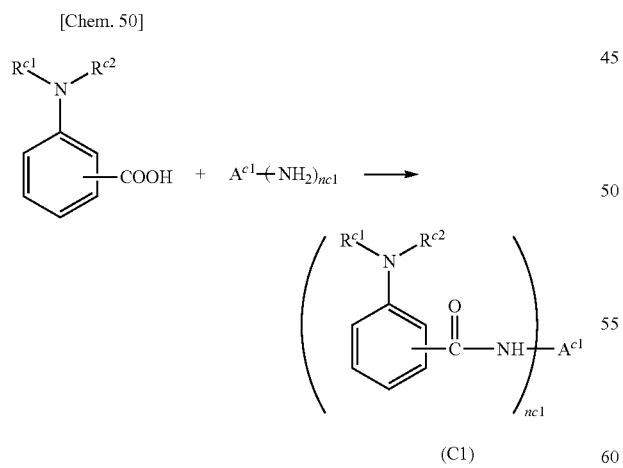

(C1)

A compound represented by the formula (C1) wherein $L^{c1}$ is —CONH—, and a carbon atom of the —CONH— is bonded to $A^{c1}$ can be synthesized by an amidation reaction between a carboxylic acid compound represented by the following formula and amine.

[Chem. 51]

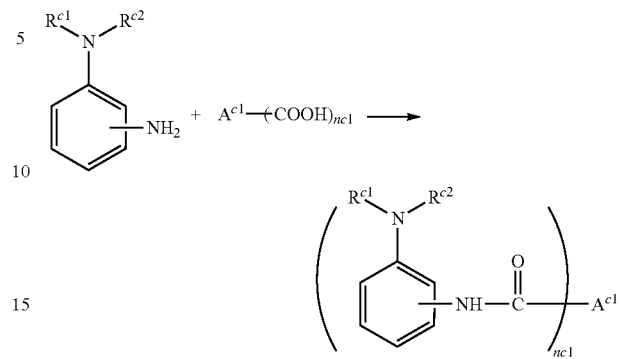

(C1)

The method of amidation is not particularly limited. Suitable examples of the amidation method include a method of reacting a condensing agent such as a carbodiimide compound (WSC), and condensing a carboxylic acid compound, halide of the carboxylic acid compound and acid anhydride of the carboxylic acid compound and amine. The condensation reaction may be carried out in the presence of catalyst such as N,N-dimethyl-4-amino pyridine as necessary.

Raw materials in the above esterification and amidation reactions are not particularly limited, but, for example, polyhydric phenol compounds as shown below. Furthermore, as raw materials in the above esterification and amidation reactions, commercial products may be used.

[Chem. 52]

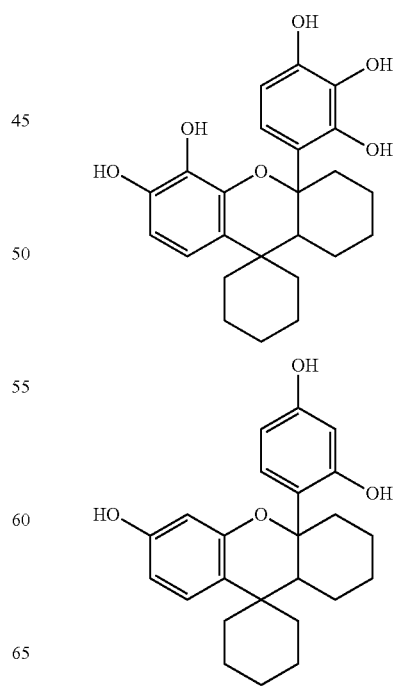

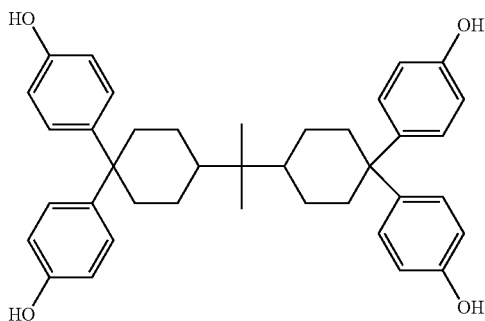
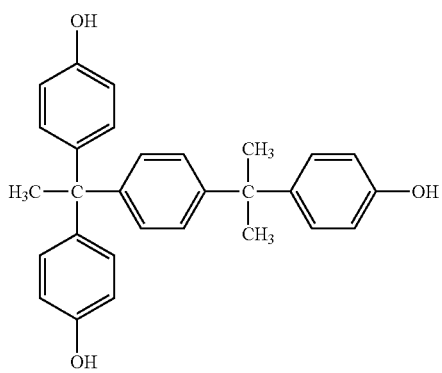
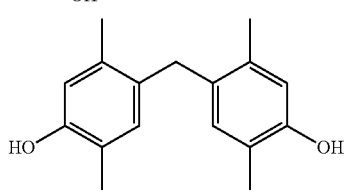
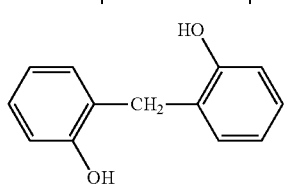
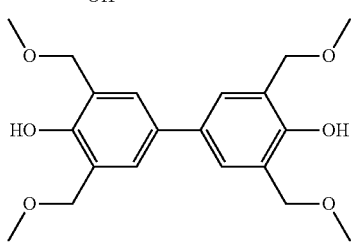
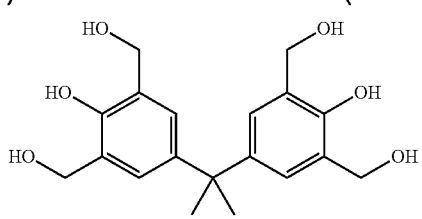
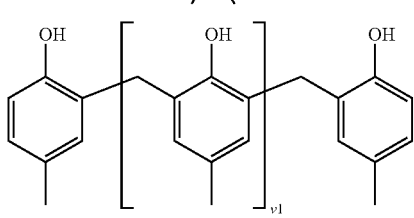

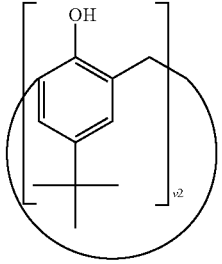

(The number of repetition v1 in the compound represented by the formula on the lower left represents an integer of 0 or more and 6 or less. The compound represented by the formula on the lower right is a calixarene, and the number of repetition v2 in the formula represents an integer of 4 or more and 8 or less.)

As mentioned above, with respect to method for manufacturing the compound represented by the formula (C1), method in a case where $L^{c1}$ is an ester bond or a carboxylic acid amide bonding was described. Note here that also in a case where $L^{c1}$ is a bond other than an ester bond and a carboxylic acid amide, the compound represented by the formula (C1) can be manufactured by applying well-known methods including an ether bond formation reaction, an acylation reaction, a carbonate bond formation reaction, an N-substituent introduction reaction into an amino group, an urethane bond formation reaction, a thioether bond formation reaction, a sulfoxide bond formation reaction (for example, oxidation of the thioether bond), and a sulfone bond formation reaction.

The compound represented by the formula (C1) is used in the amount in a range of preferably 0.01 parts by mass or more and 5 parts by mass or less, more preferably 0.01 parts by mass or more and 3 parts by mass or less, further preferably 0.05 part by mass or more and 2 parts by mass or less, relative to 100 parts by mass of the total mass of the above resin (B) and an alkali soluble resin (D) mentioned later.

Note here that the acid diffusion suppressing agent (C) may include an acid diffusion suppressing agent other than the above compound represented by the formula (C1), but the content of the compound represented by the formula (C1) in the acid diffusion suppressing agent (C) is preferably 50% by mass or more, more preferably 80% by mass or more, and further preferably 100% by mass.

<Acid Diffusion Suppressing Agent (C')>

The acid diffusion suppressing agent other than the compound represented by the formula (C1) is preferably a nitrogen-containing compound (C'1) other than the compound represented by the formula (C1), and an organic carboxylic acid, or an oxo acid of phosphorus or a derivative thereof (C'2) may be further included as needed.

[Nitrogen-Containing Compound (C'1)]

Examples of the nitrogen-containing compound (C'1) include trimethylamine, diethylamine, triethylamine, di-n-propylamine, tri-n-propylamine, tri-n-pentylamine, tribenzylamine, diethanolamine, triethanolamine, n-hexylamine, n-heptyl amine, n-octyl amine, n-nonyl amine, ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, formamide, N-methylformamide, N,N-dimethylformamide, acetamide, N-methylacetamide, N,N-dimethylacetamide, propionamide, benzamide, pyrrolidone, N-methylpyrrolidone, methylurea, 1,1-dimethylurea, 1,3-dimethylurea, 1,1,3,3,-tetramethylurea, 1,3-diphenylurea, imidazole, benzimidazole, 4-methylimidazole, 8-oxyquinoline, acridine, purine, pyrrolidine, piperidine, 2,4,6-tri(2-pyridyl)-S-triazine, morpholine, 4-methylmorpholine, piperazine, 1,4-dimethylpiperazine, 1,4-diazabicyclo[2.2.2]octane and pyridine, and pyridines. These may be used alone, or in combinations of two or more thereof.

Furthermore, commercially available hindered amine compounds such as Adeka Stab LA-52, Adeka Stab LA-57, Adeka Stab LA-63P, Adeka Stab LA-68, Adeka Stab LA-72, Adeka Stab LA-77Y, Adeka Stab LA-77G, Adeka Stab LA-81, Adeka Stab LA-82, Adeka Stab LA-87 (all manufactured by ADEKA), and the like, and pyridine whose 2,6-position has been substituted with a substituent a hydrocarbon group such as 2,6-diphenyl pyridine and 2,6-di-tert-butyl pyridine can be used as the nitrogen-containing compound (C'1).

The nitrogen-containing compound (C'1) may be used in an amount typically in the range of 0 parts by mass or more and 5 parts by mass or less, and particularly preferably in the range of 0 parts by mass or more and 3 parts by mass or less, with respect to 100 parts by mass of total mass of the above resin (B) and the above alkali-soluble resin (D).

[Organic Carboxylic Acid or Oxo Acid of Phosphorus or Derivative Thereof (C'2)]

Among the organic carboxylic acid, or the oxo acid of phosphorus or the derivative thereof (C'2), specific preferred examples of the organic carboxylic acid include malonic acid, citric acid, malic acid, succinic acid, benzoic acid, salicylic acid and the like, and salicylic acid is particularly preferred.

Examples of the oxo acid of phosphorus or derivatives thereof include phosphoric acid and derivatives such as esters thereof such as phosphoric acid, phosphoric acid di-n-butyl ester, and phosphoric acid diphenyl ester; phosphonic acid and derivatives such as esters thereof such as phosphonic acid, phosphonic acid dimethyl ester, phosphonic acid di-n-butyl ester, phenylphosphonic acid, phosphonic acid diphenyl ester, and phosphonic acid dibenzyl ester; and phosphinic acid and derivatives such as esters thereof such as phosphinic acid and phenylphosphinic acid; and the like. Among these, phosphonic acid is particularly preferred. These may be used alone, or in combinations of two or more thereof.

The organic carboxylic acid or oxo acid of phosphorus or derivative thereof (C'2) may be used in an amount usually in the range of 0 parts by mass or more and 5 parts by mass or less, and particularly preferably in the range of 0 parts by mass and 3 parts by mass or less, with respect to 100 parts by mass of total mass of the above resin (B) and the above alkali-soluble resin (D).

Moreover, in order to form a salt to allow for stabilization, the organic carboxylic acid, or the oxo acid of phosphorous or the derivative thereof (C'2) is preferably used in an amount equivalent to that of the above nitrogen-containing compound (C'1).

<Alkali-Soluble Resin (D)>

It is preferred that the positive-type photosensitive composition further contains an alkali-soluble resin (D) in order to improve crack resistance. The alkali-soluble resin as referred to herein may be determined as follows. A solution of the resin having a resin concentration of 20% by mass (solvent: propylene glycol monomethyl ether acetate) is used to form a resin film having a thickness of 1 μm on a substrate, and immersed in an aqueous 2.38% by mass TMAH (tetramethylammonium hydroxide) solution for 1 min. When the resin was dissolved in an amount of 0.01 μm or more, the resin is defined as being alkali soluble. As the alkali-soluble resin (D), at least one selected from the group consisting of novolak resin (D1), polyhydroxystyrene resin (D2), and acrylic resin (D3) are preferable.

[Novolak Resin (D1)]

A novolak resin is prepared by addition condensation of, for example, aromatic compounds having a phenolic hydroxyl group (hereinafter, merely referred to as "phenols") and aldehydes in the presence of an acid catalyst.

Examples of the above phenols include phenol, o-cresol, m-cresol, p-cresol, o-ethylphenol, m-ethylphenol, p-ethylphenol, o-butylphenol, m-butylphenol, p-butylphenol, 2,3-xylenol, 2,4-xylenol, 2,5-xylenol, 2,6-xylenol, 3,4-xylenol, 3,5-xylenol, 2,3,5-trimethyl phenol, 3,4,5-trimethyl phenol, p-phenylphenol, resorcinol, hydroquinone, hydroquinone monomethyl ether, pyrogallol, phloroglycinol, hydroxydiphenyl, bisphenol A, gallic acid, gallic acid ester, α-naphthol, P-naphthol, and the like. Examples of the above aldehydes include formaldehyde, furfural, benzaldehyde, nitrobenzaldehyde, acetaldehyde, and the like. The catalyst used in the addition condensation reaction is not particularly limited, and examples thereof include hydrochloric acid, nitric acid, sulfuric acid, formic acid, oxalic acid, acetic acid, etc., for acid catalyst.

The flexibility of the novolak resins can be enhanced more when o-cresol is used, a hydrogen atom of a hydroxyl group in the resins is substituted with other substituents, or bulky aldehydes are used.

The mass average molecular weight of novolac resin (D1) is not particularly limited as long as the purpose of the present invention is not impaired, but the mass average molecular weight is preferably 1,000 or more and 50,000 or less.

[Polyhydroxystyrene Resin (D2)]

The hydroxystyrene compound to constitute the polyhydroxystyrene resin (D2) is exemplified by p-hydroxystyrene, α-methylhydroxystyrene, α-ethylhydroxystyrene, and the like. Furthermore, the polyhydroxystyrene resin (D2) is preferably prepared to give a copolymer with a styrene resin. Examples of the styrene compound to constitute such a styrene resin include styrene, chlorostyrene, chloromethylstyrene, vinyltoluene, α-methylstyrene, and the like.

The mass average molecular weight of the polyhydroxystyrene resin (D2) is not particularly limited as long as the purpose of the present invention is not impaired, but the mass average molecular weight is preferably 1,000 or more and 50,000 or less.

[Acrylic Resin (D3)]

It is preferable that the acrylic resin (D3) includes a constituent unit derived from a polymerizable compound having an ether bond and a constituent unit derived from a polymerizable compound having a carboxyl group.

Examples of the above polymerizable compound having an ether bond include (meth)acrylic acid derivatives having an ether bond and an ester bond such as 2-methoxyethyl (meth)acrylate, methoxytriethylene glycol (meth)acrylate, 3-methoxybutyl (meth)acrylate, ethylcarbitol (meth)acrylate, phenoxypolyethylene glycol (meth)acrylate, methoxypolypropylene glycol (meth)acrylate, tetrahydrofurfuryl (meth)acrylate, and the like. The above polymerizable compound having an ether bond is preferably, 2-methoxyethyl acrylate, and methoxytriethylene glycol acrylate. These polymerizable compounds may be used alone, or in combinations of two or more.

Examples of the above polymerizable compound having a carboxy group include monocarboxylic acids such as acrylic acid, methacrylic acid and crotonic acid; dicarboxylic acids such as maleic acid, fumaric acid and itaconic acid; compounds having a carboxy group and an ester bond such as 2-methacryloyloxyethyl succinic acid, 2-methacryloyloxyethyl maleic acid, 2-methacryloyloxyethyl phthalic acid, 2-methacryloyloxyethyl hexahydrophthalic acid and the like. The above polymerizable compound having a carboxy group is preferably, acrylic acid and methacrylic acid. These polymerizable compounds may be used alone, or in combinations of two or more thereof.

The mass average molecular weight of the acrylic resin (D3) is not particularly limited as long as the purpose of the present invention is not impaired, but the mass average molecular weight is preferably 50,000 or more and 800,000 or less.

The content of the alkali-soluble resin (D) is such that when the total amount of the above resin (B) and the alkali-soluble resin (D) is taken as 100 parts by mass, the content is preferably 0 parts by mass or more and 80 parts by mass or less, and more preferably 0 parts by mass or more and 60 parts by mass or less. By setting the content of the alkali-soluble resin (D) to the range described above, there is a tendency for resistance to cracking to increase, and film loss at the time of development can be prevented.

<Sulfur-Containing Compound (E)>

When a photosensitive composition is used for pattern formation on a metal substrate, the photosensitive composition preferably includes a sulfur-containing compound (E). The sulfur-containing compound (E) is a compound including a sulfur atom that can coordinate with metal. Note here that in a compound that can generate two or more tautomers, at least one tautomer includes a sulfur atom that coordinates with metal constituting a metal substrate surface, the compound corresponds to a sulfur-containing compound. When a resist pattern serving as a template for plating is formed on a surface made of metal such as Cu, defectives such as footing having a cross-sectional shape may occur. As described above, when the above photosensitive composition is used, a resist pattern whose cross-sectional shape of nonresist section is rectangular is formed easily. On the other hand, in order to inhibit defectives of the cross-sectional shape more reliably, the photosensitive composition preferably includes a sulfur-containing compound (E). When the photosensitive composition includes a sulfur-containing compound (E), even when a resist pattern is formed on a surface made of metal in a substrate, defectives such as footing having a cross-sectional shape is easily suppressed more reliably. Note here that the "footing" is a phenomenon in which the width of the bottom becomes narrower than that of the top in a nonresist section due to protrusion of a resist section toward the nonresist section in the vicinity of the contacting surface between the substrate surface and the resist pattern. When the photosensitive composition is used for pattern formation on a substrate other than the metal substrate, the photosensitive composition does not specially need to include a sulfur-containing compound. When the photosensitive composition is used for pattern formation on the substrate other than the metal substrate, it is preferable that the photosensitive composition does not include a sulfur-containing compound (E) from the viewpoint that reduction of the number of components in the photosensitive composition makes manufacturing the photosensitive composition easier, and reduces the manufacturing cost of the photosensitive composition, and the like. Note here that there is no particular deficiency resulting from the inclusion of a sulfur-containing compound (E) in the photosensitive composition to be used for formation of pattern on the substrate other than the metal substrate.

The sulfur atom that can coordinate with metal is included in a sulfur-containing compound as, for example, a mercapto group (—SH), a thiocarboxy group (—CO—SH), a dithiocarboxy group (—CS—SH), a thiocarbonyl group (—CS—), and the like. From the viewpoint of easiness in coordinating with metal and being excellent in suppressing footing, the sulfur-containing compound preferably includes a mercapto group.

Preferable examples of the sulfur-containing compound having a mercapto group include compounds represented by the following formula (e1).

[Chem. 53]

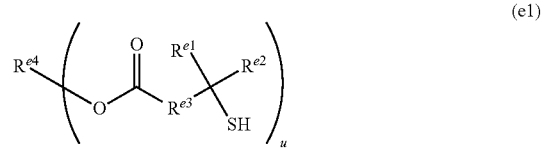

(In the formula, $R^{e1}$ and $R^{e2}$ each independently represent a hydrogen atom or an alkyl group, $R^{e3}$ represents a single bond or an alkylene group, $R^{e4}$ represents a u-valence aliphatic group which may include an atom other than carbon, and u is an integer of 2 or more and 4 or less.)

$R^{e1}$ and $R^{e2}$ are an alkyl group, the alkyl group may be linear or branched, and is preferably linear. When $R^{e1}$ and $R^{e2}$ are an alkyl group, the number of carbon atoms of the alkyl group is not particularly limited within a range where the objects of the present invention are not impaired. The number of carbon atoms of the alkyl group is preferably 1 or more and 4 or less, particularly preferably 1 or 2, and the most preferably 1. As the combination of $R^{e1}$ and $R^{e2}$, preferably, one is a hydrogen atom and the other is an alkyl group, and particularly preferably one is a hydrogen atom and the other is a methyl group.

When $R^{e3}$ is an alkylene group, the alkylene group may be linear or branched, and is preferably linear. When $R^{e3}$ is an alkylene group, the number of carbon atoms of the alkylene group is not particularly limited within a range where the objects of the present invention are not impaired. The number of carbon atoms of the alkylene group is preferably 1 or more and 10 or less, more preferably 1 or more and 5 or less, particularly preferably 1 or 2, and the most preferably 1.

$R^{e4}$ is an aliphatic group having two or more and four or less valences and which may include an atom other than carbon atom. Examples of the atoms which may be included in $R^{e4}$ include a nitrogen atom, an oxygen atom, a sulfur atom, a fluorine atom, a chlorine atom, a bromine atom, an iodine atom, and the like. A structure of the aliphatic group as $R^{e4}$ may be linear or branched, or may be cyclic, and a structure combining these structures.

Among the compounds represented by the formula (e1), a compound represented by the following formula (e2) is more preferable.

[Chem. 54]

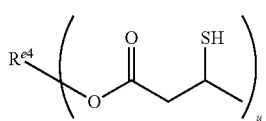

(In the formula (e2), $R^{e4}$ and u are the same as those in the formula (e1).)

Among the compounds represented by the above formula (e2), the following compounds are preferable.

[Chem. 55]

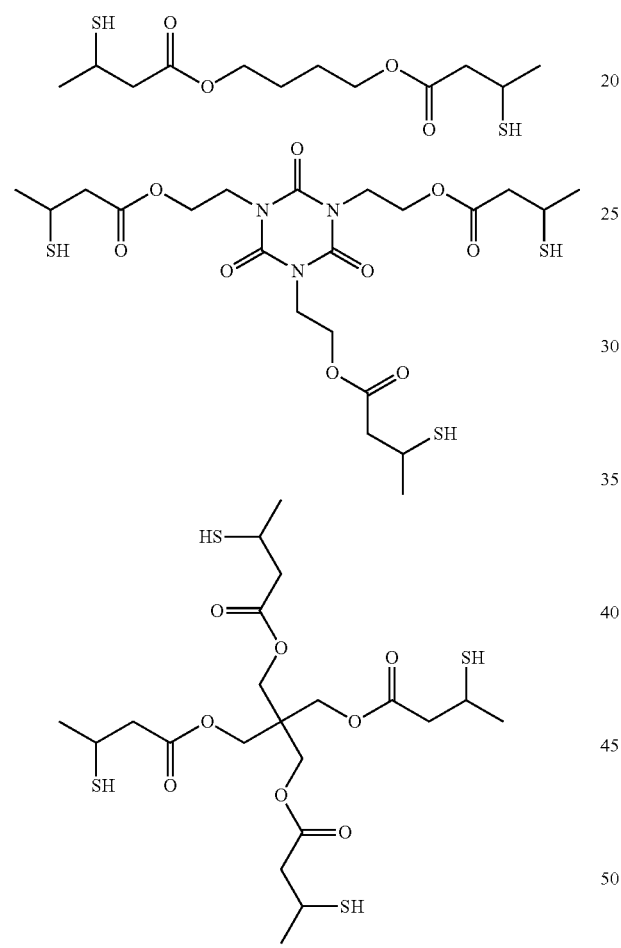

Compounds represented by the following formulae (e3-L1) to (e3-L7) are also preferable examples as the sulfur-containing compound having a mercapto group.

[Chem. 56]

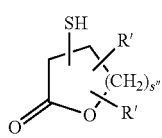 (e3-L1)

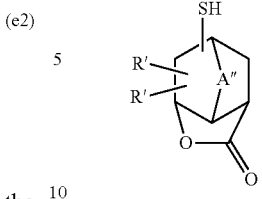 (e3-L2)

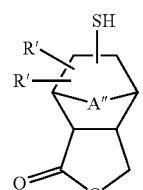 (e3-L3)

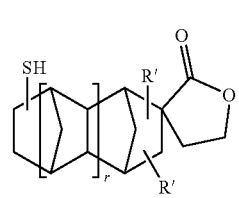 (e3-L4)

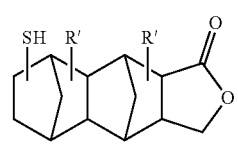 (e3-L5)

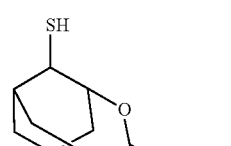 (e3-L6)

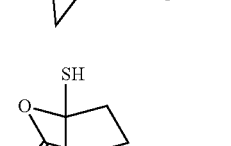 (e3-L7)

(In the formulae (e3-L1) to (e3-L7), R', s", A", and r are the same as in the formulae (b-L1) to (b-L7) described for the acrylic resin (B3).)

Suitable specific examples of the mercapto compound represented by the above formulae (e3-L1) to (e3-L7) include the following compounds.

[Chem. 57]

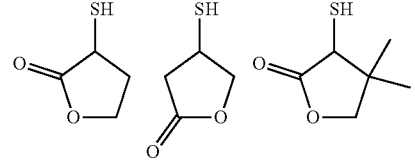

-continued
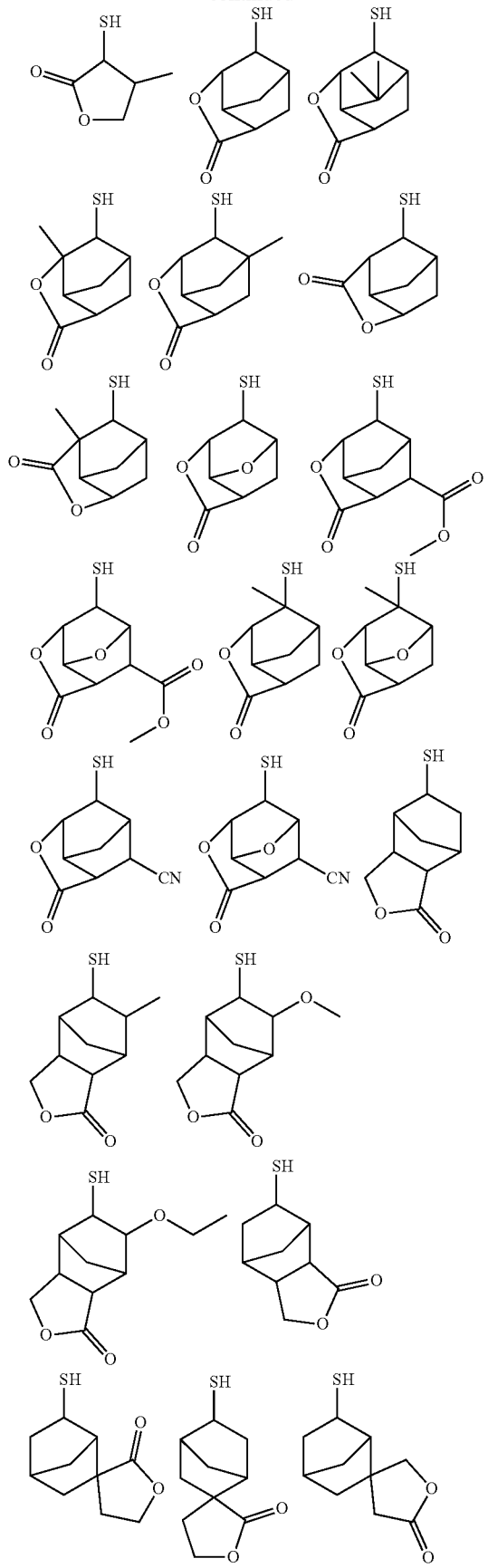
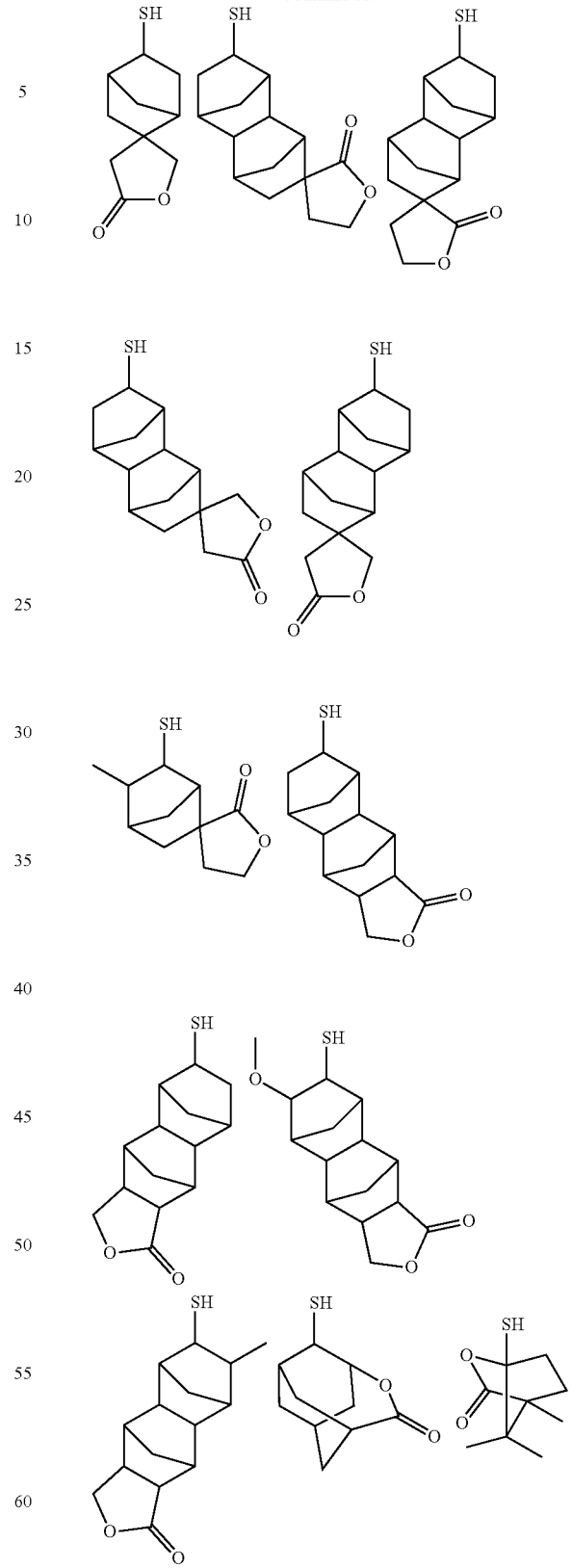
Compounds represented by the following formulae (e3-1) to (e3-4) are also preferable examples as the sulfur-containing compound having a mercapto group.

[Chem. 58]
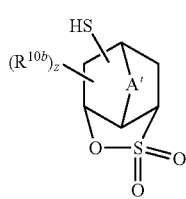 (e3-1)
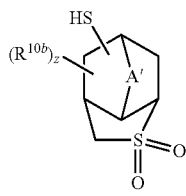 (e3-2)
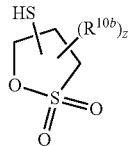 (e3-3)
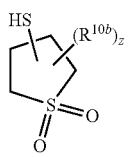 (e3-4)
(In the formulae (e3-1) to (e3-4), definitions of abbreviations are the same as mentioned for the formulae (3-1) to (3-4) described for acrylic resin (B3).)
Suitable specific examples of the mercapto compound represented by the above formulae (e3-1) to (e3-4) include the following compounds.
[Chem. 59]
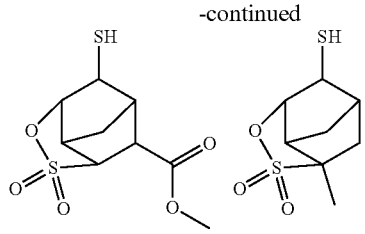
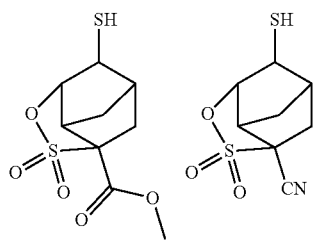
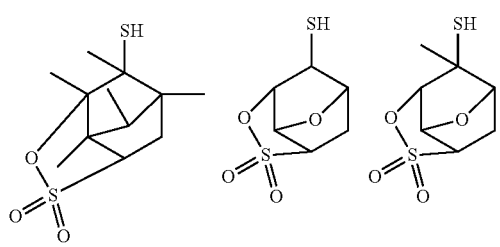
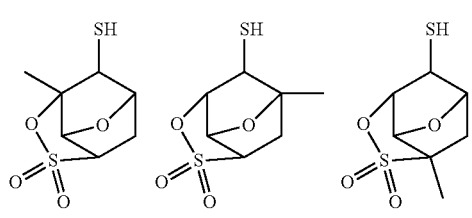
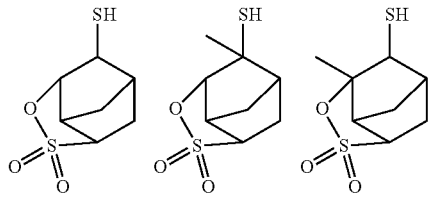
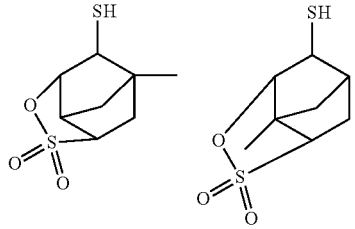
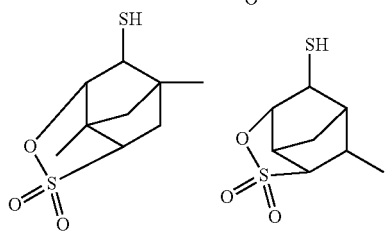
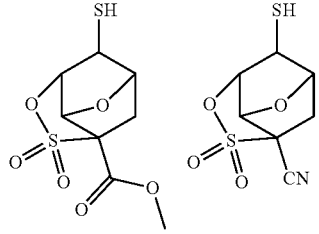
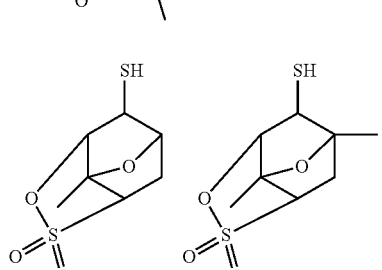
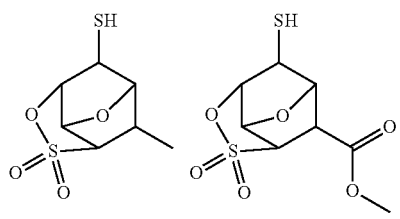

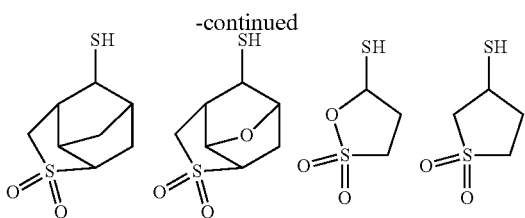

Furthermore, preferable examples of the compound having a mercapto group include compounds represented by the following formula (e4).

[Chem. 60]

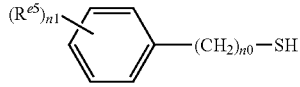

(In the formula (e4), $R^{e5}$ is a group selected from the group consisting of a hydroxyl group, an alkyl group having 1 or more 4 or less carbon atoms, an alkoxy group having 1 or more 4 or less carbon atoms, an alkylthio group having 1 or more and 4 or less carbon atoms, a hydroxyalkyl group having 1 or more and 4 or less carbon atoms, a mercapto alkyl group having 1 or more and 4 or less carbon atoms, a halogenated alkyl group having 1 or more and 4 or less carbon atoms, and a halogen atom, n1 is an integer of 0 or more and 3 or less, n0 is an integer of 0 or more and 3 or less, when n1 is 2 or 3, $R^{e5}$ may be the same as or different from each other.)

Specific examples when $R^{e5}$ is an alkyl group which may have a hydroxyl group having 1 or more 4 or less carbon atoms include a methyl group, an ethyl group, an n-propyl group, an isopropyl group, an n-butyl group, an isobutyl group, a sec-butyl group, and a tert-butyl group. Among these alkyl groups, a methyl group, a hydroxymethyl group, and an ethyl group are preferable.

Specific examples when $R^{e5}$ is an alkoxy group having 1 or more 4 or less carbon atoms include a methoxy group, an ethoxy group, an n-propyloxy group, an isopropyloxy group, an n-butyloxy group, an isobutyloxy group, a sec-butyloxy group, and a tert-butyloxy group. Among these alkoxy groups, a methoxy group and an ethoxy group are preferable, and a methoxy group is more preferable.

Specific examples when $R^{e5}$ is an alkylthio group having 1 or more 4 or less carbon atoms include a methylthio group, an ethylthio group, an n-propylthio group, an isopropylthio group, an n-butylthio group, an isobutylthio, a sec-butylthio group, and a tert-butylthio group. Among these alkylthio groups, a methylthio group, and an ethylthio group are preferable, and a methylthio group is more preferable.

Specific examples when $R^{e5}$ is a hydroxyalkyl group having 1 or more 4 or less carbon atoms include a hydroxymethyl group, a 2-hydroxyethyl group, a 1-hydroxyethyl group, a 3-hydroxy-n-propyl group, and a 4-hydroxy-n-butyl group, and the like. Among these hydroxyalkyl groups, a hydroxymethyl group, a 2-hydroxyethyl group, and a 1-hydroxyethyl group are preferable, and a hydroxymethyl group is more preferable.

Specific examples when $R^{e5}$ is a mercapto alkyl group having 1 or more 4 or less carbon atoms include a mercapto methyl group, a 2-mercapto ethyl group, a 1-mercapto ethyl group, a 3-mercapto-n-propyl group, a 4-mercapto-n-butyl group, and the like. Among these mercapto alkyl groups, a mercapto methyl group, a 2-mercapto ethyl group, and 1-mercapto ethyl group are preferable, and a mercapto methyl group is more preferable.

When $R^{e5}$ is an alkyl halide group having 1 or more 4 or less carbon atoms, examples of the halogen atom included in the alkyl halide group include fluorine, chlorine, bromine, iodine, and the like. Specific examples when $R^{e5}$ is an alkyl halide group having 1 or more 4 or less carbon atoms include a chloromethyl group, a bromomethyl group, an iodomethyl group, a fluoromethyl group, a dichloromethyl group, a dibromomethyl group, a difluoromethyl group, a trichloromethyl group, a tribromomethyl group, a trifluoromethyl group, a 2-chloroethyl group, a 2-bromoethyl group, a 2-fluoroethyl group, a 1,2-dichloroethyl group, a 2,2-difluoroethyl group, a 1-chloro-2-fluoroethyl group, 3-chloro-n-propyl group, a 3-bromon-propyl group, a 3-fluoro-n-propyl group, 4-chloro-n-butyl group, and the like. Among these alkyl halide groups, a chloromethyl group, a bromomethyl group, an iodomethyl group, a fluoromethyl group, a dichloromethyl group, a dibromomethyl group, a difluoromethyl group, a trichloromethyl group, a tribromomethyl group, and a trifluoromethyl group are preferable, and a chloromethyl group, a dichloromethyl group, a trichloromethyl group, and a trifluoromethyl group are more preferable.

Specific examples when $R^{e5}$ is a halogen atom include fluorine, chlorine, bromine, or iodine.

In the formula (e4), n1 is an integer of 0 or more 3 or less, and 1 is more preferable. When n1 is 2 or 3, a plurality of $R^{e5}$ may be the same as or different from each other.

In the compound represented by the formula (e4), a substituted position of $R^{e5}$ on a benzene ring is not particularly limited. The substituted position of $R^{e5}$ on a benzene ring is preferably a meta position or a para position with respect to the bond position of —$(CH_2)_{n0}$—SH.

The compound represented by the formula (e4) is preferably a compound having at least one group selected from the group consisting of an alkyl group, a hydroxyalkyl group, and a mercapto alkyl group as $R^{e5}$, and more preferably a compound having one group selected from the group consisting of an alkyl group, a hydroxyalkyl group, and a mercapto alkyl group as $R^{e5}$. When the compound represented by the formula (e4) has one group selected from the group consisting of an alkyl group, a hydroxyalkyl group, and a mercapto alkyl group as $R^{e5}$, the substituted position on the benzene ring of the alkyl group, the hydroxyalkyl group, or the mercapto alkyl group is preferably a meta position or a para position with respect to the bond position of —$(CH_2)_{n0}$—SH, and more preferably a para position.

In the formula (e4), n0 is an integer of 0 or more 3 or less. From the viewpoint that preparation or availability of a compound is easy, n0 is preferably 0 or 1, and more preferably 0.

Specific examples of the compound represented by the formula (e4) include p-mercaptophenol, p-thiocresol, m-thiocresol, 4-(methylthio)benzenethiol, 4-methoxybenzenethiol, 3-methoxybenzenethiol, 4-ethoxybenzenethiol, 4-isopropyloxy benzenethiol, 4-tert-butoxybenzenethiol, 3,4-dimethoxy benzenethiol, 3,4,5-trimethoxybenzenethiol, 4-ethylbenzenethiol, 4-isopropyl benzenethiol, 4-n-butylbenzenethiol, 4-tert-butylbenzenethiol, 3-ethylbenzenethiol, 3-isopropyl benzenethiol, 3-n-butylbenzenethiol, 3-tert-butylbenzenethiol, 3,5-dimethyl benzenethiol, 3,4-dimethyl benzenethiol, 3-tert-butyl-4-methylbenzenethiol, 3-tert-4-methylbenzenethiol, 3-tert-butyl-5-methylbenzenethiol, 4-tert-butyl-3-methylbenzenethiol, 4-mercaptobenzyl alcohol, 3-mercaptobenzyl alcohol, 4-(mercaptomethyl)phenol, 3-(mercaptomethyl)phenol, 1,4-di(mercaptomethyl)phenol, 1,3-di(mercaptomethyl)phenol, 4-fluorobenzenethiol, 3-fluorobenzenethiol, 4-chlorobenzenethiol, 3-chlorobenzenethiol, 4-bromobenzenethiol, 4-iodobenzenethiol, 3-bromobenzenethiol, 3,4-dichlorobenzenethiol, 3,5-dichlorobenzenethiol, 3,4-difluorobenzenethiol, 3,5-difluorobenzenethiol, 4-mercaptocatechol, 2,6-di-tert-butyl-4-mercaptophenol, 3,5-di-tert-butyl-4-methoxybenzenethiol, 4-bromo-3-methylbenzenethiol, 4-(trifluoromethyl)benzenethiol, 3-(trifluoromethyl)benzenethiol, 3,5-bis(trifluoromethyl)benzenethiol, 4-methylthiobenzenethiol, 4-ethylthiobenzenethiol, 4-n-butylthiobenzenethiol, and 4-tert-butylthiobenzenethiol, and the like.

Furthermore, examples of the sulfur-containing compound having a mercapto group include a compound including nitrogen-containing aromatic heterocycle substituted with a mercapto group, and a tautomer of a compound including nitrogen-containing aromatic heterocycle substituted with a mercapto group. Preferable specific examples of the nitrogen-containing aromatic heterocycle include imidazole, pyrazole, 1,2,3-triazol, 1,2,4-triazol, oxazole, thiazole, pyridine, pyrimidine, pyridazine, pyrazine, 1,2,3-triazine, 1,2,4-triazine, 1,3,5-triazine, indole, indazole, benzimidazole, benzoxazole, benzothiazole, 1H-benzotriazole, quinoline, isoquinoline, cinnoline, phthalazine, quinazoline, quinoxaline, and 1,8-naphthyridine.

Suitable specific examples of a nitrogen-containing heterocyclic compound suitable as a sulfur-containing compound, and suitable tautomer of the nitrogen-containing heterocyclic compound include the following compounds.

[Chem. 61]

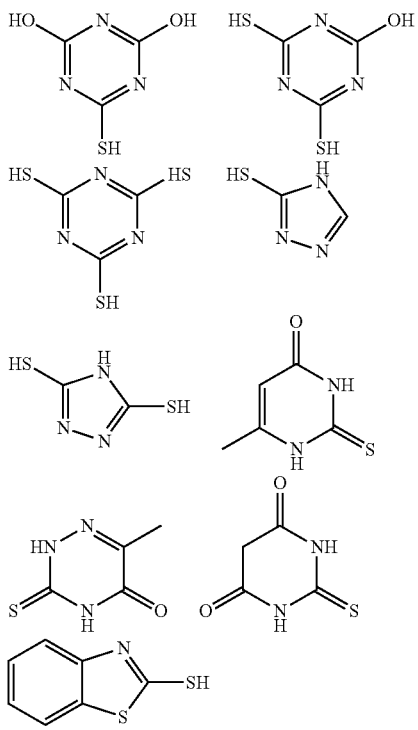

When the photosensitive composition includes a sulfur-containing compound (E), the use amount is preferably 0.01 parts by mass or more 5 parts by mass or less, more preferably 0.02 parts by mass or more 3 parts by mass or less, and particularly preferably 0.05 parts by mass or more 2 parts by mass or less with respect to 100 parts by mass that is the total mass of the above resin (B) and the alkali-soluble resin (D).

<Organic Solvent (S)>

The photosensitive composition contains an organic solvent (S). There is no particular limitation on the types of the organic solvent (S) as long as the objects of the present invention are not impaired, and an organic solvent appropriately selected from those conventionally used for positive-type photosensitive compositions can be used.

Specific examples of the organic solvent (S) include ketones such as acetone, methyl ethyl ketone, cyclohexanone, methyl isoamyl ketone, and 2-heptanone; polyhydric alcohols and derivatives thereof such as ethylene glycol, ethylene glycol monoacetate, diethylene glycol, diethylene glycol monoacetate, propylene glycol, propylene glycol monoacetate, dipropylene glycol, and a monomethyl ether, a monoethyl ether, a monopropyl ether, a monobutyl ether, and a monophenyl ether of dipropylene glycol monoacetate; cyclic ethers such as dioxane; esters such as ethyl formate, methyl lactate, ethyl lactate, methyl acetate, ethyl acetate, butyl acetate, methyl pyruvate, methyl acetoacetate, ethyl acetoacetate, ethyl pyruvate, ethylethoxy acetate, methyl methoxypropionate, ethyl ethoxypropionate, methyl 2-hydroxypropionate, ethyl 2-hydroxypropionate, ethyl 2-hydroxy-2-methylpropionate, methyl 2-hydroxy-3-methylbutanate, 3-methoxybutyl acetate, and 3-methyl-3-methoxybutyl acetate; aromatic hydrocarbons such as toluene and xylene; and the like. These may be used alone, or as a mixture of two or more thereof.

There is no particular limitation on the content of the organic solvent (S) as long as the objects of the present invention are not impaired. In a case where a photosensitive composition is used for a thick-film application such that a photosensitive layer obtained by the spin coating method and the like has a film thickness of 5 μm or more, the organic solvent (S) is preferably used in a range where the solid content concentration of the photosensitive composition is 30% by mass or more and 55% by mass or less.

<Other Components>

The photosensitive composition may further contain a polyvinyl resin for improving plasticity. Specific examples of the polyvinyl resin include polyvinyl chloride, polystyrene, polyhydroxystyrene, polyvinyl acetate, polyvinylbenzoic acid, polyvinyl methyl ether, polyvinyl ethyl ether, polyvinyl alcohol, polyvinyl pyrrolidone, polyvinyl phenol, and copolymers thereof, and the like. The polyvinyl resin is preferably polyvinyl methyl ether in view of lower glass transition temperatures.

It is also preferable that a photosensitive composition contains a Lewis acidic compound. When the photosensitive composition includes a Lewis acidic compound, a photosensitive composition with high sensitivity is easily obtained, so that a resist pattern whose cross-sectional shape is rectangular is more easily formed using a positive-type photosensitive composition. Furthermore, when a pattern is formed using the photosensitive composition, when time required for each process at the time of pattern formation or time required between the processes is long, a pattern having a desired shape and dimension may not be easily formed, or developing property may be deteriorated. However, when a Lewis acidic compound is blended into the photosensitive composition, such adverse effects on the pattern shape or the developing property can be mitigated or a process margin can be widened.

The Lewis acidic compound herein represents "a compound that acts as an electron-pair receptor having an empty orbital capable of receiving at least one electron pair." The Lewis acidic compound is not particularly limited as long as it corresponds to the above definition, and is a compound which is recognized as the Lewis acidic compound by a person skilled in the art. As the Lewis acidic compound, a compound that does not correspond to a Bronsted acid (proton acid) is preferably used. Specific examples of the Lewis acidic compound include boron fluoride, ether complexes of boron fluoride (for example, $BF_3.Et_2O$, $BF_3.Me_2O$, $BF_3$-THF, etc., Et represents an ethyl group, Me represents a methyl group, and THF represents tetrahydrofuran), organic boron compounds (for example, tri-n-octyl borate, tri-n-butyl borate, triphenyl borate, triphenylboron, etc.), titanium chloride, aluminum chloride, aluminum bromide, gallium chloride, gallium bromide, indium chloride, thallium trifluoroacetate, tin chloride, zinc chloride, zinc bromide, zinc iodide, zinc trifluoromethanesulfonate, zinc acetate, zinc nitrate, zinc tetrafluoroborate, manganese chloride, manganese bromide, nickel chloride, nickel bromide, nickel cyanide, nickel acetylacetonate, cadmium chloride, cadmium bromide, stannous chloride, stannous bromide, stannous sulfate, stannous tartrate, and the like. Furthermore, other specific examples of the Lewis acidic compound include chloride, bromide, sulfate, nitrate, carboxylate, or trifluoromethanesulfonate, of the rare earth metal element, and cobalt chloride, ferrous chloride, yttrium chloride, and the like. Examples of the rare earth metal element herein include lanthanum, cerium, praseodymium, neodymium, samarium, europium, gadolinium, terbium, dysprosium, holmium, erbium, thulium, ytterbium, and lutetium.

From the viewpoint of easiness in availability and favorable effect by addition thereof, it is preferable that the Lewis acidic compound contains a Lewis acidic compound including elements belonging to Group 13. Herein, examples of the elements belonging to Group 13 include boron, aluminum, gallium, indium, and thallium. Among the above elements belonging to Group 13, boron is preferable from the viewpoint that the Lewis acidic compound is easily available and addition effect is particularly excellent. In other words, it is preferable that the Lewis acidic compound contains a Lewis acidic compound including boron.

Examples of the Lewis acidic compound containing boron include boron fluoride, ether complexes of boron fluoride, boron halides such as boron chloride and boron bromide, and various organic boron compounds. As the Lewis acidic compound including boron, an organic boron compound is preferable because the content ratio of halogen atoms in the Lewis acidic compound is small and the photosensitive composition is easily applicable to an application requiring a low halogen content.

Preferable examples of the organic boron compound include a boron compound represented by the following formula (f1):

$$B(R^{f1})_{t1}(OR^{f2})_{(3-t1)} \quad (f1)$$

(In the formula (f1), $R^{f1}$ and $R^{f2}$ each independently represent a hydrocarbon group having 1 or more and 20 or less carbon atoms; the hydrocarbon group may have one or more substituents; t1 is an integer of 0 or more and 3 or less; when a plurality of $R^{f1}$ exists, two of the plurality of $R^{f1}$ may be bonded to each other to form a ring; and when a plurality of $OR^{f2}$ is present, two of the plurality of $OR^{f2}$ may be bonded to each other to form a ring). The photosensitive composition preferably includes one or more boron compounds represented by the above formula (f1) as the Lewis acidic compound mentioned above.

In the formula (f1), $R^{f1}$ and $R^{f2}$ are a hydrocarbon group, the number of carbon atoms of the hydrocarbon group is 1 or more and 20 or less. The hydrocarbon group having 1 or more and 20 or less carbon atoms may be an aliphatic hydrocarbon group, or an aromatic hydrocarbon group, a hydrocarbon group having a combination of an aliphatic group and an aromatic group. As the hydrocarbon group having 1 or more and 20 or less carbon atoms, a saturated aliphatic hydrocarbon group, or an aromatic hydrocarbon group is preferable. The number of carbon atoms of the hydrocarbon group as $R^{f1}$ and $R^{f2}$ is preferably 1 or more and 10 or less. When the hydrocarbon group is an aliphatic hydrocarbon group, the number of carbon atoms thereof is preferably 1 or more and 6 or less, and particularly preferably 1 or more and 4 or less. The hydrocarbon group as $R^{f1}$ and $R^{f2}$ may be a saturated hydrocarbon group, or an unsaturated hydrocarbon group, and a saturated hydrocarbon group is preferable. When the hydrocarbon group as $R^{f1}$ and $R^{f2}$ is an aliphatic hydrocarbon group, the aliphatic hydrocarbon group may be linear, branched or cyclic or combination thereof.

Suitable specific examples of aromatic hydrocarbon groups include a phenyl group, a naphthalene-1-yl group, a naphthalene-2-yl group, a 4-phenylphenyl, 3-phenylphenyl, and 2-phenylphenyl. Among them, a phenyl group is preferable.

The saturated aliphatic hydrocarbon group is preferably an alkyl group. Suitable examples of alkyl groups include a methyl group, an ethyl group, an n-propyl group, an isopropyl group, an n-butyl group, an isobutyl group, a sec-butyl group, a tert-butyl group, an n-pentyl group, an n-hexyl group, an n-heptyl group, an n-octyl group, a 2-ethyl hexyl group, an n-nonyl group, and an n-decyl group.

The hydrocarbon group as $R^{f1}$ and $R^{f2}$ may have one or more substituents. Examples of the substituent include a halogen atom, a hydroxyl group, an alkyl group, an aralkyl group, an alkoxy group, a cycloalkyloxy group, an aryloxy group, an aralkyloxy group, an alkylthio group, a cycloalkylthio group, an arylthio group, an aralkylthio group, an acyl group, an acyloxy group, an acylthio group, an alkoxycarbonyl group, a cycloalkyloxycarbonyl group, an aryloxycarbonyl group, an amino group, an N-monosubstituted amino group, an N,N-disubstituted amino group, a carbamoyl group (—CO—NH$_2$), an N-monosubstituted carbamoyl group, an N,N-disubstituted carbamoyl group, a nitro group and a cyano group. The number carbon atoms in the substituent is not particularly limited within a range where the objects of the present invention are not impaired, but the number is preferably 1 or more and 10 or less, and more preferably 1 or more and 6 or less.

Suitable specific examples of the organic boron compound represented by the above formula (c1) include the following compounds. Note here that in the following formulae, Pen represents a pentyl group, Hex represents a hexyl group, Hep represents a heptyl group, Oct represents an octyl group, Non represents a nonyl group, and Dec represents a decyl group.

[Chem. 62]
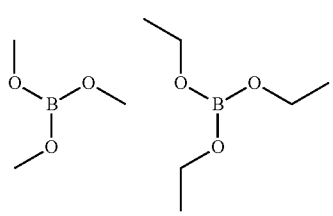
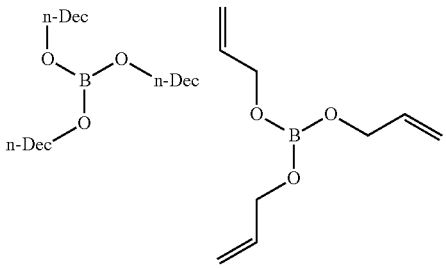
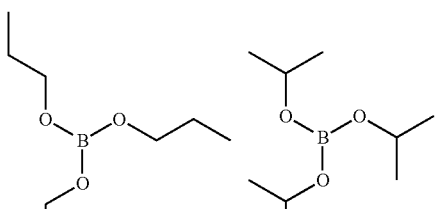
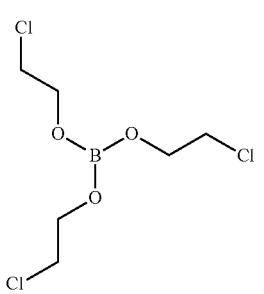
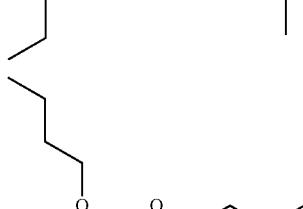
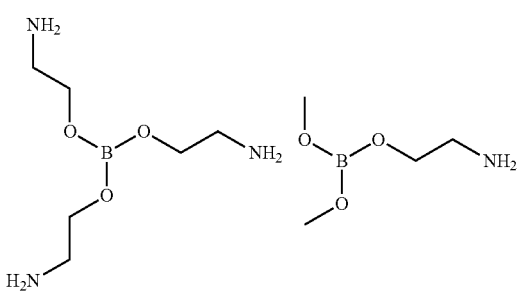
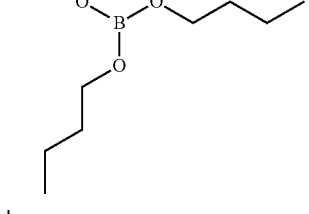
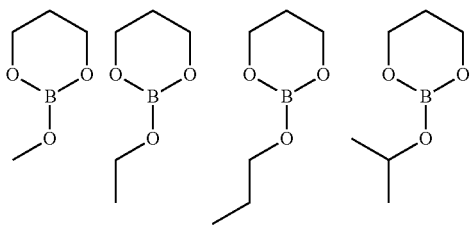
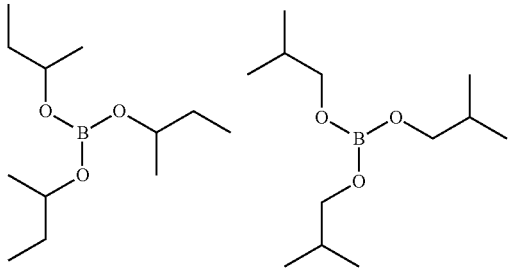
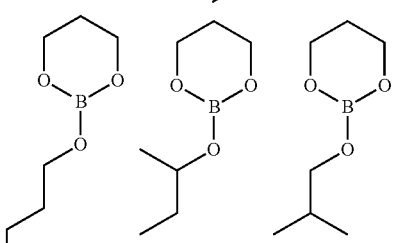
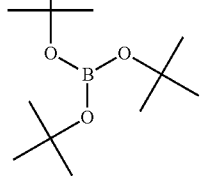
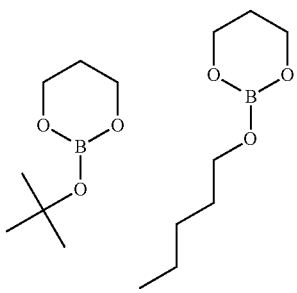
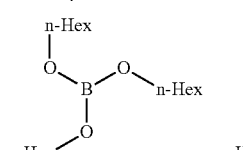
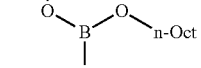

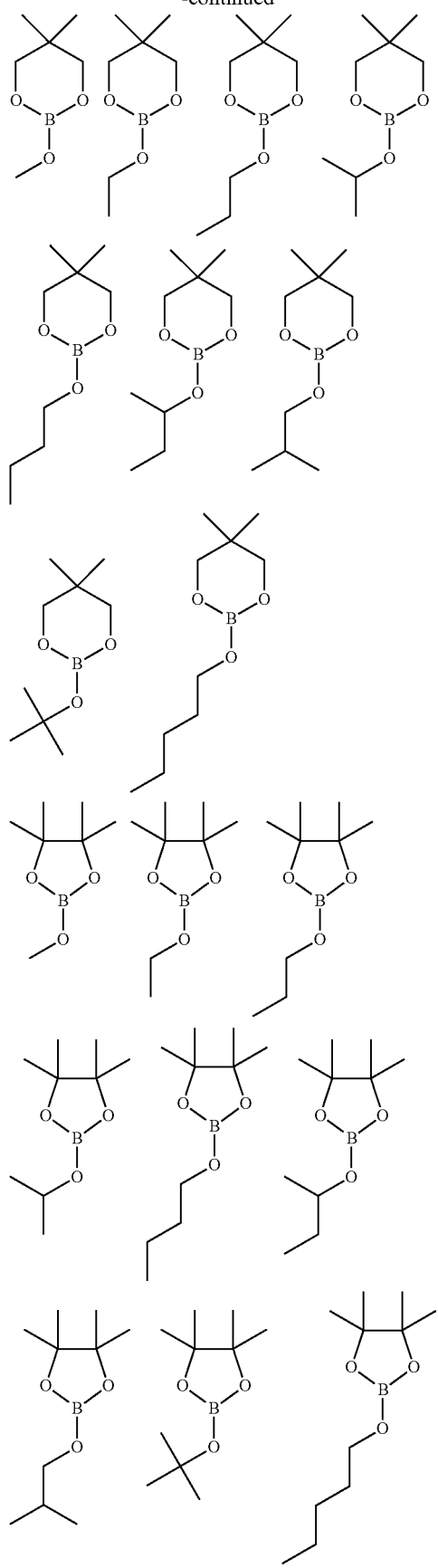
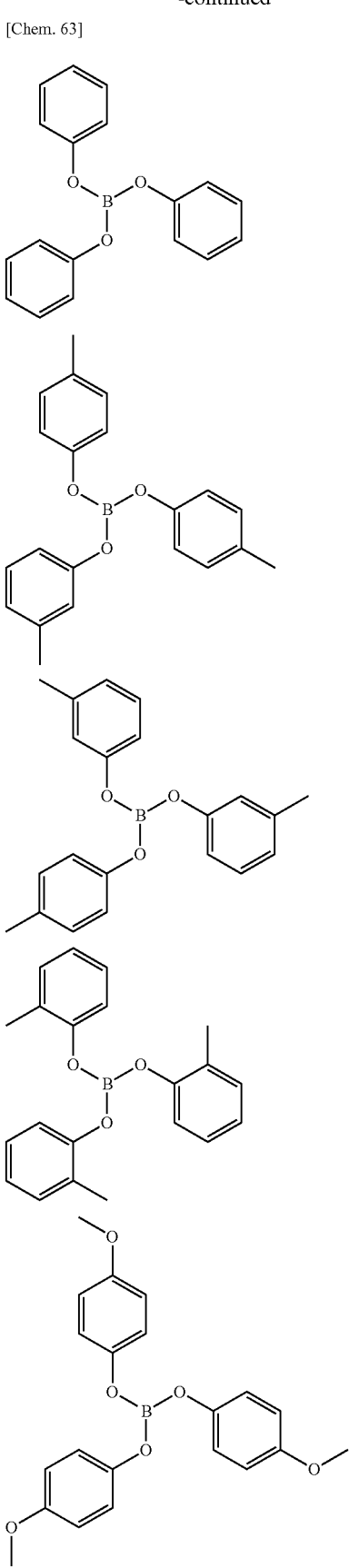
[Chem. 63]

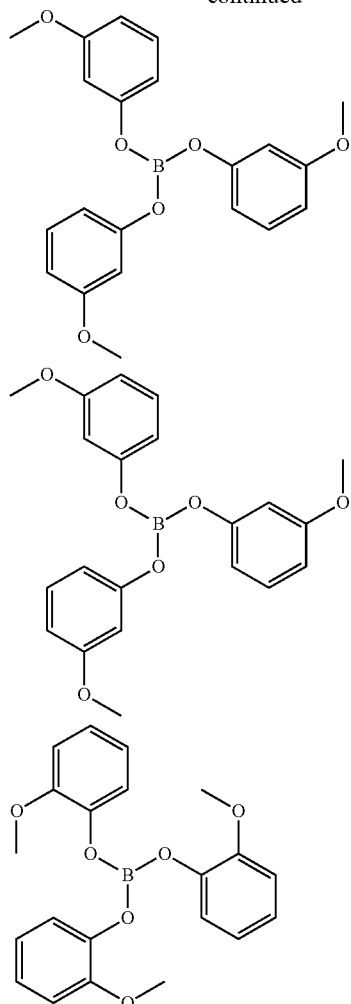
[Chem. 64]
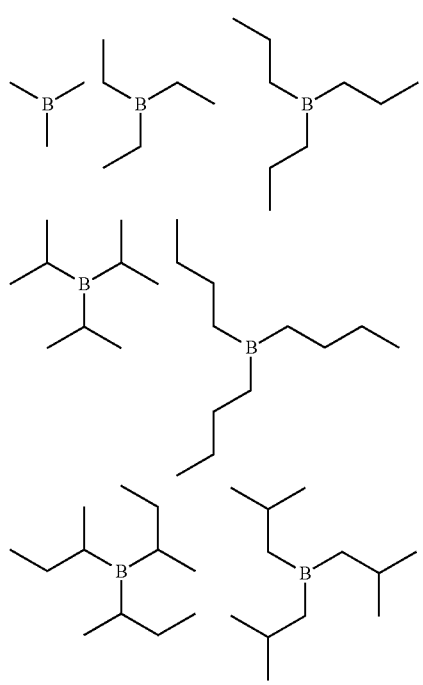
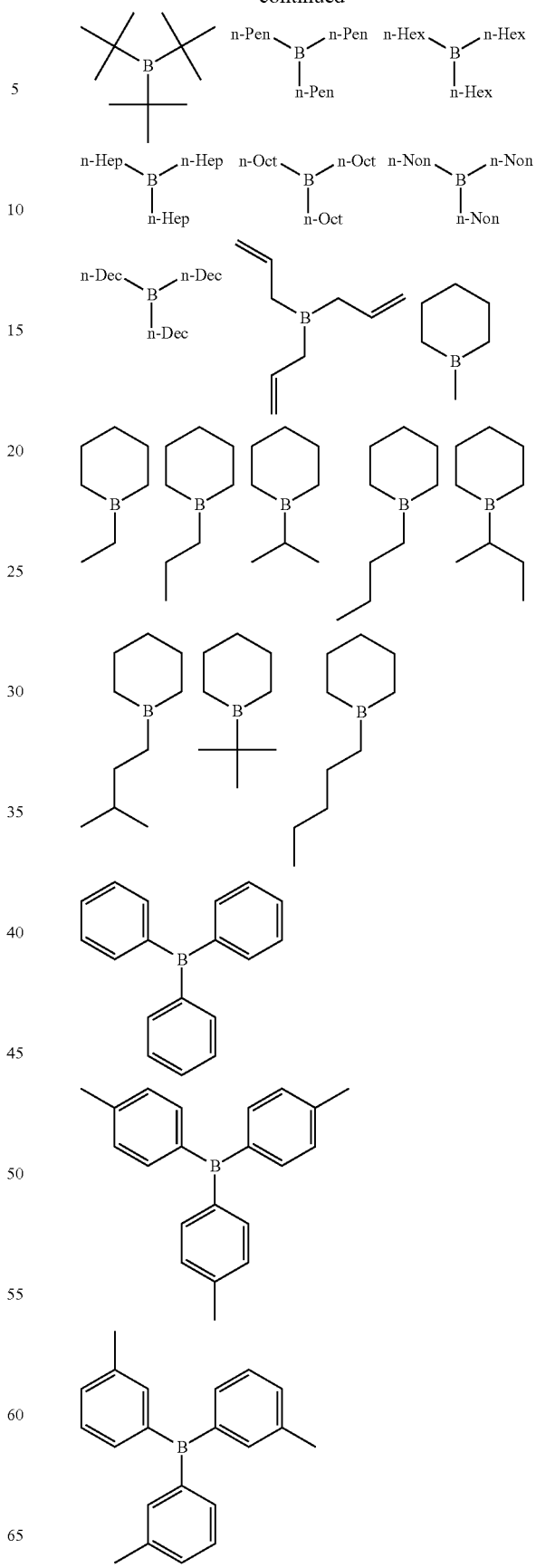

111
-continued
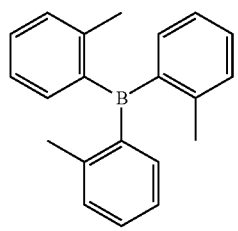
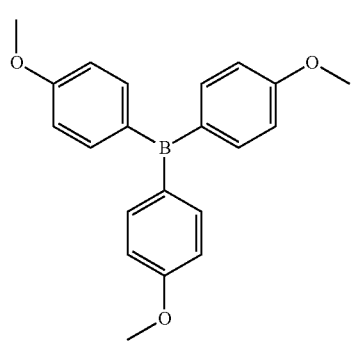
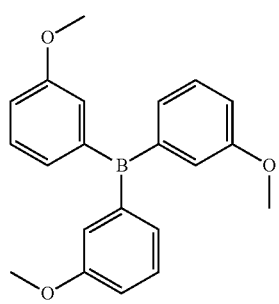
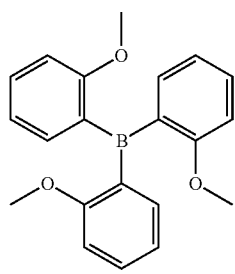 [SMILES: COc1ccccc1B(c1ccccc1OC)c1ccccc1OC]
[Chem. 65]
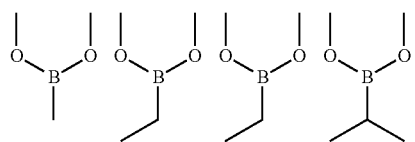
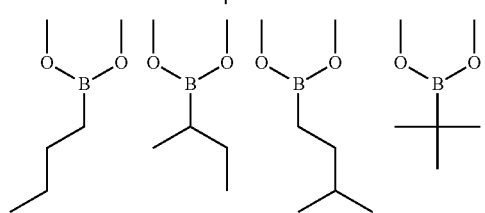
112
-continued
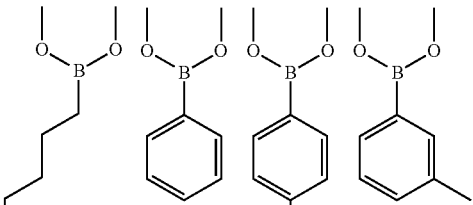
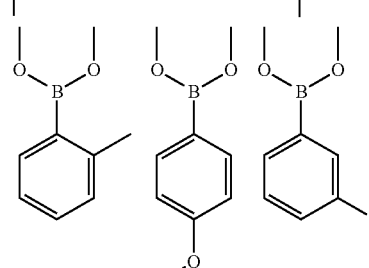
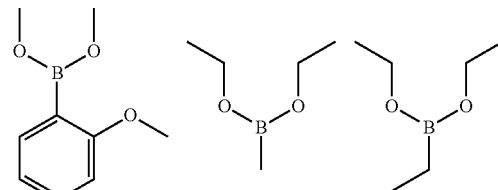
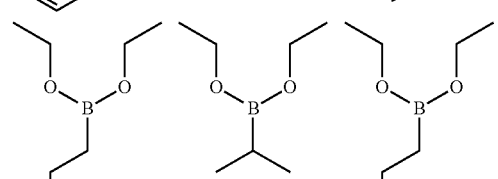
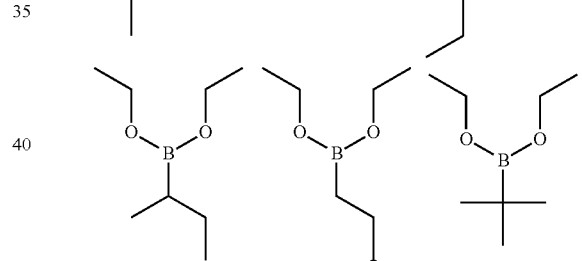
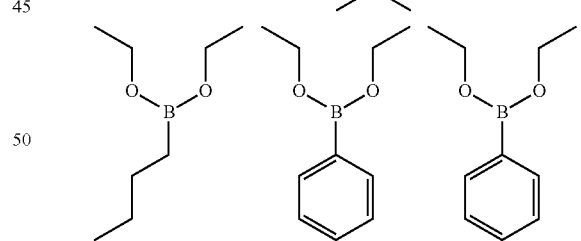
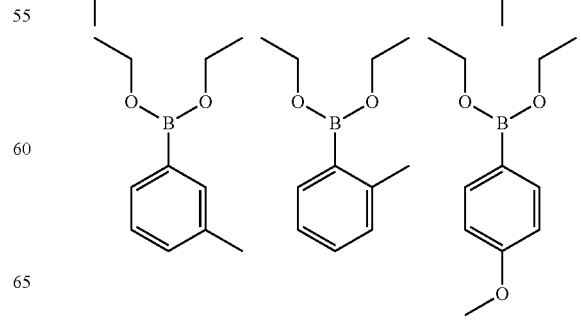

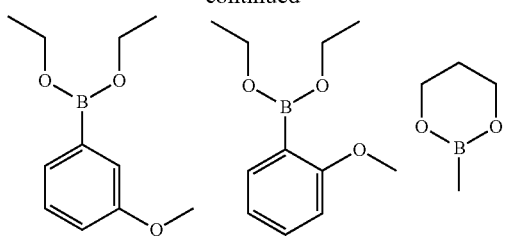
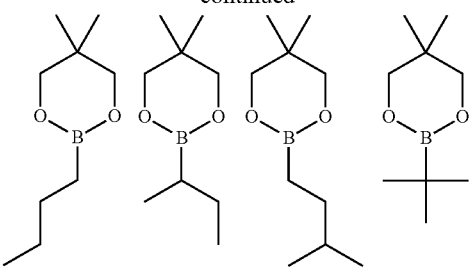
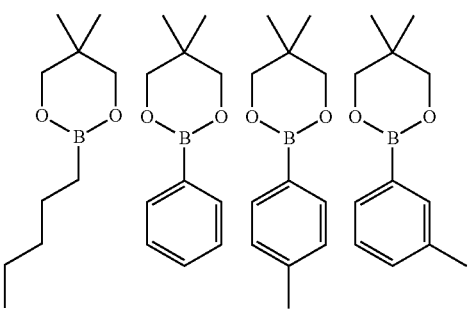
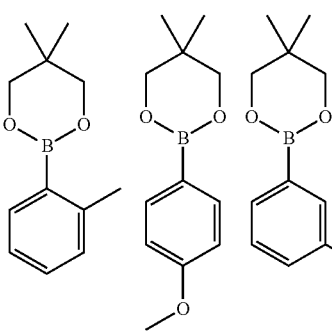
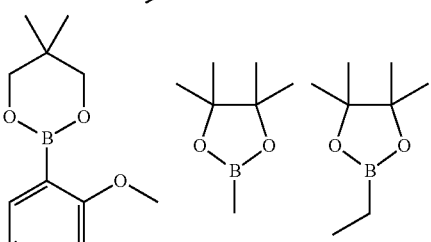
[Chem. 66]
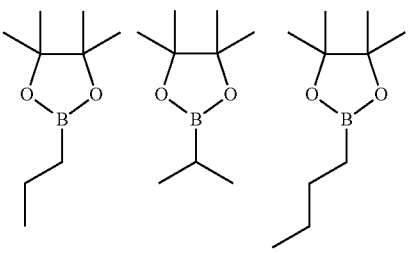
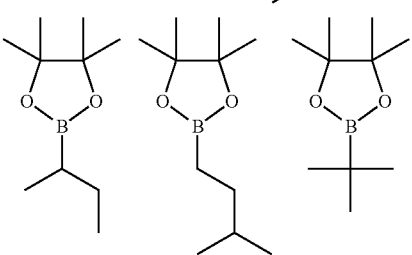

-continued

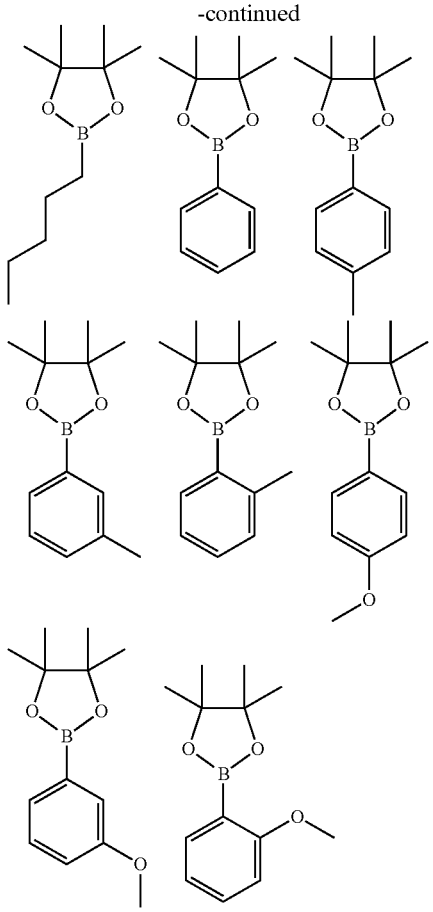

The Lewis acidic compound is used in the amount in a range of preferably 0.01 parts by mass or more and 5 parts by mass or less, more preferably 0.01 parts by mass or more and 3 parts by mass or less, further preferably 0.05 part by mass or more and 2 parts by mass or less, relative to 100 parts by mass of the total mass of the above resin (B) and the above alkali-soluble resin (D).

Further, when the photosensitive composition is used for forming pattern serving as a template for forming a plated article, the photosensitive composition may also contain an adhesive auxiliary agent in order to improve the adhesiveness between a template formed with the photosensitive composition and a metal substrate.

Also, the photosensitive composition may further contain a surfactant for improving coating characteristics, defoaming characteristics, leveling characteristics, and the like. As the surfactant, for example, a fluorine-based surfactant or a silicone-based surfactant is preferably used. Specific examples of the fluorine-based surfactant include commercially available fluorine-based surfactants such as BM-1000 and BM-1100 (both manufactured by B.M-Chemie Co., Ltd.), Megafac F142D, Megafac F172, Megafac F173 and Megafac F183 (all manufactured by Dainippon Ink And Chemicals, Incorporated), Flolade FC-135, Flolade FC-170C, Flolade FC-430 and Flolade FC-431 (all manufactured by Sumitomo 3M Ltd.), Surflon S-112, Surflon S-113, Surflon S-131, Surflon S-141 and Surflon S-145 (all manufactured by Asahi Glass Co., Ltd.), SH-28PA, SH-190, SH-193, SZ-6032 and SF-8428 (all manufactured by Toray Silicone Co., Ltd.) and the like, but not limited thereto. As the silicone-based surfactant, an unmodified silicone-based surfactant, a polyether modified silicone-based surfactant, a polyester modified silicone-based surfactant, an alkyl modified silicone-based surfactant, an aralkyl modified silicone-based surfactant, a reactive silicone-based surfactant, and the like, can be preferably used. As the silicone-based surfactant, commercially available silicone-based surfactant can be used. Specific examples of the commercially available silicone-based surfactant include Paintad M (manufactured by Dow Corning Toray Co., Ltd.), Topica K1000, Topica K2000, and Topica K5000 (all manufactured by Takachiho Industry Co., Ltd.), XL-121(polyether modified silicone-based surfactant, manufactured by Clariant Co.), BYK-310 (polyester modified silicone-based surfactant, manufactured by BYK), and the like.

Additionally, in order to finely adjust the solubility in a developing solution, the photosensitive composition may further contain an acid, an acid anhydride, or a solvent having a high boiling point.

Specific examples of the acid and acid anhydride include monocarboxylic acids such as acetic acid, propionic acid, n-butyric acid, isobutyric acid, n-valeric acid, isovaleric acid, benzoic acid, and cinnamic acid; hydroxymonocarboxylic acids such as lactic acid, 2-hydroxybutyric acid, 3-hydroxybutyric acid, salicylic acid, m-hydroxybenzoic acid, p-hydroxybenzoic acid, 2-hydroxycinnamic acid, 3-hydroxycinnamic acid, 4-hydroxycinnamic acid, 5-hydroxyisophthalic acid, and syringic acid; polyvalent carboxylic acids such as oxalic acid, succinic acid, glutaric acid, adipic acid, maleic acid, itaconic acid, hexahydrophthalic acid, phthalic acid, isophthalic acid, terephthalic acid, 1,2-cyclohexanedicarboxylic acid, 1,2,4-cyclohexanetricarboxylic acid, butanetetracarboxylic acid, trimellitic acid, pyromellitic acid, cyclopentanetetracarboxylic acid, butanetetracarboxylic acid, and 1,2,5,8-naphthalenetetracarboxylic acid; acid anhydrides such as itaconic anhydride, succinic anhydride, citraconic anhydride, dodecenylsuccinic anhydride, tricarbanilic anhydride, maleic anhydride, hexahydrophthalic anhydride, methyltetrahydrophthalic anhydride, Himic anhydride, 1,2,3,4-butanetetracarboxylic anhydride, cyclopentanetetracarboxylic dianhydride, phthalic anhydride, pyromellitic anhydride, trimellitic anhydride, benzophenonetetracarboxylic anhydride, ethylene glycol bis anhydrous trimellitate, and glycerin tris anhydrous trimellitate; and the like.

Furthermore, specific examples of the solvent having a high boiling point include N-methylformamide, N,N-dimethylformamide, N-methylformanilide, N-methylacetamide, N,N-dimethlyacetamide, N-methylpyrrolidone, dimethyl sulfoxide, benzyl ethyl ether, dihexyl ether, acetonyl acetone, isophorone, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, propylene carbonate, phenyl cellosolve acetate, and the like.

Moreover, the photosensitive composition may further contain a well-known sensitizer for improving the sensitivity.

«Method of preparing chemically amplified photosensitive composition>

A chemically amplified photosensitive composition is prepared by mixing and stirring the constituting component of the composition by the common method. Machines which can be used for mixing and stirring the above components include dissolvers, homogenizers, 3-roll mills and the like. After uniformly mixing the above components, the resulting mixture may be filtered through a mesh, a membrane filter and the like.

«Photosensitive Dry Film»

A photosensitive dry film includes a substrate film, and a photosensitive layer formed on the surface of the substrate film. The photosensitive layer is made of the aforementioned photosensitive compositions.

As the substrate film, a film having optical transparency is preferable. Specifically, a polyethylene terephthalate (PET) film, a polypropylene (PP) film, a polyethylene (PE) film, and the like. In view of excellent balance between the optical transparency and the breaking strength, a polyethylene terephthalate (PET) film is preferable.

The aforementioned photosensitive composition is applied on the substrate film to form a photosensitive layer, and thereby a photosensitive dry film is manufactured. When the photosensitive layer is formed on the substrate film, a photosensitive composition is applied and dried on the substrate film using an applicator, a bar coater, a wire bar coater, a roller coater, a curtain flow coater, and the like, so that a film thickness after drying is preferably 0.5 μm or more and 300 μm or less, more preferably 1 μm or more and 300 μm or less, and particularly preferably 3 μm or more and 100 μm or less.

The photosensitive dry film may have a protective film on the photosensitive layer. Examples of the protective film include a polyethylene terephthalate (PET) film, a polypropylene (PP) film, a polyethylene (PE) film, and the like.

«Method of Producing Patterned Resist Film, and Substrate with Template»

There is no particular limitation on a method of forming a patterned resist film on a substrate using the photosensitive composition described above. Such a patterned resist film is suitably used as a template and the like for forming an insulating film, an etching mask, and a plated article. A suitable method includes a manufacturing method of a patterned resist film, the method including:
laminating a photosensitive layer on a substrate, the layer being formed from a photosensitive composition;
exposing the photosensitive layer through irradiation with an active ray or radiation in a position-selective manner; and
developing the exposed photosensitive layer. A method of forming a substrate with a template for forming a plated article is the same method as the method of manufacturing a patterned resist film except that the method includes laminating a photosensitive layer on a metal surface of the substrate having a metal surface, and a template for forming a plated article is produced by developing in the developing step.

The substrate on which the photosensitive layer is laminated is not particularly limited, and conventionally known substrates can be used. Examples thereof include a substrate for an electronic component, and the substrate on which a predetermined wiring pattern is formed. As the substrate, a silicon substrate, glass substrate, or the like, can be used. When a substrate with a template for forming a plated article is manufactured, for the substrate, a substrate having a metal surface is used. As metal species constituting a metal surface, copper, gold and aluminum are preferred, and copper is more preferred. Since the above photosensitive composition has a wide depth of focus (DOF) margin, various substrates can be used regardless of the flatness of the surface of the substrate.

The photosensitive layer is laminated on the substrate, for example, as follows. In other words, a liquid photosensitive composition is coated onto a substrate, and the coating is heated to remove the solvent and thus to form a photosensitive layer having a desired thickness. The thickness of the photosensitive layer is not particularly limited as long as it is possible to form a resist pattern which has a desired thickness. The thickness of the photosensitive layer is not particularly limited, and is preferably 0.5 μm or more, more preferably 0.5 μm or more and 300 μm or less, further preferably 0.5 μm or more and 200 μm or less, and particularly preferably 0.5 μm or more and 150 μm or less. The upper limit of the film thickness may be, for example, 100 μm or less. The lower limit of the film thickness may be, for example, 1 μm or more, and may be 3 μm or more.

As a method of applying a photosensitive composition onto a substrate, methods such as the spin coating method, the slit coat method, the roll coat method, the screen printing method and the applicator method can be employed. Pre-baking is preferably performed on a photosensitive layer. The conditions of pre-baking may differ depending on the components in a photosensitive composition, the blending ratio, the thickness of a coating film and the like. They are usually about 2 minutes or more and 120 minutes or less at 70° C. or more and 200° C. or less, and preferably 80° C. or more and 150° C. or less.

The photosensitive layer formed as described above is selectively irradiated (exposed) with an active ray or radiation, for example, an ultraviolet radiation or visible light with a wavelength of 300 nm or more and 500 nm or less through a mask having a predetermined pattern.

Low pressure mercury lamps, high pressure mercury lamps, super high pressure mercury lamps, metal halide lamps, argon gas lasers, etc. can be used for the light source of the radiation. The radiation may include micro waves, infrared rays, visible lights, ultraviolet rays, X-rays, γ-rays, electron beams, proton beams, neutron beams, ion beams, etc. The irradiation dose of the radiation may vary depending on the constituent of the photosensitive composition, the film thickness of the photosensitive layer, and the like. For example, when an ultra-high-pressure mercury lamp is used, the dose may be 100 mJ/cm$^2$ or more and 10,000 mJ/cm$^2$ or less. The radiation includes a light ray to activate the acid generator (A) in order to generate an acid.

After the exposure, the diffusion of acid is promoted by heating the photosensitive layer using a known method to change the alkali solubility of the photosensitive layer in developing solution such as an alkali developing solution at an exposed portion in the photosensitive resin film.

Subsequently, the exposed photosensitive layer is developed in accordance with a conventionally known method, and an unnecessary portion is dissolved and removed to form a template for forming a predetermined resist pattern or plated articles. At this time, as the developing solution, an alkaline aqueous solution is used.

As the developing solution, an aqueous solution of an alkali such as, for example, sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, pyrrole, piperidine, 1,8-diazabicyclo[5.4.0]-7-undecene or 1,5-diazabicyclo[4.3.0]-5-nonane can be used. Also, an aqueous solution prepared by adding an adequate amount of a water-soluble organic solvent such as methanol or ethanol, or a surfactant to the above aqueous solution of the alkali can be used as the developing solution. Furthermore, depending on the composition of the photosensitive composition, developing by an organic solvent can be applied.

The developing time may vary depending on the composition of the photosensitive composition, the film thickness of the photosensitive layer, and the like. Usually, the developing time is 1 minute or more and 30 minutes or less. The method of the development may be any one of a liquid-filling method, a dipping method, a paddle method, a spray developing method, and the like.

After development, it is washed with running water for 30 seconds or more and 90 seconds or less, and then dried with an air gun, an oven, and the like. In this manner, it is possible to form a resist pattern, which has been patterned in a predetermined pattern on a metal surface of a substrate having a metal surface. Also, in this manner, it is possible to manufacture a resist pattern on a metal surface of a substrate having a metal surface.

«Method of Manufacturing Plated Article»

A conductor such as a metal may be embedded, by plating, into a nonresist portion (a portion removed with a developing solution) in the template formed by the above method on the substrate to form a plated article, for example, like a contacting terminal such as a bump and a metal post, or Cu rewiring. Note here that there is no particular limitation on the method of plate processing, and various conventionally known methods can be used. As a plating liquid, in particular, a solder plating liquid, a copper plating liquid, a gold plating liquid, and a nickel plating liquid are suitably used. The remaining template is removed with a stripping liquid and the like in accordance with a conventional method.

When the plated article is manufactured, it may be preferable that an exposed metal surface in a non-patterned portion of a resist pattern serving as a template for forming plated article is subjected to ashing treatment. Specific examples include case where a pattern formed of a photosensitive composition including a sulfur-containing compound (E) is used as a template to form a plated article. In this case, adhesiveness of the plated article to a metal surface may be easily damaged. This problem is remarkable in a case where sulfur-containing compound (E) represented by the above-mentioned formula (e1), and the sulfur-containing compound (E) represented by the formula (e4). However, the above-mentioned ashing treatment is carried out, even when a pattern formed using a photosensitive composition including a sulfur-containing compound (E) is used as a template, a plated article favorably adhering to the metal surface is easily obtained. Note here that in a case where a compound including a nitrogen-containing aromatic heterocycle substituted with a mercapto group is used as a sulfur-containing compound (E), the problem of adhesiveness of a plated article hardly occurs or occurs slightly. Therefore, in a case where a compound including a nitrogen-containing aromatic heterocycle substituted with a mercapto group is used as a sulfur-containing compound (E), a plated article having favorable adhesiveness with respect to the metal surface is easily formed without carrying out ashing treatment.

The ashing treatment is not particularly limited as long as long as it does not damage a resist pattern serving as a template for forming the plated article to such an extent that the plated article having a desired shape cannot be formed. Preferable ashing treatment methods include a method using oxygen plasma. For ashing with respect to the metal surface of the substrate using oxygen plasma, an oxygen plasma is generated using a known oxygen plasma generator, and the metal surface on the substrate is irradiated with the oxygen plasma.

Various gases which have conventionally been used for plasma treatment together with oxygen can be mixed into gas to be used for generating oxygen plasma within a range where the objects of the present invention are not impaired. Examples of such gas include nitrogen gas, hydrogen gas, $CF_4$ gas, and the like. Conditions of ashing using oxygen plasma are not particularly limited within a range where the objects of the present invention are not impaired, but treatment time is, for example, in a range of 10 seconds or more and 20 minutes or less, preferably in a range of 20 seconds or more and 18 minutes or less, and more preferably in a range of 30 seconds or more and 15 minutes or less. By setting the treatment time by oxygen plasma to the above range, an effect of improving the adhesiveness of the plated article can be easily achieved without changing a shape of the resist pattern.

According to the above method, since a resist pattern whose cross-sectional shape is a favorable rectangular shape can be used as a template for formation of a plated article, a wide contact area between the plated article and a surface the substrate can be easily secured, a plated article having excellent adhesion to the substrate can be obtained.

Note here that the compound represented by the above formula (C2) is a new compound. The compound represented by the formula (C2) can also be contained in photosensitive compositions other than the photosensitive composition of the present invention mentioned above, and can be used for applications other than photosensitive compositions.

EXAMPLES

The present invention will be described in more detail below by way of Examples, but the present invention is not limited to these Examples.

Preparation Example 1

(Synthesis of Mercapto Compound E1)

In Preparation Example 1, a mercapto compound T2 having the following structure was synthesized as sulfur-containing compound (E).

[Chem. 67]

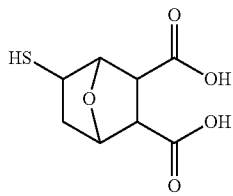

T2

In a flask, 15.00 g of 7-oxanorborna-5-ene-2,3-dicarboxylic anhydride and 150.00 g of tetrahydrofuran were added, followed by stirring. Subsequently, 7.64 g of thioacetic acid (AcSH) was added in a flask, followed by stirring at room temperature for 3.5 hours. Then, the reaction solution was concentrated to obtain 22.11 g of 5-acetyl thio-7-oxanorbornane-2,3-dicarboxylic anhydride. In a flask, 22.11 g of 5-acetylthio-7-oxanorbornane-2,3-dicarboxylic anhydride and 30.11 g of an aqueous sodium hydroxide solution having the concentration of 10% by mass were added, and then contents in the flask were stirred at room temperature for 2 hours. Subsequently, hydrochloric acid (80.00 g) having the concentration of 20% by mass was added in the flask to acidify the reaction solution. Then, extraction with 200 g of ethyl acetate was performed four times to obtain an extraction liquid including a mercapto compound T2. The extraction liquid was concentrated and the collected residue was dissolved by adding 25.11 g of tetrahydrofuran (THF). Heptane was added dropwise to the obtained THF solution to precipitate the mercapto compound T2, and the precipitated mercapto compound T2 was collected by filtration. The measurement results of $^1$H-NMR of the mercapto compound T2 are shown below.

$^1$H-NMR (DMSO-d6): δ12.10 (s, 2H), 4.72 (d, 1H), 4.43 (s, 1H), 3.10 (t, 1H), 3.01 (d, 1H), 2.85 (d, 1H), 2.75 (d, 1H), 2.10 (t, 1H), 1.40 (m, 1H)

[Chem. 68]

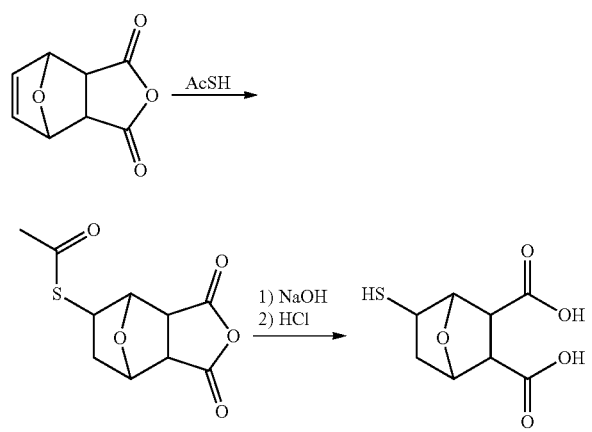

(Preparation of Compound Represented by the Following Formula (C$_1$))

Preparation Example 1

As a compound represented by the following formula (C1), a compound Q3 having the following structure was synthesized.

[Chem. 69]

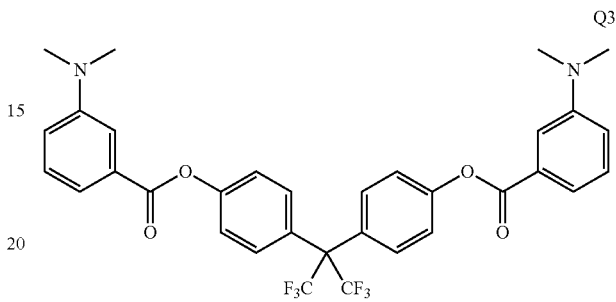

Q3

In a flask, 3.7 g of dimethylaminobenzoic acid and 56.0 g of dichloromethane were added, followed by stirring. Subsequently, 4.3 g of carbodiimide compound (WSC) was added thereto, followed by stirring, and 3.0 g of the following alcohol (3) and 0.14 g of dimethylaminopyridine were added thereto, followed by stirring. Then, the reaction solution was washed with dilute hydrochloric acid and water to obtain concentrated solution. Then, heptane was added dropwise to the concentrated solution to precipitate Q3, and 3.4 g of the precipitated product was collected by filtration. The measurement results of $^1$H-NMR of the compound Q3 are shown below.

$^1$H-NMR (DMSO-d6): δ=8.21 (d, 4H), 7.47 (m, 4H), 7.25 (d, 4H), 6.89 (d, 4H), 3.09 (s, 12H) Also, the reaction formula is shown below.

[Chem. 70]

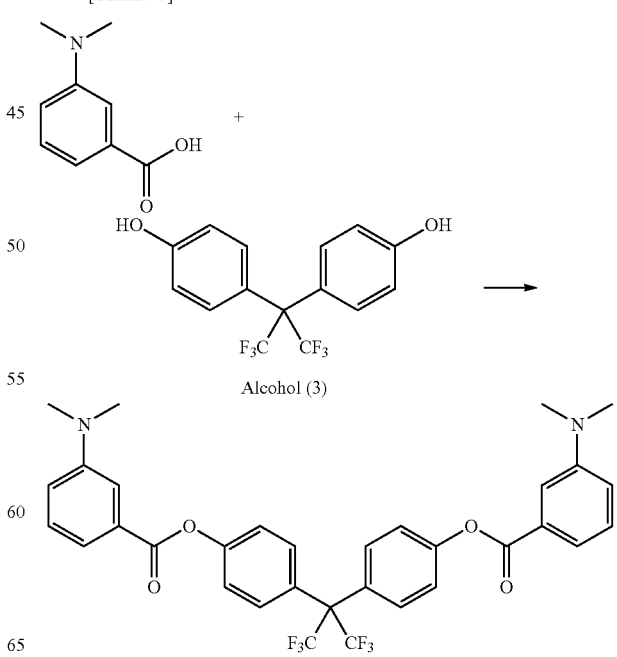

Preparation Example 2

As a compound represented by the following formula (C1), a compound Q4 having the following structure was synthesized.

[Chem. 71]

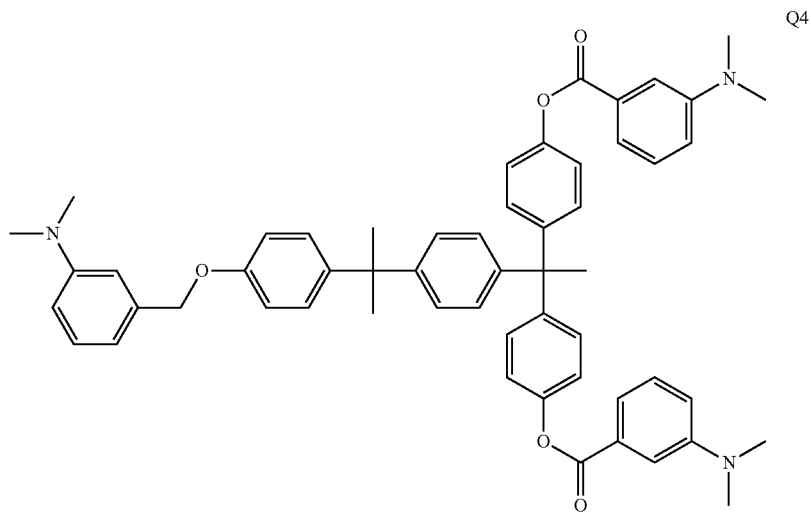

In a flask, 2.0 g of dimethylaminobenzoic acid and 32.0 g of dichloromethane were added, followed by stirring. Subsequently, 2.6 g of carbodiimide compound (WSC) was added thereto, followed by stirring, and 1.6 g of the following alcohol (4) and 0.15 g of dimethylaminopyridine were added thereto, followed by stirring. Then, the reaction solution was washed with dilute hydrochloric acid and water to obtain concentrated solution. Then, heptane was added dropwise to the concentrated solution to precipitate Q4, and 2.4 g of the precipitated product was collected by filtration. The measurement results of $^1$H-NMR of the compound Q4 are shown below.

$^1$H-NMR (DMSO-d6): δ=7.03-7.42 (m, 28H), 2.95 (s, 18H), 2.16 (s, 3H), 1.66 (s, 6H) Also, the reaction formula is shown below.

[Chem. 72]

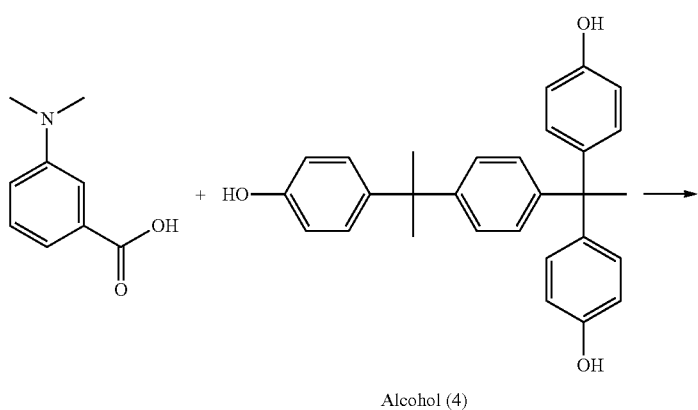

Alcohol (4)

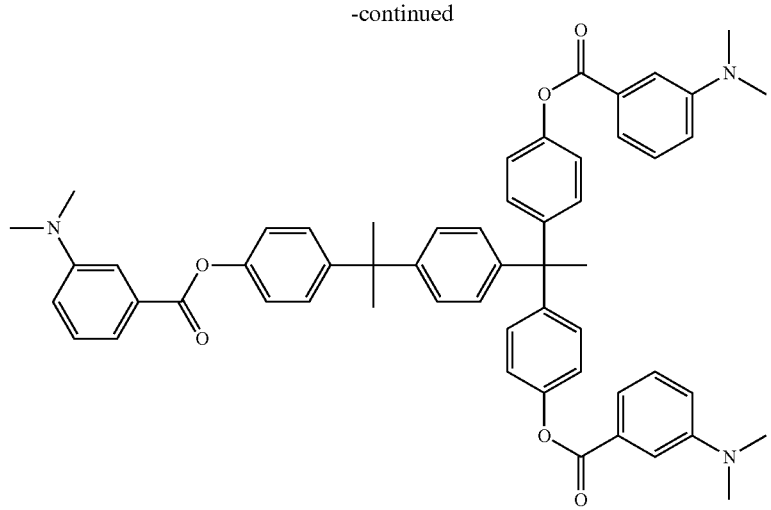

Preparation Example 3

As a compound represented by the following formula (C1), a compound Q5 having the following structure was synthesized.

[Chem. 73]

Q5

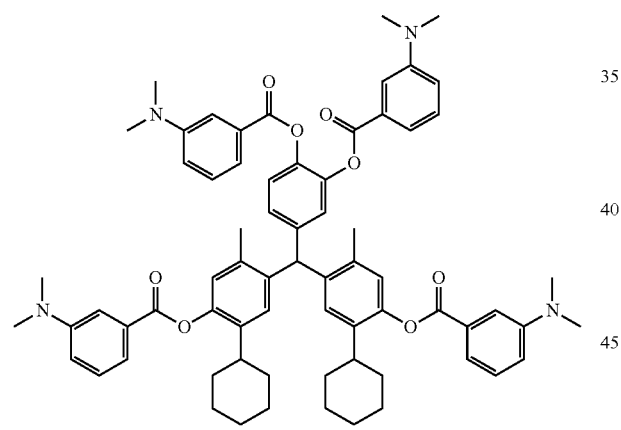

In a flask, 3.3 g of dimethylaminobenzoic acid and 50.0 g of dichloromethane were added, followed by stirring. Subsequently, 4.3 g of carbodiimide compound (WSC) was added thereto, followed by stirring, and 2.3 g of the following alcohol (5) and 0.25 g of dimethylaminopyridine were added thereto, followed by stirring. Then, the reaction solution was washed with dilute hydrochloric acid and water to obtain concentrated solution. Then, heptane was added dropwise to the concentrated solution to precipitate Q5, and 4.9 g of the precipitated product was collected by filtration. The measurement results of $^1$H-NMR of the compound Q5 are shown below.

$^1$H-NMR (DMSO-d6): δ=6.83-7.61 (m, 23H), 5.12 (s, 1H), 2.95 (s, 12H), 2.81 (s, 12H), 2.21 (s, 6H), 1.49-1.81 (m, 10H), 1.02-1.33 (m, 10H)

Also, the reaction formula is shown below.

[Chem. 74]

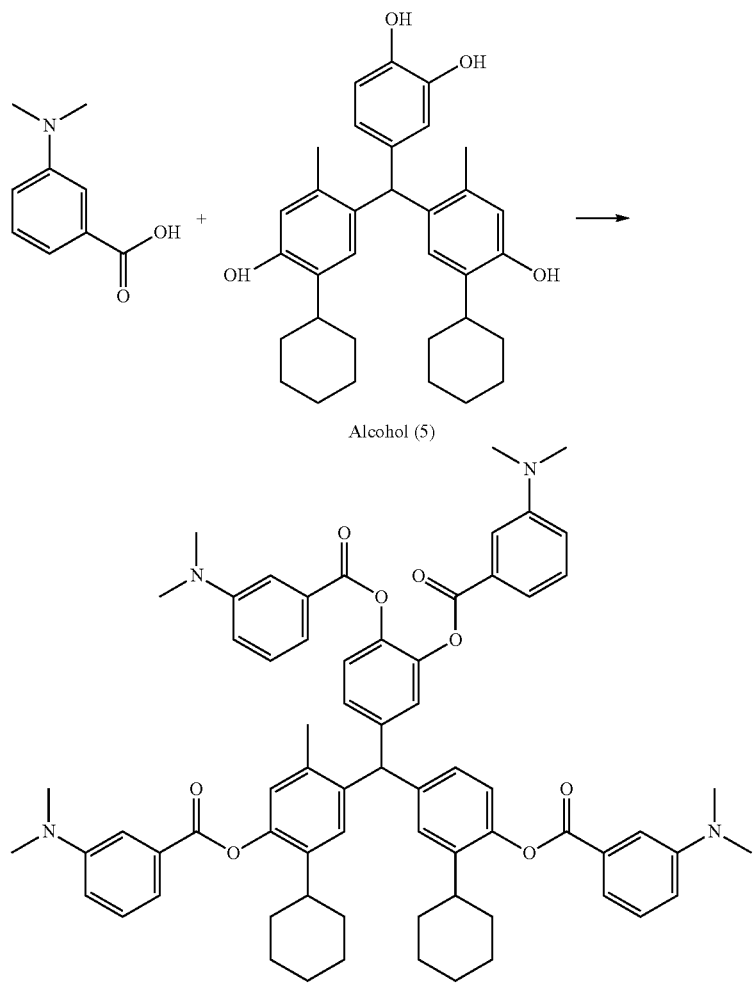

Alcohol (5)

Preparation Example 4

As a compound represented by the following formula (C1), a compound Q6 having the following structure was synthesized.

[Chem. 75]

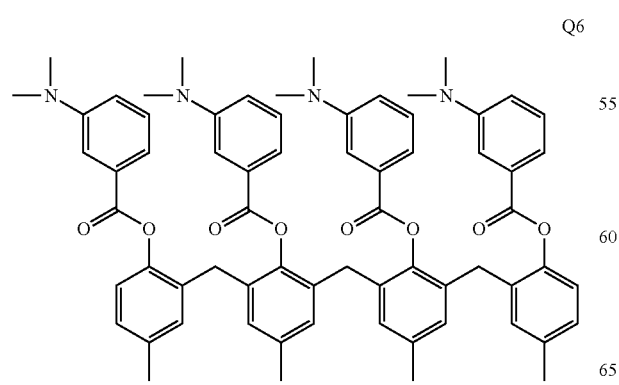

Q6

In a flask, 3.4 g of dimethylaminobenzoic acid and 50.0 g of dichloromethane were added, followed by stirring. Subsequently, 4.4 g of carbodiimide compound (WSC) was added thereto, followed by stirring, and 2.2 g of the following alcohol (6) and 0.25 g of dimethylaminopyridine were added thereto, followed by stirring. Then, the reaction solution was washed with dilute hydrochloric acid and water to obtain concentrated solution. Then, heptane was added dropwise to the concentrated solution to precipitate Q6, and 4.9 g of the precipitated product was collected by filtration. The measurement results of $^1$H-NMR of the compound Q6 are shown below.

$^1$H-NMR (DMSO-d6): δ=6.40-7.42 (m, 26H), 3.45-3.80 (m, 6H), 2.83 (d, 24H), 1.75-2.11 (m, 12H)

Also, the reaction formula is shown below.

[Chem. 76]

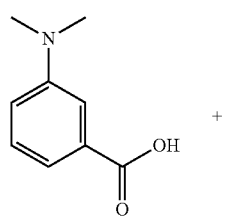 +

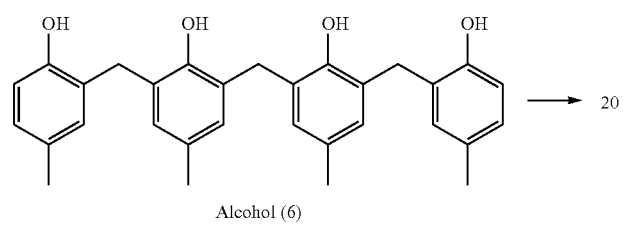

Alcohol (6)

→

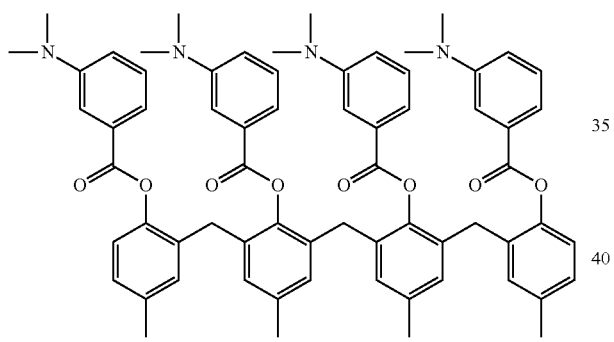

Examples 1 to 24 and Comparative Examples 1 to 10

In Examples 1 to 24 and Comparative Examples 1 to 10, as the acid diffusion suppressing agent (C), compounds Q1 to Q2 of the following formula and the above Q3 to Q6 were used.

[Chem. 77]

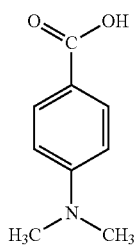

Q1

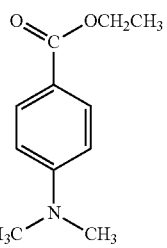

Q2

In Examples 1 to 24 and Comparative Examples 1 to 10, as the acid generator (A), PAG A1 and PAG A2 of the following formula were used.

[Chem. 78]

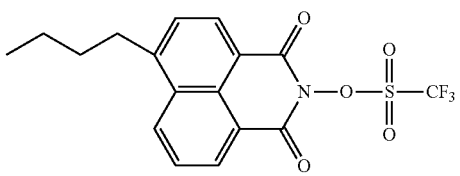

PAG A1

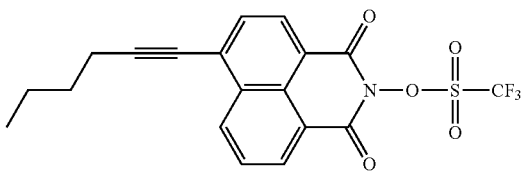

PAG A2

In Examples 1 to 24 and Comparative Examples 1 to 10, the following Resin A1 to Resin A3 were used as the resin whose solubility in alkali increases under an action of acid (resin (B)). The number at the lower right of the parentheses in each constituent unit in the following structural formula represents the content (% by mass) of the constituent unit in each resin. Resin A1 has a mass average molecular weight Mw of 42000. Resin A2 has a mass average molecular weight Mw of 4200. Resin A3 has a mass average molecular weight Mw of 42000.

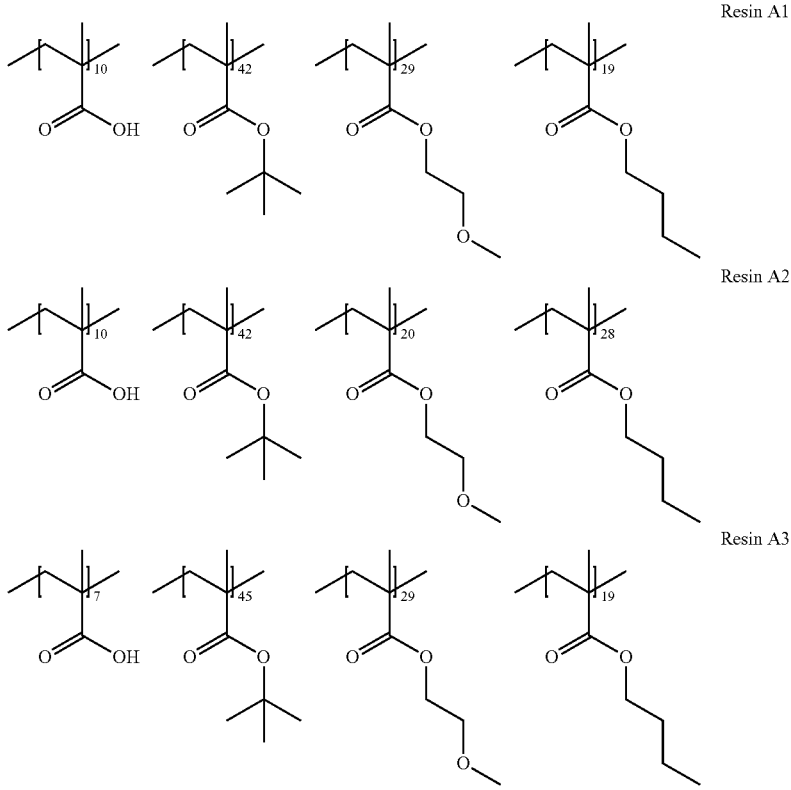

Examples 1 to 24 and Comparative Examples 1 to 10, the following Resin B1 (polyhydroxystyrene resin) and Resin C (novolac resin (m-cresol single condensate)) were used as the alkali-soluble resin resin (D). The number at the lower right of the parentheses in each constituent unit in the following structural formula represents the content (% by mass) of the constituent unit in each resin. Resin B1 has a mass average molecular weight (Mw) of 2500, and dispersivity (Mw/Mn) of 2.4. Resin C has a mass average molecular weight (Mw) of 8000.

[Chem. 80]

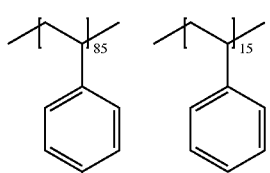

[Chem. 81]

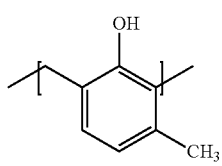

As the sulfur-containing compound (E), the following sulfur-containing compounds T1 to T3 were used.

[Chem. 82]

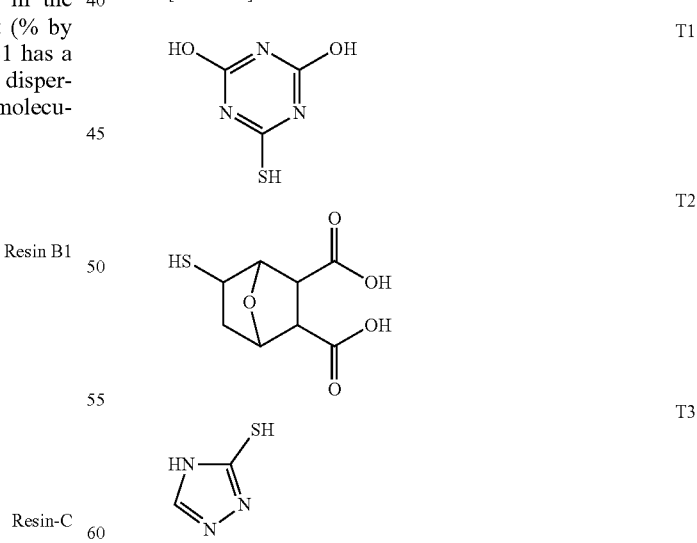

The acid generator (A), the resin (B), the acid diffusion suppressing agent (C), the alkali-soluble resin (D), and the sulfur-containing compound (E) in types and amounts shown in Table 1, and 0.05 parts by mass of surfactant (BYK310, manufactured by BYK) were dissolved in a mixed solvent of 3-methoxybutyl acetate (MA) and propylene glycol monomethyl ether acetate (PM) (MA/PM=6/4 (mass ratio)) so that the solid content concentration became 40% by mass to obtain positive-type photosensitive compositions of Examples and Comparative Examples.

Using the obtained positive-type photosensitive composition, shapes, and margins of depth of focus (DOF) were evaluated according to the following methods. These evaluation results are shown in Table 1.

[Shape Evaluation]

The photosensitive compositions of Examples and Comparative Examples were each applied on a copper substrate having a diameter of 8 inches to form a photosensitive layer (coated film of the photosensitive composition) having a thickness of 8 µm. Then, the photosensitive layer was pre-baked at 130° C. for 5 minutes. After the pre-baking, using a mask having a line-and-space pattern having a line width of 2.0 µm and a space width of 2.0 µm, and Canon PLA501F Hardcontact (manufactured by Canon Inc.), pattern exposure was performed with an ultraviolet ray having a wavelength of 365 nm at an exposure dose greater by 1.2 times than the minimum exposure dose capable of forming a pattern having a predetermined size. Subsequently, the substrate was mounted on a hot plate and post-exposure baking (PEB) was performed at 90° C. for 1.5 minutes. Immediately after PEB, an aqueous 2.38% by weight solution of tetramethylammonium hydroxide (TMAH) (developing solution, NMD-3, manufactured by Tokyo Ohka Kogyo Co., Ltd.) was added dropwise to the exposed photosensitive layer, and allowed to stand at 23° C. for 30 seconds. This operation was repeated three times in total. Subsequently, the surface of the resist pattern was washed (rinsed) with running water, and blown with nitrogen to obtain a resist pattern. The cross-sectional shape of this resist pattern was observed under a scanning electron microscope to evaluate the cross-sectional shape of the pattern. Specifically, when Wb represents a width of a surface (bottom) of the substrate with which the resist pattern is to be brought into contact, Wt represents a width of a surface (top) opposite to the surface of the substrate with which the resist pattern is to be brought into contact, and Wm represents a pattern width of the intermediate part in the thickness direction of the resist pattern cross-section, when Wm was within ±10% of Wb and within ±10% of Wt, the shape was evaluated as "o"; when Wm was at least one of beyond ±10% of Wb and beyond ±10% of Wt, the shape was evaluated as to "x".

[Evaluation of Depth of Focus (DOF) Margin]

A line-and-space pattern having a line width of 1.5 µm and a space width of 1.5 µm was formed by the same method as in [Evaluation of shape]. At this time, a range of focus in which patterns were independent from each other and capable of self-standing was examined. In the case where the range of focus was improved by 20% or more, the case was evaluated as ⊚, improved by 10% or more and less than 20%, the case was evaluated as o, and improved by less than 10% or not improved, the case was evaluated as x, based on the improvement with respect to Comparative Example 1 in Examples 1 to 8 and Comparative Example 2, with respect to Comparative Example 3 in Examples 9 to 12 and Comparative Example 4, with respect to Comparative Example 5 in Examples 13 to 16 and Comparative Example 6, with respect to Comparative Example 7 in Examples 17 to 20 and Comparative Example 8, and with respect to Comparative Example 9 in Examples 21 to 24 and Comparative Example 10, respectively.

TABLE 1

| | Acid generator (A) Type/part(s) by mass | Resin (B) and alkali-soluble resin (D) Type/part(s) by mass | Acid diffusion suppressing agent (C) Type/part(s) by mass | Sulfur-containing compound (E) Type/part(s) by mass | Evaluation Shape | Evaluation DOF |
|---|---|---|---|---|---|---|
| Example 1 | A1/1.0 | A1/35 | Q3/1.79 | T1/0.05 | ○ | ○ |
| Example 2 | | B1/10 | Q3/1.97 | T3/0.05 | ○ | ⊚ |
| Example 3 | | C/55 | Q4/1.64 | | ○ | ⊚ |
| Example 4 | | | Q4/1.80 | | ○ | ○ |
| Example 5 | | | Q5/1.55 | | ○ | ⊚ |
| Example 6 | | | Q5/1.70 | | ○ | ○ |
| Example 7 | | | Q6/1.50 | | ○ | ○ |
| Example 8 | | | Q6/1.65 | | ○ | ⊚ |
| Comparative Example 1 | | | Q1/0.94 | | X | — |
| Comparative Example 2 | | | Q2/1.10 | | X | X |
| Example 9 | | A2/35 | Q3/1.79 | | ○ | ○ |
| Example 10 | | B1/10 | Q4/1.64 | | ○ | ⊚ |
| Example 11 | | C/55 | Q5/1.55 | | ○ | ○ |
| Example 12 | | | Q6/1.50 | | ○ | ○ |
| Comparative Example 3 | | | Q1/0.94 | | X | — |
| Comparative Example 4 | | | Q2/1.10 | | X | X |
| Example 13 | | A3/35 | Q3/1.79 | | ○ | ○ |
| Example 14 | | B1/10 | Q4/1.64 | | ○ | ⊚ |
| Example 15 | | C/55 | Q5/1.55 | | ○ | ○ |
| Example 16 | | | Q6/1.50 | | ○ | ○ |
| Comparative Example 5 | | | Q1/0.94 | | X | — |
| Comparative Example 6 | | | Q2/1.10 | | X | X |

TABLE 2

| | Acid generator (A) Type/part(s) by mass | Resin (B) and alkali-soluble resin (D) Type/part(s) by mass | Acid diffusion suppressing agent (C) Type/part(s) by mass | Sulfur-containing compound (E) Type/part(s) by mass | Evaluation Shape | Evaluation DOF |
|---|---|---|---|---|---|---|
| Example 17 | A2/1.0 | A3/35 | Q3/1.79 | T1/0.05 | ○ | ○ |
| Example 18 | | B1/10 | Q4/1.64 | T3/0.05 | ○ | ⊚ |
| Example 19 | | C/55 | Q5/1.55 | | ○ | ○ |
| Example 20 | | | Q6/1.50 | | ○ | ○ |
| Comparative Example 7 | | | Q1/0.94 | | X | — |
| Comparative Example 8 | | | Q2/1.10 | | X | X |
| Example 21 | | | Q3/1.79 | T2/0.10 | ○ | ○ |
| Example 22 | | | Q4/1.64 | | ○ | ○ |
| Example 23 | | | Q5/1.55 | | ○ | ○ |
| Example 24 | | | Q6/1.50 | | ○ | ○ |
| Comparative Example 9 | | | Q1/0.94 | | X | — |
| Comparative Example 10 | | | Q2/1.10 | | X | X |

According to Examples 1 to 24, it is shown that a chemically amplified photosensitive composition including an acid generator (A) which generates acid upon exposure to an irradiated active ray or radiation including a compound represented by the formula (C1) as an acid diffusion suppressing agent (C) can form a resist pattern whose cross-sectional shape is favorably rectangular, and has a wide depth of focus (DOF) margin.

On the other hand, according to Comparative Examples 1 to 10, when a photosensitive composition includes a compound Q1 or a compound Q2 as the acid diffusion suppressing agent that did not correspond to the compound represented by the formula (C1) instead of the compound represented by the formula (C1), the shape was taper shape in which the cross-sectional shape was narrower at the top or bottom of the resist pattern, thus making it difficult to form a resist pattern whose cross-sectional shape is favorably rectangular. Furthermore, in Comparative Examples 1 to 10, the depth of focus was narrower as compared with Examples 1 to 24.

What is claimed is:

1. A chemically amplified photosensitive composition comprising an acid generator (A) which generates acid upon exposure to an irradiated active ray or radiation, and an acid diffusion suppressing agent (C), wherein the chemically amplified photosensitive composition comprises a resin (B) whose solubility in alkali increases under an action of acid, a resin which can be crosslinked by a condensing agent, or an epoxy compound, and the acid diffusion suppressing agent (C) comprises a compound represented by the following formula (C2):

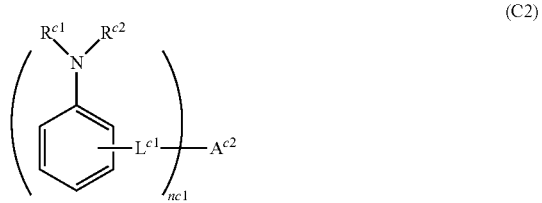

(C2)

wherein a plurality of $R^{c1}$ each independently is an alkyl group having 1 or more and 6 or less carbon atoms optionally having a substituent, or a hydrogen atom;

a plurality of $R^{c2}$ each independently is an alkyl group having 1 or more and 6 or less carbon atoms optionally having a substituent, or a hydrogen atom;

$R^{c1}$ and $R^{c2}$ may be linked to each other to form a ring;

$A^{c2}$ is an nc1-valence organic group including two or more aromatic groups optionally having a substituent;

a plurality of $L^{c1}$ each independently is a single bond or a divalent linking group;

$L^{c1}$ is bonded to the aromatic group in $A^{c2}$; and nc1 is an integer of 2 or more.

2. The chemically amplified photosensitive composition according to claim 1, wherein $L^{c1}$ is a divalent group selected from the group consisting of —O—, —CO—, —COO—, —OCOO—, —NH—, —CONH—, —NHCONH—, —S—, —SO—, and —SO$_2$—.

3. The chemically amplified photosensitive composition according to claim 1, wherein $L^{c1}$ is —COO—.

4. The chemically amplified photosensitive composition according to claim 1, wherein said composition is a positive type.

5. The chemically amplified photosensitive composition according to claim 4, further comprising a resin (B) whose solubility in alkali increases under an action of acid.

6. The chemically amplified photosensitive composition according to claim 4, further comprising an alkali-soluble resin (D).

7. The chemically amplified photosensitive composition according to claim 6, wherein the alkali-soluble resin (D) comprises at least one resin selected from the group consisting of a novolac resin (D1), a polyhydroxystyrene resin (D2), and an acrylic resin (D3).

8. The chemically amplified photosensitive composition according to claim 1, further comprising a sulfur-containing compound (E) including a sulfur atom to be coordinated to metal.

9. A photosensitive dry film comprising a substrate film, and a photosensitive layer formed on a surface of the substrate film, wherein the photosensitive layer includes the chemically amplified photosensitive composition according to claim 1.

10. A method of manufacturing a patterned resist film, the method comprising:
laminating a photosensitive layer on a substrate, the layer including the chemically amplified photosensitive composition according to claim 1;
exposing the photosensitive layer by irradiation with an active ray or radiation in a position-selective manner; and
developing the exposed photosensitive layer.

11. A method of manufacturing a substrate with a template, the method comprising:
laminating a photosensitive layer on a substrate having a metal surface, the layer including the chemically amplified photosensitive composition according to claim 1;
exposing the photosensitive layer by irradiation with an active ray or radiation in a position-selective manner; and
developing the exposed photosensitive layer to form a template for forming a plated article.

12. A method of manufacturing a plated article, the method comprising plating the substrate with a template to form a plated article in the template, wherein the substrate is manufactured by the method of manufacturing substrate with a template according to claim 11.

13. The chemically amplified photosensitive composition according to claim 1, wherein the nc1 is an integer of 3 or more.

* * * * *